US010501405B2

(12) United States Patent
Hormann et al.

(10) Patent No.: US 10,501,405 B2
(45) Date of Patent: Dec. 10, 2019

(54) CRYSTALLINE DIACYLHYDRAZINE AND THE USE THEREOF

(71) Applicant: Intrexon Corporation, Blacksburg, VA (US)

(72) Inventors: Robert E. Hormann, Elkins Park, PA (US); Inna Shulman, Langhorne, PA (US); Eva Rödel, Basel (CH); Rolf Hilfiker, Allschwil (CH); Susan M. De Paul, Zürich (CH)

(73) Assignee: INTREXON CORPORATION, Blacksburg, VA (US)

( * ) Notice: Subject to any disclaimer, the term of this patent is extended or adjusted under 35 U.S.C. 154(b) by 22 days.

(21) Appl. No.: 15/398,236

(22) Filed: Jan. 4, 2017

(65) Prior Publication Data

US 2017/0107175 A1    Apr. 20, 2017

Related U.S. Application Data

(62) Division of application No. 14/519,408, filed on Oct. 21, 2014, now Pat. No. 9,604,913, which is a division of application No. 13/606,444, filed on Sep. 7, 2012, now Pat. No. 8,946,294.

(60) Provisional application No. 61/532,368, filed on Sep. 8, 2011.

(51) Int. Cl.
| | | |
|---|---|---|
| *C07D 243/38* | (2006.01) | |
| *A01N 37/28* | (2006.01) | |
| *C07C 243/38* | (2006.01) | |
| *A01N 37/40* | (2006.01) | |
| *A61K 31/166* | (2006.01) | |
| *A61K 47/10* | (2017.01) | |
| *A61K 47/12* | (2006.01) | |
| *A61K 47/22* | (2006.01) | |
| *A61K 47/24* | (2006.01) | |
| *C07C 241/02* | (2006.01) | |

(52) U.S. Cl.
CPC ............ *C07C 243/38* (2013.01); *A01N 37/28* (2013.01); *A01N 37/40* (2013.01); *A61K 31/166* (2013.01); *A61K 47/10* (2013.01); *A61K 47/12* (2013.01); *A61K 47/22* (2013.01); *A61K 47/24* (2013.01); *C07C 241/02* (2013.01); *C07B 2200/07* (2013.01); *C07B 2200/13* (2013.01); *C12N 2710/10341* (2013.01); *C12N 2830/002* (2013.01); *Y02A 50/401* (2018.01); *Y02A 50/409* (2018.01); *Y02A 50/411* (2018.01); *Y02A 50/423* (2018.01); *Y02A 50/475* (2018.01); *Y10T 428/2982* (2015.01)

(58) Field of Classification Search
None
See application file for complete search history.

(56) References Cited

U.S. PATENT DOCUMENTS

| | | | |
|---|---|---|---|
| 7,304,161 B2 | 12/2007 | Hormann et al. | |
| 7,531,326 B2 | 5/2009 | Kapitskaya et al. | |
| 7,563,879 B2 | 7/2009 | Palli | |
| 7,563,928 B2 | 7/2009 | Hormann et al. | |
| 7,919,269 B2 | 4/2011 | Zhang et al. | |
| 7,935,510 B2 | 5/2011 | Palli et al. | |
| 8,076,517 B2 * | 12/2011 | Hormann | C07C 281/02 564/310 |
| 8,946,294 B2 | 2/2015 | Hormann et al. | |
| 9,604,913 B2 | 3/2017 | Hormann et al. | |
| 2002/0110861 A1 | 8/2002 | Dhadialla et al. | |
| 2006/0100416 A1 | 5/2006 | Palli et al. | |
| 2009/0123441 A1 | 5/2009 | Braughler et al. | |

OTHER PUBLICATIONS

Braga, D. et al., "Crystal Polymorphism and Multiple Crystal Forms," *Structure and Bonding 132*:25-50, Springer-Verlag Berlin Heidelberg (2009).
Lee, T. et al., "Solubility, Polymorphism, Crystallinity, and Crystal Habit of Acetaminophen and Ibuprofen by Initial Solvent Screening," *Pharmaceutical Technology 30*:72, Advanstar Communications, United States (Oct. 2, 2006).
Caira, M.R., "Crystalline Polymorphism of Organic Compounds," *Topics in Current Chemistry 198*: 163-208, Springer Verlag Berlin Heidelberg (1998).
Polymorphism in Pharmaceutical Solids, Second Edition, Brittain, H.G., ed., vol. 192, pp. 1-23 and 288-480, CRC Press, United States (2009).

* cited by examiner

*Primary Examiner* — Jared Barsky
(74) *Attorney, Agent, or Firm* — Sterne, Kessler, Goldstein & Fox P.L.L.C.

(57) ABSTRACT

The present disclosure provides crystalline polymorphic and amorphous forms of (R)-3,5-dimethyl-benzoic acid N-(1-tert-butyl-butyl)-N'-(2-ethyl-3-methoxy-benzoyl)-hydrazide (Compound 1) or (S)-3,5-dimethyl-benzoic acid N-(1-tert-butyl-butyl)-N'-(2-ethyl-3-methoxy-benzoyl)-hydrazide (Compound 2). The present disclosure further provides compositions comprising crystalline polymorphic and amorphous forms of Compound 1 or Compound 2 and an excipient, methods of making crystalline polymorphic or amorphous forms of Compound 1 or Compound 2, and methods of using crystalline polymorphic or amorphous forms of Compound 1 or Compound 2 to regulate gene expression in a cell or in a subject.

9 Claims, 32 Drawing Sheets
Specification includes a Sequence Listing.

CRYSTALLINE DIACYLHYDRAZINE AND THE USE THEREOF

BACKGROUND OF THE INVENTION (R)-3,5-dimethyl-benzoic acid N-(1-tert-butyl-butyl)-N'-(2-ethyl-3-methoxy-benzoyl)-hydrazide (referred to herein as "Compound 1") is a diacylhydrazine ligand used in ecdysone receptor-based inducible gene expression systems to regulate in vitro and in vivo gene expression, and treat diseases such as cancer.

US 2009/0163592 A1 discloses Compound 1, methods of making Compound 1, compositions comprising Compound 1, and methods of using Compound 1 to modulate in vitro or in vivo therapeutic gene expression in a host cell. For example, murine IL-12 expression, under the control of the RheoSwitch Therapeutic System® (RTS®) technology, is induced by administration of Compound 1 to mice. US 2009/0163592 A1 also discloses (S)-3,5-dimethyl-benzoic acid N-(l-tert-butyl-butyl)-N'-(2-ethyl-3-methoxy-benzoyl)-hydrazide (referred to herein as "Compound 2").

BRIEF SUMMARY OF THE INVENTION

There exists a need for stable crystalline polymorphic forms of Compound 1 or Compound 2, and methods to reproducibly make them, for use in regulating gene expression in ecdysone receptor-based inducible gene expression systems. The present disclosure provides crystalline polymorphic forms of Compound 1 or Compound 2, including anhydrous, hydrated, and solvated forms. The present disclosure also provides amorphous forms of Compound 1 or Compound 2.

In another aspect, the present disclosure provides methods of making crystalline polymorphic forms or amorphous forms of Compound 1 or Compound 2.

In another aspect, the present disclosure provides compositions comprising one or more crystalline polymorphic forms or amorphous forms of Compound 1 or Compound 2 and one or more excipients.

In another aspect, the present disclosure provides methods of making compositions comprising one or more crystalline polymorphic forms or amorphous forms of Compound 1 or Compound 2 and one or more excipients.

In another aspect, the present disclosure provides in vitro methods of regulating gene expression in a host cell, comprising contacting the cell with one or more crystalline polymorphic forms or amorphous forms of Compound 1 or Compound 2, or a composition comprising one or more crystalline polymorphic forms or amorphous forms of Compound 1 or Compound 2 and one or more excipients.

In another aspect, the present disclosure provides in vivo methods of regulating gene expression in a subject for the treatment of disease, comprising administering to the subject one or more crystalline polymorphic forms or amorphous forms of Compound 1 or Compound 2, or a pharmaceutically acceptable composition comprising one or more crystalline polymorphic forms or amorphous forms of Compound 1 or Compound 2 and one or more pharmaceutically acceptable excipients.

In another aspect, the present disclosure provides methods of controlling insects, comprising contacting insects or their habitat with one or more crystalline polymorphic forms or amorphous forms of Compound 1 or Compound 2, or a composition thereof.

In another aspect, the present disclosure provides kits comprising one or more crystalline polymorphic forms or amorphous forms of Compound 1 or Compound 2, or a composition thereof.

DETAILED DESCRIPTION OF THE INVENTION

Figure 1:
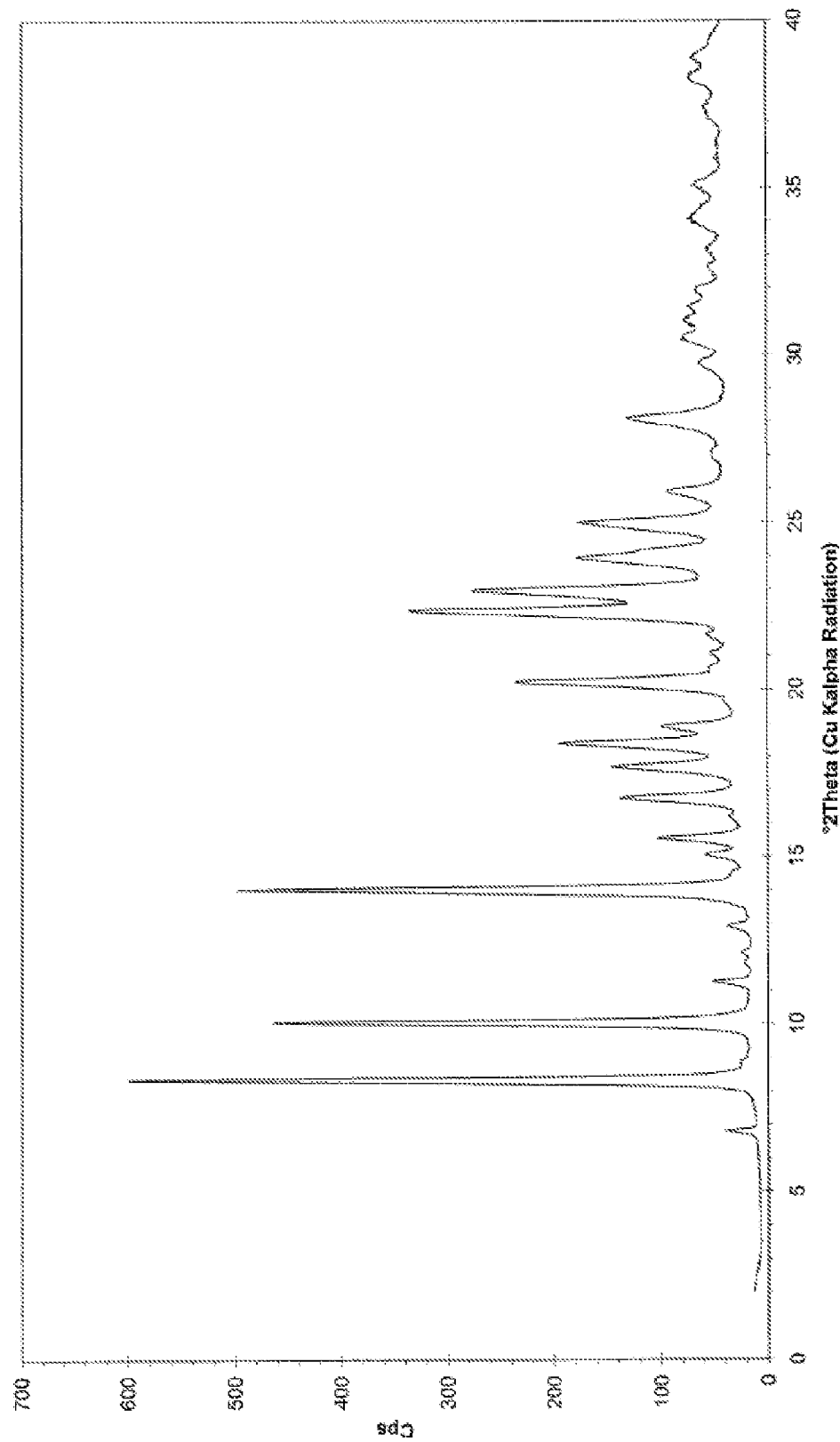
FIG. 1 is a PXRD diffractogram of Form I-A of Compound 1.

In one aspect, the present disclosure provides crystalline polymorphic forms of Compound 1, or mixtures thereof, or crystalline polymorphic forms of Compound 2, or mixtures thereof.

In another aspect, the present disclosure provides Compound 1 comprising Form II, Form III, Form IV, Form V, Form VI, Form VII, Form VIII, or Form IX, or a mixture thereof, or Compound 2 comprising Form II, Form III, Form IV, Form V, Form VI, Form VII, Form VIII, or Form IX, or a mixture thereof.

In another aspect, the present disclosure provides Compound 1 consisting essentially of Form II, Form III, Form IV, Form V, Form VI, Form VII, Form VIII, or Form IX, or Compound 2 consisting essentially of Form II, Form III, Form IV, Form V, Form VI, Form VII, Form VIII, or Form IX.

In another aspect, the present disclosure provides Compound 1 consisting of Form II, Form III, Form IV, Form V, Form VI, Form VII, Form VIII, or Form IX, or Compound 2 consisting of Form II, Form III, Form IV, Form V, Form VI, Form VII, Form VIII, or Form IX.

In another aspect, the present disclosure provides Compound 1 comprising Form III, Form IV, Form V, Form VI, Form VII, Form VIII, or Form IX, or a mixture thereof, or Compound 2 comprising Form III, Form IV, Form V, Form VI, Form VII, Form VIII, or Form IX, or a mixture thereof.

In another aspect, the present disclosure provides Compound 1 comprising Form II, Form III, or Form IV, or a mixture thereof, or Compound 2 comprising Form II, Form III, or Form IV, or a mixture thereof.

In another aspect, the present disclosure provides Compound 1 comprising Form III, or Form IV, or a mixture thereof, or Compound 2 comprising Form III, or Form IV, or a mixture thereof.

In another aspect, the present disclosure provides Compound 1 Form II or Compound 2 Form II. In one embodiment, Form II is characterized as having a powder x-ray diffraction (PXRD) pattern with peaks at 8.34, 10.06, 14.01, 16.77, 17.70, 18.40, 20.23, 22.36, 22.97, and 25.00 degrees 2Θ. In another embodiment, Compound 1 Form II is characterized as having a PXRD pattern with peaks at 8.34, 10.06, 14.01, 14.51, 15.55, 16.77, 17.70, 18.40, 18.88, 20.23, 22.36, 22.97, 23.91, 24.15, 25.00, 25.92, 26.96, 28.09, 28.33, 29.84, 30.52, 31.05, 31.45, 31.97, 32.61, 33.17, 34.02, 34.45, and 35.07 degrees 2Θ. In another embodiment, Form II is characterized as having a PXRD pattern that is essentially the same as FIG. 11. In another embodiment, Form II is characterized as having a FT-Raman spectrum with peaks at 3007, 2920, 2869, 1696, 1629, 1605, 1449, 1381, 1351, 1275, 1194, 1086, 1064, 1000, 931, 780, 544, 517, 225, 164 cm$^1$. In another embodiment, Form II is characterized as having a FT-Raman spectrum essentially the same a FIG. 12. In another embodiment, the present disclosure provides substantially pure Form II. In another embodiment, the present disclosure provides pure Form II. In another embodiment, the present disclosure provides pure Compound 1 Form II.

In another aspect, the present disclosure provides Compound 1 Form III or Compound 2 Form III. In one embodiment, Form III is characterized as having a powder x-ray diffraction (PXRD) pattern with peaks at 8.14, 8.52, 17.00, 18.56, and 22.19 degrees 2Θ. In another embodiment, Form III is characterized as having a PXRD pattern with peaks at 8.14, 8.52, 9.62, 11.02, 11.90, 12.16, 14.02, 14.62, 17.00, 17.88, 18.56, 19.02, 19.24, 20.51, 20.93, 22.19, 22.73, 23.22, 24.31, 24.53, 25.91, 26.22, 27.36, 27.73, 28.70, 30.84, 31.52, 32.30, 33.19, and 34.39 degrees 2Θ. In another embodiment, Form III is characterized as having a PXRD pattern that is essentially the same as FIG. 14. In another embodiment, Form III is characterized as having an FT-Raman spectrum with peaks at 2922, 2873, 2837, 1699, 1628, 1602, 1449, 1379, 1274, 1090, 1065, 998, 778, 637, 549, 515, 320, 225, 165, and 127 cm$^1$. In another embodiment, Form III is characterized as having an FT-Raman spectrum essentially the same a FIG. 15. In another embodiment, the present disclosure provides substantially pure Form III. In another embodiment, the present disclosure provides pure Form III. In another embodiment, the present disclosure provides pure Compound 1 Form III.

Figure 17:
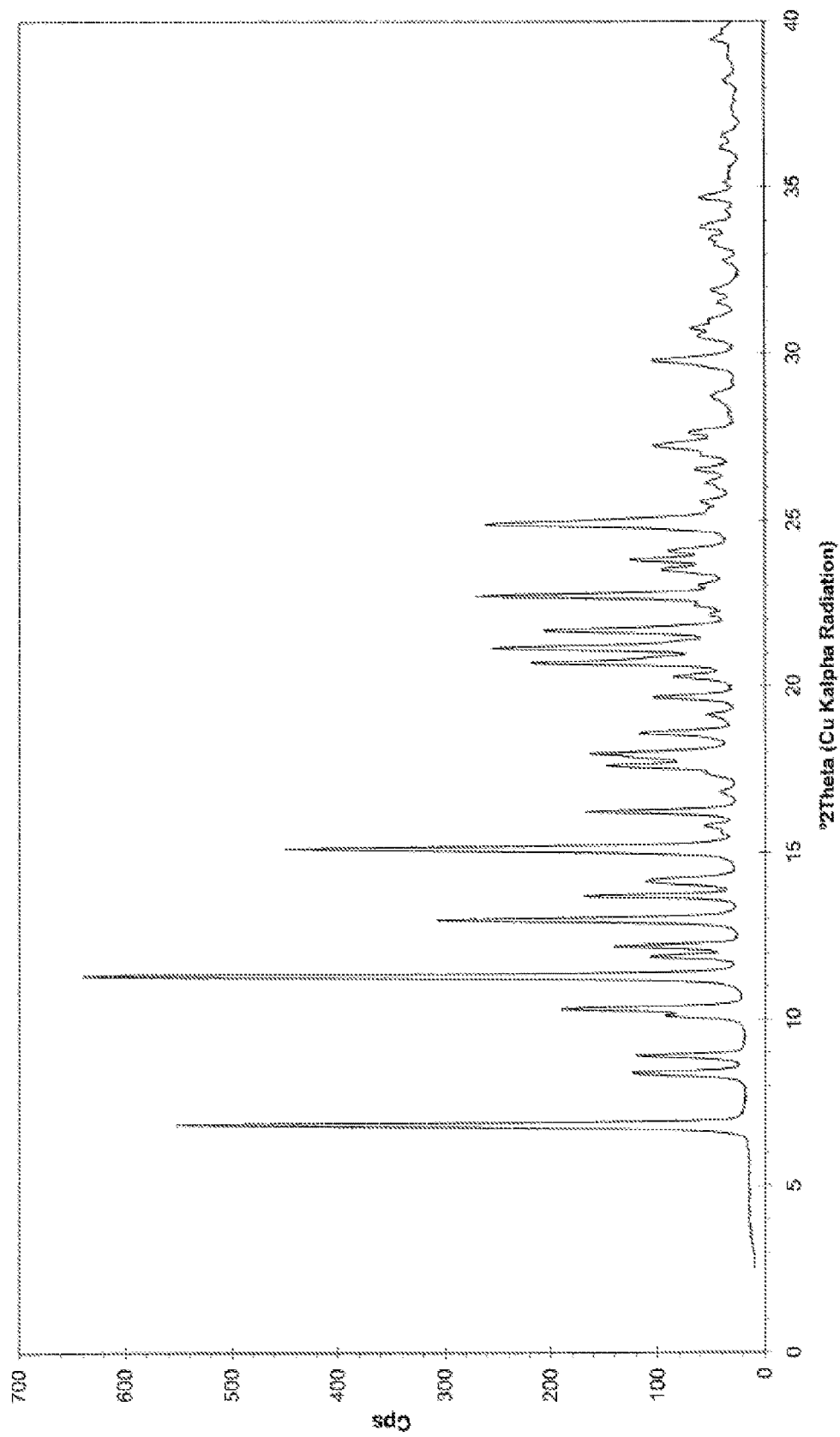
FIG. 17 is a PXRD diffractogram of pure Form IV of Compound 1.
Figure 18:
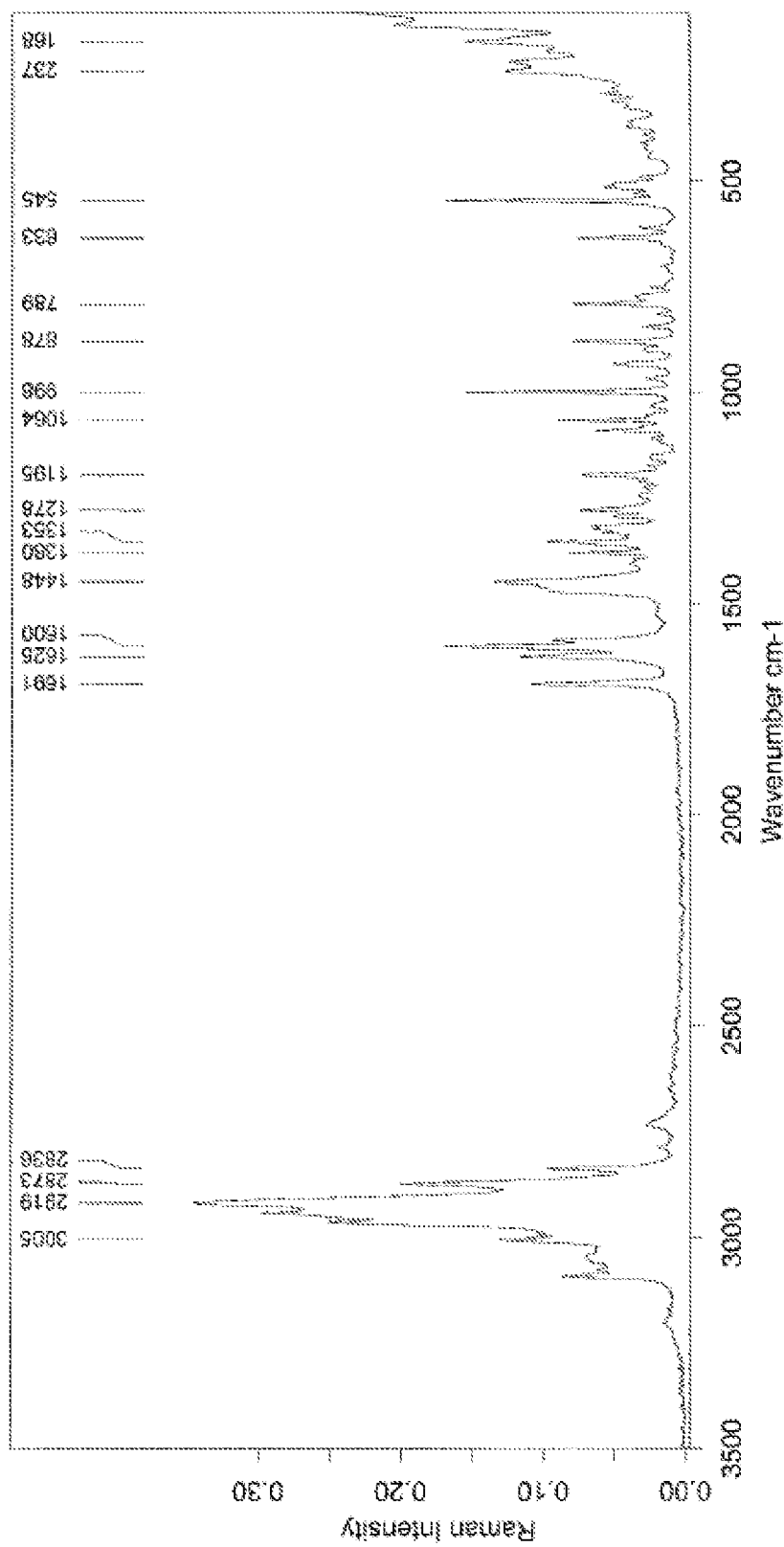
FIG. 18 is a FT-Raman spectrum of pure Form IV of Compound 1.
Figure 19:
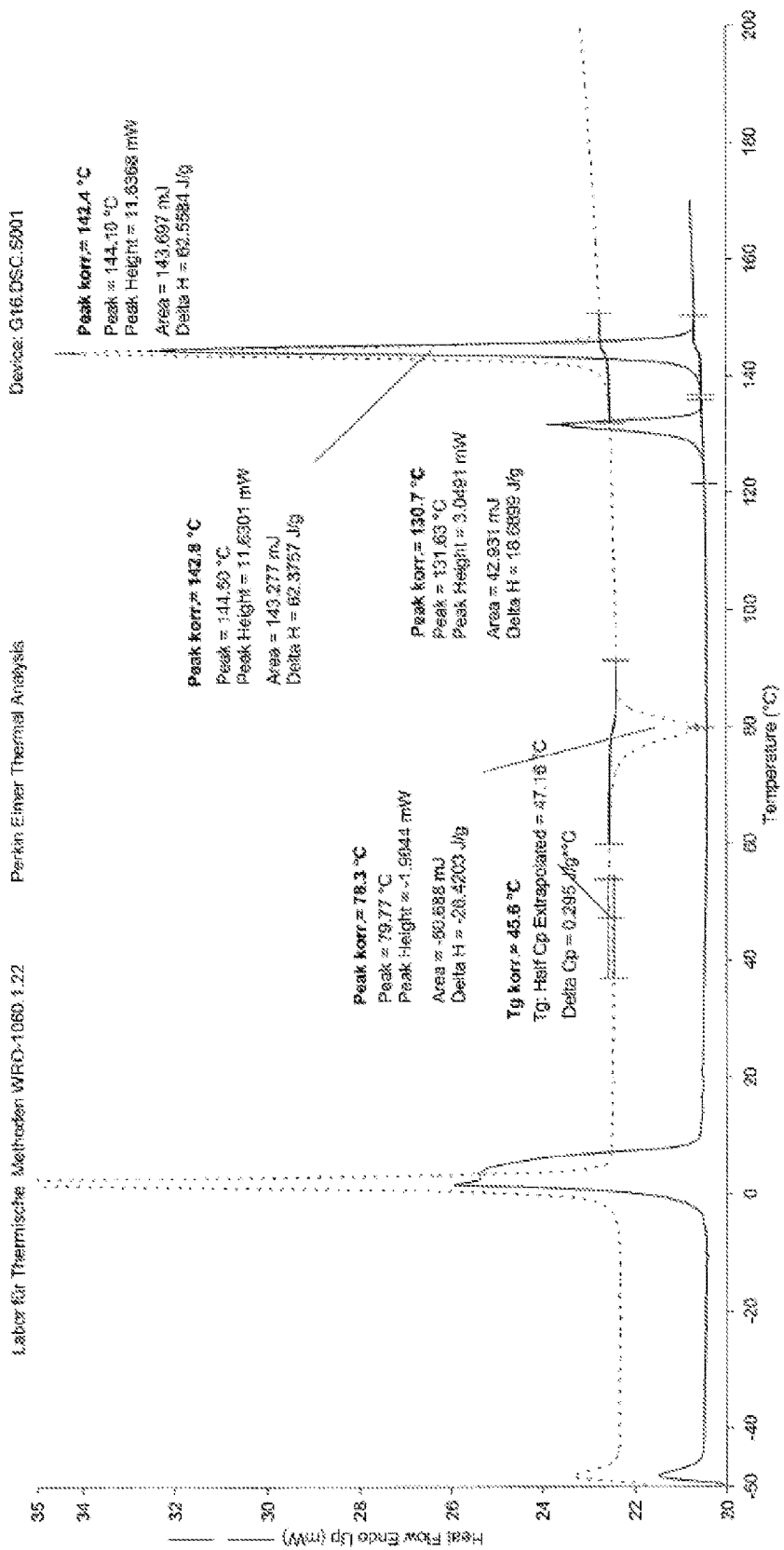
FIG. 19 is a DCS thermogram of pure Form IV of Compound 1.
Figure 20:
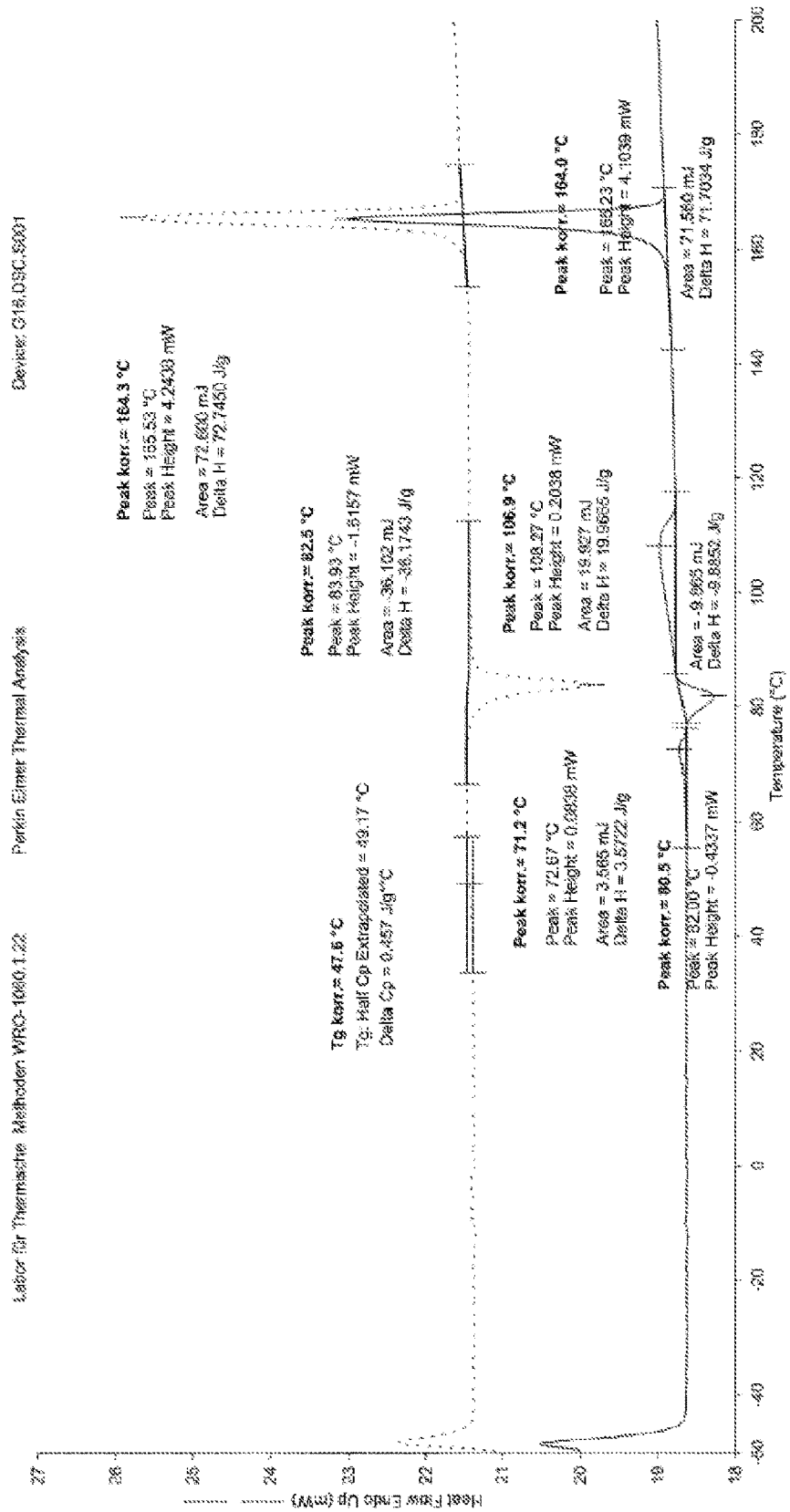
FIG. 20 is a DCS thermogram of pure Form IV (dried) of Compound 1.

In another aspect, the present disclosure provides Compound 1 Form IV or Compound 2 Form IV. In one embodiment, Form IV is characterized as having a powder x-ray diffraction (PXRD) pattern with peaks at 6.83, 10.31, 11.30, 12.18, 12.98, 13.69, 15.11, 16.23, 17.60, 17.99, 20.70, 21.15, 21.68, 22.71, 23.79, and 24.86 degrees 2Θ. In another embodiment, Form IV is characterized as having a PXRD pattern with peaks at 6.83, 8.38, 8.91, 10.11, 10.31, 11.30, 11.89, 12.18, 12.98, 13.69, 14.14, 15.11, 15.81, 16.23, 17.60, 17.99, 18.60, 19.15, 19.66, 20.28, 20.70, 21.15, 21.68, 22.44, 22.71, 23.50, 23.79, 24.06, 24.86, 25.55, 26.53, 26.94, 27.21, 27.60, 28.67, 29.79, 30.50, 30.75, 31.55, 31.89, 32.78, 33.25, 33.48, 33.81, and 34.68 degrees 2Θ. In another embodiment, Form IV is characterized as having a PXRD pattern that is essentially the same as FIG. 17. In another embodiment, Form IV is characterized as having a FT-Raman spectrum with peaks at 3005, 2919, 2873, 2836, 1691, 1625, 1600, 1448, 1380, 1353, 1278, 1195, 1064, 998, 878, 789, 633, 545, 237, and 168 cm$^1$. In another embodiment, Form IV is characterized as having a FT-Raman spectrum essentially the same a FIG. 18. In another embodiment, the present disclosure provides substantially pure Form IV. In another embodiment, the present disclosure provides pure Form IV. In another embodiment, the present disclosure provides pure Compound 1 Form IV.

In another aspect, the present disclosure provides Compound 1 Form V or Compound 2 Form V. In one embodiment, Form V is characterized as having a powder x-ray diffraction (PXRD) pattern with peaks at 9.38, 12.22, 13.18, 14.98, 17.32, 18.40, 22.41, 23.40, 23.55, 24.63, 24.79, 25.61, 28.02, and 31.77 degrees 2Θ. In another embodiment, Form V is characterized as having a PXRD pattern with peaks at 6.11, 9.38, 11.13, 12.22, 13.18, 14.14, 14.98, 15.52, 15.78, 17.32, 18.40, 18.75, 19.48, 19.74, 20.63, 21.33, 21.88, 22.41, 23.40, 23.55, 23.76, 24.27, 24.63, 24.79, 25.61, 26.66, 27.10, 27.81, 28.02, 28.58, 29.91, 30.35, 30.95, 31.32, 31.77, 32.77, 33.81, and 34.98 degrees 2Θ. In another embodiment, Form V is characterized as having a PXRD pattern that is essentially the same as FIG. 21. In another embodiment, Form V is characterized as having a FT-Raman spectrum with peaks at 3010, 2963, 2938, 2872, 2836, 1690, 1624, 1597, 1452, 1359, 1317, 1275, 1193, 1062, 999, 877, 788, 546, 516, and 168 cm$^{-1}$. In another embodiment, Form V is characterized as having an FT-Raman spectrum essentially the same a FIG. 22. In another embodiment, the present disclosure provides substantially pure Form V. In another embodiment, the present disclosure provides pure Form V. In another embodiment, the present disclosure provides pure Compound 1 Form V.

In another aspect, the present disclosure provides Compound 1 Form VI or Compound 2 Form VI. In one embodiment, Form VI is characterized as having a powder x-ray diffraction (PXRD) pattern with peaks at 9.38, 12.23, 13.25, 17.48, 18.41, and 22.41 degrees 2Θ. In another embodiment, Form VI is characterized as having a PXRD pattern with peaks at 6.09, 6.82, 8.57, 9.38, 11.26, 12.23, 13.25, 14.27, 15.05, 15.54, 15.95, 17.48, 18.41, 18.79, 19.54, 19.76, 20.79, 21.48, 22.02, 22.41, 23.42, 24.07, 24.34, 24.64, 24.83, 25.34, 25.67, 26.74, 26.87, 27.24, 27.99, 28.56, 28.93, 29.47, 30.04, 30.98, 31.75, 32.34, 32.96, and 33.84 degrees 2Θ. In another embodiment, Form VI is characterized as having a PXRD pattern that is essentially the same as FIG. 23. In another embodiment, Form VI is characterized as having a FT-Raman spectrum with peaks at 3010, 2963, 2938, 2917, 2873, 2836, 1692, 1626, 1598, 1453, 1381, 1357, 1317, 1275, 1194, 999, 878, 788, 545, and 167 cm$^1$. In another embodiment, Form VI is characterized as having an FT-Raman spectrum essentially the same a FIG. 24. In another embodiment, the present disclosure provides substantially pure Form VI. In another embodiment, the present disclosure provides pure Form VI. In another embodiment, the present disclosure provides pure Compound 1 Form VI.

Figure 25:
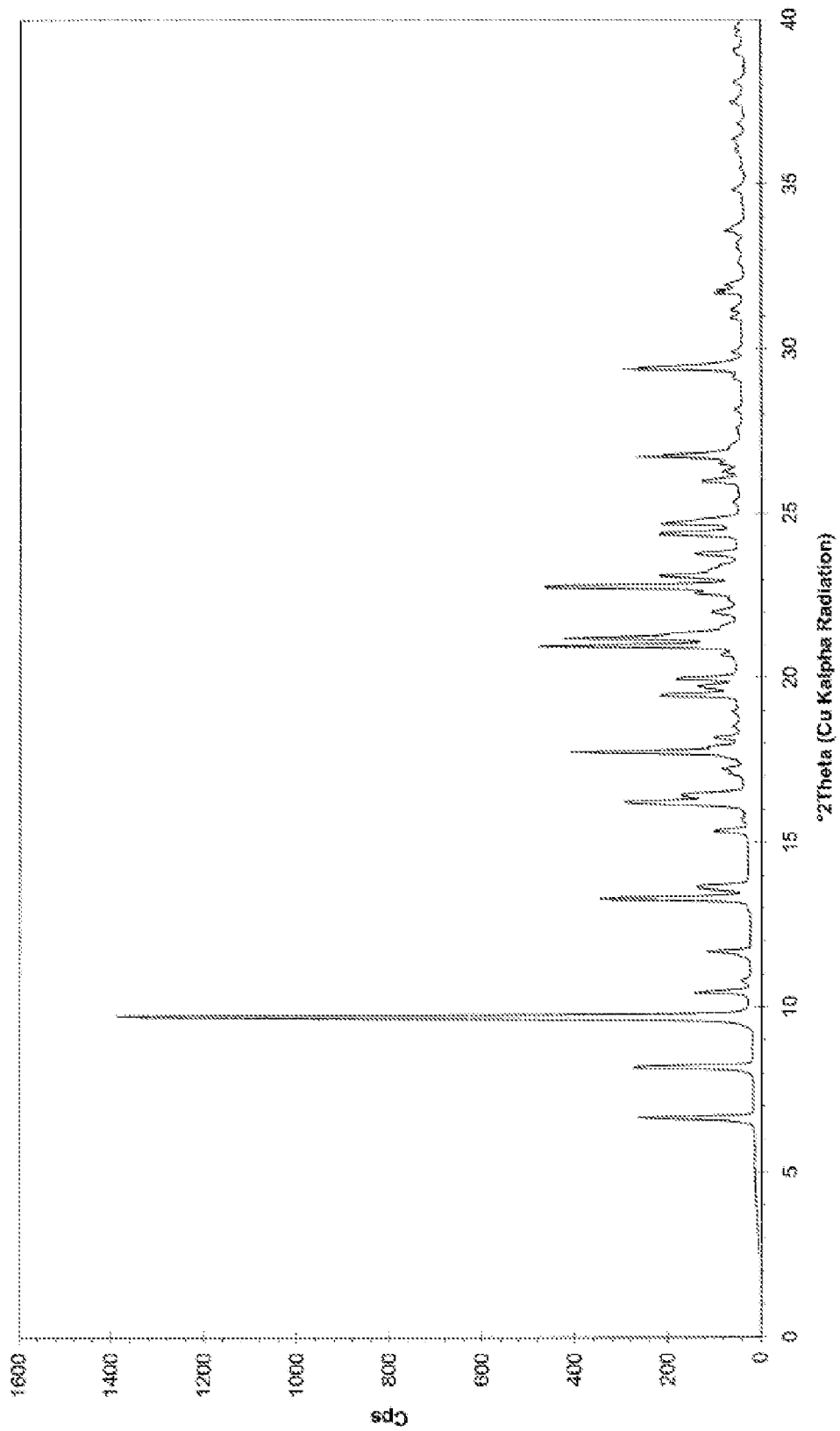
FIG. 25 is a PXRD diffractogram of pure Form VII of Compound 1.
Figure 26:
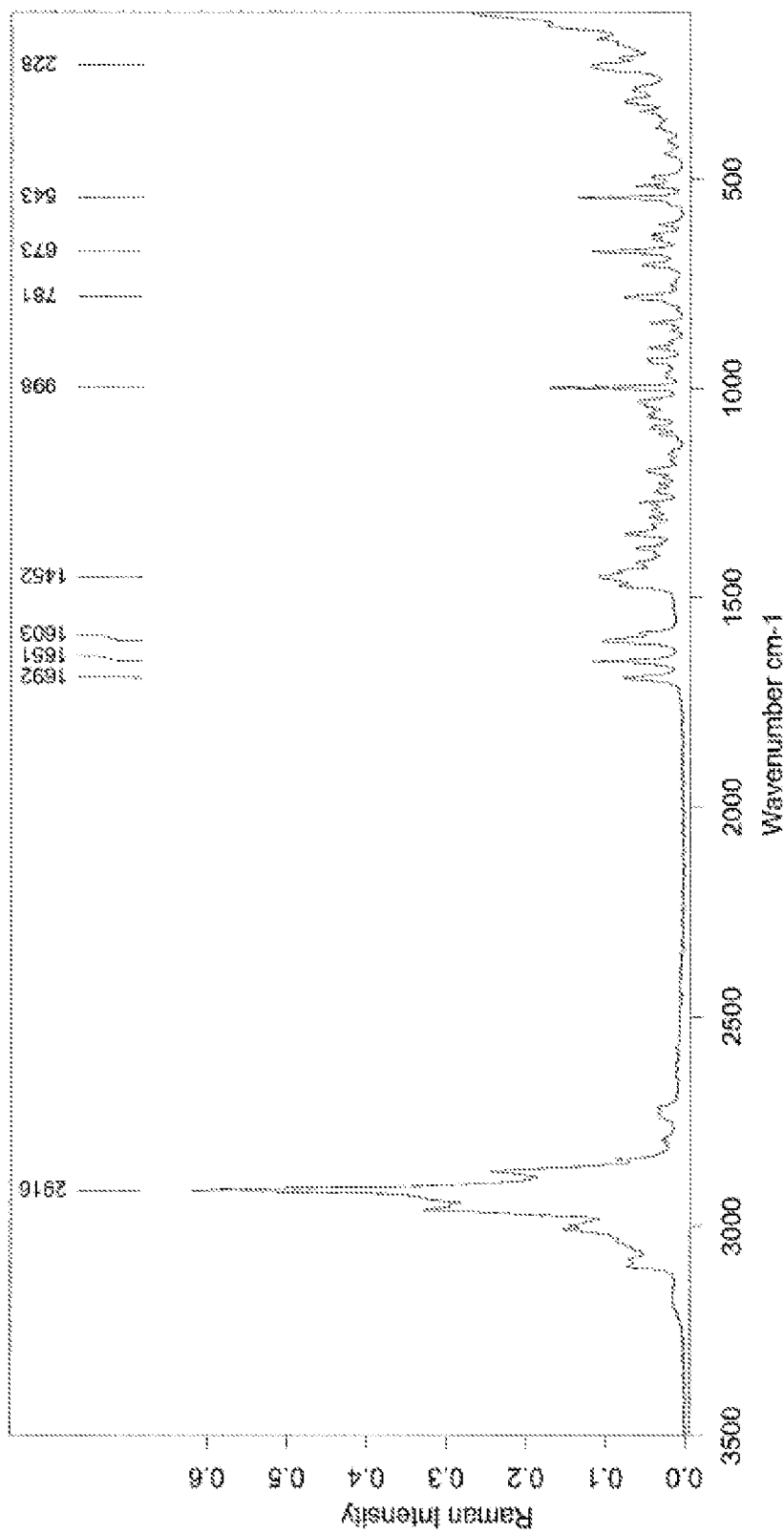
FIG. 26 is a FT-Raman spectrum of pure Form VII of Compound 1.

In another aspect, the present disclosure provides Compound 1 Form VII or Compound 2 Form VII. In one embodiment, Form VII is characterized as having a powder x-ray diffraction (PXRD) pattern with peaks at 8.18, 9.71, 13.30, 16.22, 17.73, 20.98, 21.20, 22.76, 24.68, 26.72, and 29.39 degrees 2Θ. In another embodiment, Form VII is characterized as having a PXRD pattern with peaks at 6.64, 8.18, 9.71, 10.44, 10.80, 11.69, 13.30, 13.64, 15.35, 16.22, 16.44, 17.23, 17.73, 18.16, 19.46, 19.72, 19.97, 20.70, 20.98, 21.20, 21.52, 21.98, 22.57, 22.76, 23.09, 23.75, 24.37, 24.68, 25.31, 25.97, 26.25, 26.49, 26.72, 28.13, 29.39, 29.88, 30.92, 31.17, 31.70, 31.96, 33.57, and 34.83 degrees 2Θ. In another embodiment, Form VII is characterized as having a PXRD pattern that is essentially the same as FIG. 25. In another embodiment, Form VII is characterized as having a FT-Raman spectrum with peaks at 2916, 1692, 1651, 1603, 1452, 998, 781, 673, 543, and 228 cm$^1$. In another embodiment, Form VII is characterized as having a FT-Raman spectrum essentially the same a FIG. 26. In another embodiment, the present disclosure provides substantially pure Form VII. In another embodiment, the present disclosure provides pure Form VII. In another embodiment, the present disclosure provides pure Compound 1 Form VII.

In another aspect, the present disclosure provides Compound 1 Form VIII or Compound 2 Form VIII. In one embodiment, Form VIII is characterized as having a powder x-ray diffraction (PXRD) pattern with peaks at 10.05, 10.77, 14.06, 16.76, 18.11, 18.32, 18.43, 20.89, 21.71, 21.87, 24.07, 24.90, and 28.71 degrees 2Θ. In another embodiment, Form VIII is characterized as having a PXRD pattern with peaks at 7.48, 8.31, 10.05, 10.77, 12.27, 13.65, 14.06, 15.60, 16.03, 16.76, 16.96, 17.16, 18.11, 18.32, 18.43, 18.65, 19.89, 20.28, 20.89, 21.71, 21.87, 24.07, 24.90, 25.28, 25.54, 25.86, 26.22, 26.66, 27.74, 28.44, 28.71, 29.08, 30.26, 31.16, 32.59, 32.85, 34.01, 34.68, and 35.09 degrees 2Θ. In another embodiment, Form VIII is characterized as having a PXRD pattern that is essentially the same as FIG. 27. In another embodiment, Form VIII is characterized as having a FT-Raman spectrum with peaks at 3056, 2921, 2874, 1690, 1634, 1601, 1447, 1278, 1206, 1157, 1091, 1069, 1002, 877, 793, 621, 542, 515, 370, and 105 cm$^1$. In another embodiment, Form VIII is characterized as having an FT-Raman spectrum essentially the same a FIG. 28. In another embodiment, the present disclosure provides substantially pure Form VIII. In another embodiment, the present disclosure provides pure Form VIII. In another embodiment, the present disclosure provides pure Compound 1 Form VIII.

In another aspect, the present disclosure provides Compound 1 Form IX or Compound 2 Form IX. In one embodiment, Form IX is characterized as having a powder x-ray diffraction (PXRD) pattern with peaks at 7.06, 15.74, and 18.71 degrees 2Θ. In another embodiment, Form IX is characterized as having a PXRD pattern with peaks at 7.06, 9.93, 12.22, 14.13, 15.74, 17.28, 18.71, 19.96, 21.18, 22.39, 23.51, 24.54, 25.58, 27.52, 28.48, 29.33, 30.18, 31.01, 31.82, and 32.73 degrees 2Θ. In another embodiment, Form IX is characterized as having a PXRD pattern that is essentially the same as FIG. 29. In another embodiment, Form IX is characterized as having a FT-Raman spectrum with peaks 2921, 2870, 1696, 1632, 1602, 1449, 1381, 1350, 1275, 1064, 1000, 932, 780, 544, 516, 225, and 164 cm$^1$. In another embodiment, Form IX is characterized as having an FT-Raman spectrum essentially the same a FIG. 30. In another embodiment, the present disclosure provides substantially pure Form IX. In another embodiment, the present disclosure provides pure Form IX. In another embodiment, the present disclosure provides pure Compound 1 Form IX.

Figure 31:
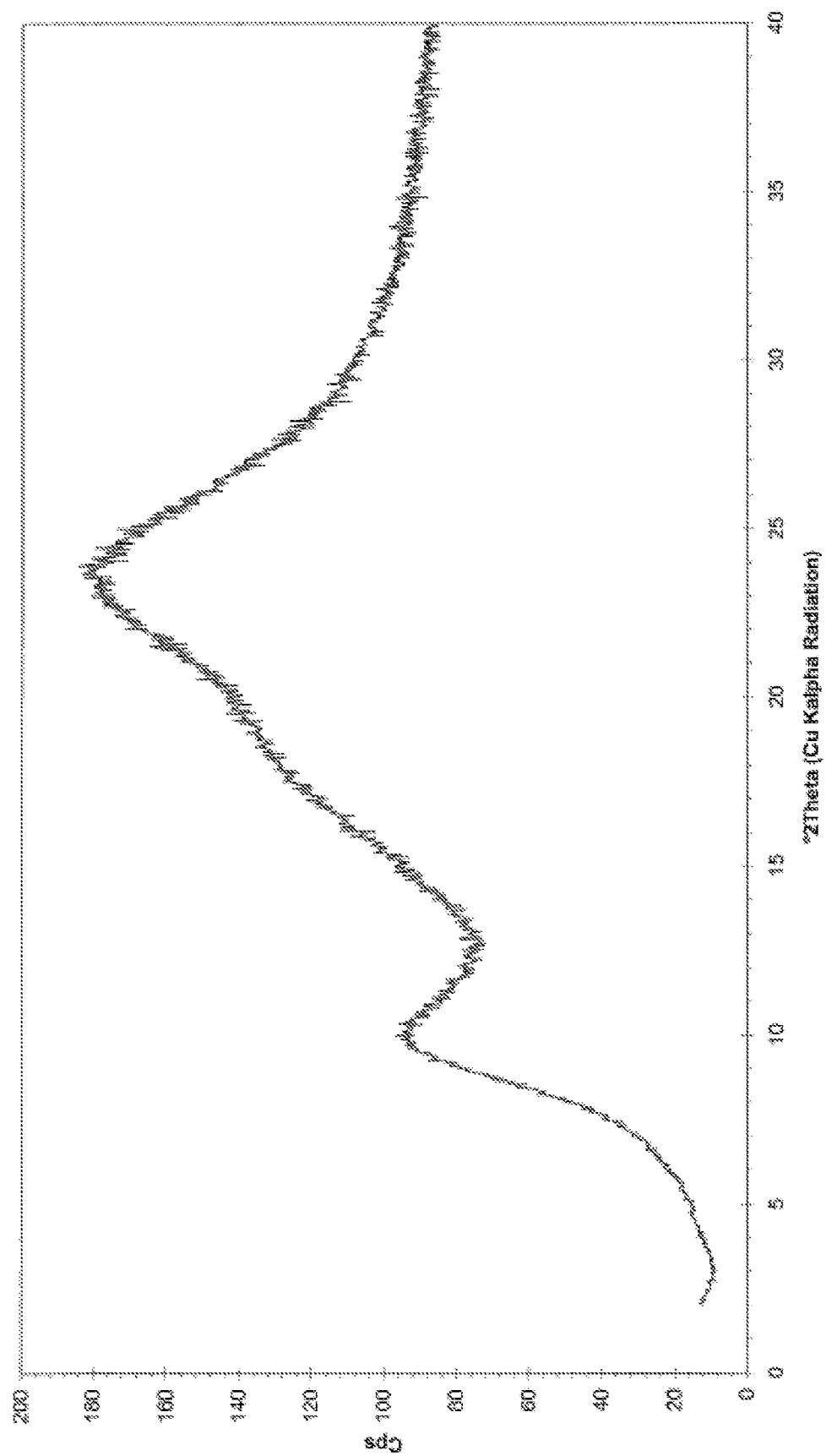
FIG. 31 is a PXRD diffractogram of Form X of Compound 1.

In another aspect, the present disclosure provides Compound 1 Form X or Compound 2 Form X. Form X is an amorphous form of Compound 1 or Compound 2. In one embodiment, Form X is characterized as having a PXRD pattern that is essentially the same as FIG. 31. In another embodiment, Form X is characterized as having an FT-Raman spectrum essentially the same as FIG. 32. In another embodiment, the present disclosure provides substantially pure Form X. In another embodiment, the disclosure provides pure Form X. In another embodiment, the present disclosure provides pure Compound 1 in amorphous form.

In another aspect, the present disclosure provides micronized crystalline polymorphic forms or amorphous forms of Compound 1, or micronized crystalline polymorphic forms or amorphous forms of Compound 2. In one embodiment, the average particle size distribution of the micronized form of Compound 1 or Compound 2 is about 20 µm or less, e.g., about 19 µm, about 18 µm, about 17 µm, about 16 µm, about 15 µm, about 14 µm, about 13 µm, about 12 µm, or about 11 µm, or less. In another embodiment, the average particle size distribution is about 10 µm or less, e.g., about 9 µm, about 8 µm, about 7 µm, about 6 m, or about 5 m, or less. In another embodiment, the average particle size distribution is about 5 µm or less, e.g., about 4 µm, about 3 µm, about 2 m, or about 1 µm, or less. In another embodiment, the average particle size distribution is about 1 µm or less, e.g., about 0.9 µm, about 0.8 m, about 0.7 µm, about 0.6 µm, about 0.5 µm, about 0.4 µm, about 0.3 µm, about 0.2 µm, about 0.1 µm, about 0.09 µm, about 0.08 µm, about 0.07 µm, about 0.06 m, about 0.05 µm, about 0.04 µm, about 0.03 µm, about 0.02 µm, or about 0.01 µm or less. In another embodiment, the present disclosure provides micronized crystalline Compound 1 Form III having an average particle size of about 20 µm or less, e.g., about 19 µm, about 18 µm, about 17 µm, about 16 µm, about 15 µm, about 14 m, about 13 µm, about 12 µm, about 11 µm, about 10 µm, about 9 µm, about 8 µm, about 7 µm, about 6 µm, about 5 µm, about 4 µm, about 3 µm, about 2 µm, about 1 m, about 0.9 µm, about 0.8 µm, about 0.7 µm, about 0.6 µm, about 0.5 µm, about 0.4 m, about 0.3 µm, about 0.2 µm, about 0.1 µm, about 0.09 µm, about 0.08 µm, about 0.07 m, about 0.06 µm, about 0.05 µm, about 0.04 µm, about 0.03 µm, about 0.02 m, or about 0.01 m, or less. In another embodiment, the present disclosure provides micronized amorphous Compound 1 Form X having an average particle size of about 20 µm or less, e.g., about 19 µm, about 18 µm, about 17 µm, about 16 µm, about 15 m, about 14 µm, about 13 µm, about 12 µm, about 11 µm, about 10 µm, about 9 µm, about 8 µm, about 7 µm, about 6 µm, about 5 µm, about 4 µm, about 3 µm, about 2 m, about 1 µm, about 0.9 µm, about 0.8 µm, about 0.7 µm, about 0.6 µm, about 0.5 m, about 0.4 µm, about 0.3 µm, about 0.2 µm, about 0.1 µm, about 0.09 µm, about 0.08 µm, about 0.07 µm, about 0.06 µm, about 0.05 µm, about 0.04 µm, about 0.03 m, about 0.02 m, or about 0.01 µm, or less.

In another aspect, the present disclosure provides methods of making crystalline polymorphic forms or amorphous forms of Compound 1 or crystalline polymorphic forms or amorphous forms of Compound 2. Methods of making crystalline polymorphic forms or amorphous forms of Compound 1 are described in the Examples provided herein below. Other methods used to make crystalline polymorphic forms of Compound 1 include sublimation and pressurization, e.g., under $CO_2$ (*J. Am. Chem. Soc.* 133:1399 (2011)). Similar methods can be used to make crystalline polymorphic forms or amorphous forms of Compound 2.

In one embodiment, a suspension of one or more crystalline polymorphic forms or amorphous forms of Compound 1 is equilibrated in one or more non-solvate forming solvents, and isolated, e.g., by filtration or centrifugation, to give substantially pure Form III. In another embodiment, a suspension of one or more crystalline polymorphic forms or amorphous forms of Compound 1 is equilibrated in one or more non-solvate forming solvents, and isolated to give pure Form III. In another embodiment, the equilibration of one or more crystalline polymorphic forms or amorphous forms of Compound 1 is repeated more than once, e.g., two, three, four, or five times, or more, to give pure Form III. In another embodiment, the suspension of one or more crystalline polymorphic forms or amorphous forms of Compound 1 is equilibrated for a period of time, e.g., about 15 minutes to about 24 hours, about 1 hour to about 8 hours, or about 1 hour to about 4 hours. In another embodiment, the suspension of one or more crystalline polymorphic forms or amorphous forms of Compound 1 is equilibrated for about 15 minutes, about 30 minutes, about 1 hour, about 2 hours, about 3 hours, about 4 hours, about 5 hours, about 6 hours, about 7, hours, about 8 hours, about 9 hours, about 10 hours, about 12 hours, about 15 hours, about 18 hours, about 20 hours, about 21 hours, about 1 day, about 2 days, about 3 days, about 4 days, about 5 days, about 6 days, about 1 week, about 2 weeks, about 3 weeks, about a month, or longer, until complete conversion to Form III is observed. In another embodiment, the suspension of one or more crystalline polymorphic forms or amorphous forms of Compound 1 is equilibrated at about 45° C. to about 5° C., e.g., about 45° C. to about 20° C. or about 35° C. to about 25° C. In another embodiment, the suspension of one or more crystalline polymorphic forms or amorphous forms of Compound 1 is equilibrated at about 45° C. or less, e.g., at about 44° C., about 43° C., about 42° C., about 41° C., about 40° C., about 39° C., about 38°, about 37° C., about 36° C., about 35° C., about 34° C., about 33° C., about 32° C., about 31° C., about 30° C., about 29° C., about 28° C., about 27° C., about 26° C. (i.e., about room temperature), about 25° C., about 24° C., about 23° C., about 22° C., about 21° C., about 20° C., about 19° C., about 18° C., about 17° C., about 16° C., about 15° C., about 14° C., about 13° C., about 12° C., about 11° C., about 10° C., about 9° C., about 8° C., about 7° C., about 6° C., about 5° C., about 4° C., about 3° C., about 2° C., about 1° C., or about 0° C., or less. In another embodiment, the suspension of one or more crystalline polymorphic forms or amorphous forms of Compound 1 is equilibrated at about room temperature, or less. In another embodiment, the one or more non-solvate forming solvents are n-heptane, cumeme, diethyl ether, toluene, ethyl acetate, tert-butyl methyl ether, or n-dodecane. In another embodiment, the one or more non-solvate forming solvents are n-heptane, toluene, ethanol, or isopropanol. If two non-solvate forming solvents, e.g., heptane/toluene, are used, the ratio of solvents is about 50:1, e.g., about 25:1, about 20:1; about 10:1, about 9:1, about 8:1, about 7:1; about 6:1; about 5:1, about 4:1, about 3:1, about 2:1, or about 1:1.

In another embodiment, a suspension of one or more crystalline polymorphic forms of Compound 1 is equilibrated in heptane/toluene, and isolated to give substantially pure Form III. In another embodiment, a suspension of one or more crystalline polymorphic forms of Compound 1 is equilibrated in heptane/toluene, and isolated to give pure Form III. In another embodiment, the ratio of heptane:toluene is about 10:1 to about 1:10, e.g., about 5:1 to about 1:5, about 3:1 to about 1:3, or about 2:3 to about 3:2. In another embodiment, the ratio of heptane:toluene is about 10:1, about 9:1, about 8:1, about 7:1, about 6:1, about 5:1, about 4:1, about 3:1, about 2:1, about 1:1, about 1:2, about 1:3, about 2:3, about 1:4, about 1:5, about 1:6, about 1:7, about 1:8, about 1:9, or about 1:10. In another embodiment, the ratio of heptane:toluene is about 9:1. In another embodiment, the ratio of heptane:toluene is about 2:3. In another embodiment, the suspension in heptane/toluene is equilibrated at about 25° C. In another embodiment, the suspension in heptane/toluene is equilibrated at about 5° C. In another embodiment, the suspension in heptane/toluene is equilibrated for about 2, about 3, about 4, or about 5 hours. In another embodiment, the suspension in heptane/toluene is equilibrated for about 20 hours. In another embodiment, a suspension of one or more crystalline polymorphic forms of Compound 1 is equilibrated in heptane/toluene, isolated, re-equilibrated in heptane/toluene, or in another non-solvate forming solvent or mixture of non-solvate forming solvents, and re-isolated to give pure Form III.

In another embodiment, a suspension of one or more crystalline polymorphic forms of Compound 1 is equilibrated in heptane/isopropanol or in heptane/ethanol, and isolated to give substantially pure Form III. In another embodiment, a suspension of one or more crystalline polymorphic forms of Compound 1 is equilibrated in heptane/isopropanol or in heptane/ethanol, and isolated to give pure Form III. In another embodiment, the ratio of heptane:isopropanol or heptane:ethanol is about 25:1 to about 1:25, about 20:1 to about 1:20, about 10:1 to about 1:10, about 5:1 to about 1:5, or about 2:3 to about 3:2. In another embodiment, the ratio of heptane:isopropanol or heptane:ethanol is about 20:1, about 19:1, about 10:1, about 9:1, about 8:1, about 7:1, about 6:1, about 5:1, about 4:1, about 3:1, about 2:1, about 1:1, about 1:2, about 1:3, about 2:3, about 1:4, about 1:5, about 1:6, about 1:7, about 1:8, about 1:9, or about 1:10. In another embodiment, the ratio of heptane:isopropanol is about 3:2. In another embodiment, the ratio of heptane:ethanol is about 19:1. In another embodiment, the suspension in heptane/isopropanol or heptane/ethanol is equilibrated at about 25° C. In another embodiment, the suspension in heptane/isopropanol or heptane/ethanol is equilibrated at about 5° C. In another embodiment, the suspension in heptane/isopropanol or heptane/ethanol is equilibrated for about 1 hour, about 2 hours, about 3 hours, about 4 hours, about 5 hours, about 6 hours, about 7 hours, about 8 hours, or more. In another embodiment, the suspension in heptane/isopropanol or heptane/ethanol is equilibrated for about 20 hours. In another embodiment, a suspension of one or more crystalline polymorphic forms of Compound 1 is equilibrated in heptane/isopropanol, isolated, re-equilibrated in heptane/isopropanol, or in another non-solvate forming solvent or mixture of non-solvate forming solvents, and re-isolated to give pure Form III. In another embodiment, a suspension of one or more crystalline polymorphic forms of Compound 1 is equilibrated in heptane/ethanol, isolated, re-equilibrated in heptane/ethanol, or in another non-solvate forming solvent or mixture of non-solvate forming solvents, and re-isolated to give pure Form III.

In another embodiment, a suspension of one or more crystalline polymorphic forms or amorphous forms of Compound 1 is equilibrated in methanol/water and isolated to give substantially pure Form V. In another embodiment, a suspension of one or more crystalline polymorphic forms or amorphous forms of Compound 1 is equilibrated in methanol/water and isolated to give pure Form V. In another embodiment, the methanol content in the methanol/water mixture is greater than 60% by volume. In another embodiment, the equilibration of one or more crystalline polymorphic forms or amorphous forms of Compound 1 is repeated in methanol/water more than once, e.g., two, three, four, or five times, or more, to give pure Form V. In another embodiment, the suspension of one or more crystalline polymorphic forms or amorphous forms of Compound 1 is equilibrated in methanol/water for a period of time, e.g., for about 15 minutes, about 30 minutes, about 1 hour, about 2 hours, about 3 hours, about 4 hours, about 5 hours, about 6 hours, about 10 hours, about 12 hours, about 15 hours, about 18 hours, about 20 hours, about 21 hours, about 1 day, about 2 days, about 3 days, about 4 days, about 5 days, about 6 days, about 1 week, about 2 weeks, about 3 weeks, about a month, or longer, until complete conversion to Form V is observed. In another embodiment, the suspension of one or more crystalline polymorphic forms or amorphous forms of Compound 1 is equilibrated in methanol/water at about 65° C. or less, e.g., at about 60° C., at about 50° C., at about 45° C., at about 44° C., about 43° C., about 42° C., about 41° C., about 40° C., about 39° C., about 38°, about 37° C., about 36° C., about 35° C., about 34° C., about 33° C., about 32° C., about 31° C., about 30° C., about 29° C., about 28° C., about 27° C., about 26° C. (i.e., about room temperature), about 25° C., about 24° C., about 23° C., about 22° C., about 21° C., about 20° C., about 19° C., about 18° C., about 17° C., about 16° C., about 15° C., about 14° C., about 13° C., about 12° C., about 11° C., about 10° C., about 9° C., about 8° C., about 7° C., about 6° C., about 5° C., about 4° C., about 3° C., about 2° C., about 1° C., or about 0° C., or less. In another embodiment, the suspension of one or more crystalline polymorphic forms or amorphous forms of Compound 1 is equilibrated in methanol/water at about room temperature, or less.

In another embodiment, a suspension of one or more crystalline polymorphic forms or amorphous forms of Compound 1 is equilibrated in water and isolated to give substantially pure Form IV. In another embodiment, a suspension of one or more crystalline polymorphic forms or amorphous forms of Compound 1 is equilibrated in water and isolated to give pure Form IV. In another embodiment, the equilibration of one or more crystalline polymorphic forms or amorphous forms of Compound 1 is repeated in water more than once, e.g., two, three, four, or five times, or more, to give pure Form IV. In another embodiment, the suspension of one or more crystalline polymorphic forms or amorphous forms of Compound 1 is equilibrated in water for a period of time, e.g., for about 15 minutes, about 30 minutes, about 1 hour, about 2 hours, about 3 hours, about 4 hours, about 5 hours, about 6 hours, about 10 hours, about 12 hours, about 15 hours, about 18 hours, about 20 hours, about 21 hours, about 1 day, about 2 days, about 3 days, about 4 days, about 5 days, about 6 days, about 1 week, about 2 weeks, about 3 weeks, about a month, or longer, until complete conversion to Form IV is observed. In another embodiment, the suspension of one or more crystalline polymorphic forms or amorphous forms of Compound 1 is equilibrated in water at about 65° C. or less, e.g., at about 60° C., at about 50° C., at about 45° C., at about 44° C., about 43° C., about 42° C., about 41° C., about 40° C., about 39° C., about 38°, about 37° C., about 36° C., about 35° C., about 34° C., about 33° C., about 32° C., about 31° C., about 30° C., about 29° C., about 28° C., about 27° C., about 26° C. (i.e., about room temperature), about 25° C., about 24° C., about 23° C., about 22° C., about 21° C., about 20° C., about 19° C., about 18° C., about 17° C., about 16° C., about 15° C., about 14° C., about 13° C., about 12° C., about 11° C., about 10° C., about 9° C., about 8° C., about 7° C., about 6° C., or about 5° C. In another embodiment, the suspension of one or more crystalline polymorphic forms or amorphous forms of Compound 1 is equilibrated in water at about room temperature.

In another aspect, the present disclosure provides a method of preparing substantially pure Compound 1 Form III, the method comprising: a) combining a mixture of one or more polymorphic or amorphous forms of Compound 1 and two or more non-solvate forming solvents at about 26° C. to obtain a slurry; and b) filtering the slurry to give substantially pure Compound 1 Form III. In another embodiment, the two or more non-solvate forming solvents comprise heptane/toluene, heptane/isopropanol, or heptane/ethanol. In another embodiment, pure Compound 1 Form III is prepared according to steps a) and b).

In another aspect, the present disclosure provides a method of preparing substantially pure Compound 1 Form III, the method comprising: a) combining a mixture of one or more polymorphic or amorphous forms of Compound 1 and two or more non-solvate forming solvents at about 26° C. to obtain a slurry; b) heating the slurry to obtain a solution; c) cooling the solution to about 26° C. or less to form a precipitate; and d) filtering the precipitate to give substantially pure Compound 1 Form III. In another embodiment, the two or more non-solvate forming solvents comprise heptane/toluene, heptane/isopropanol, or heptane/ethanol. In another embodiment, the slurry is heated to about 45° C. or more, e.g., about 50° C., about 55° C., about 60° C., about 65° C., about 70° C., about 75° C., about 80° C., or more. In another embodiment, the solution is held at room. In another embodiment, pure Compound 1 Form III is prepared according to steps a), b), c), and d).

In another aspect, the present disclosure provides a method of preparing substantially pure Compound 1 Form III, the method comprising: a) combining a mixture of one or more crystalline polymorphic or amorphous forms of Compound 1 and two or more non-solvate forming solvents at about 26° C. to obtain a slurry; b) heating the slurry to obtain a solution; c) cooling the solution to about 40° C. to about 30° C. (which may or may not cause some precipitation); d) adding about 0.5 weight % or less of pure Compound 1 Form III; and e) filtering the precipitate to give substantially pure Compound 1 Form III. In another embodiment, the two or more non-solvate forming solvents comprise heptane/toluene, heptane/isopropanol, or heptane/ethanol. In another embodiment, the slurry is heated to about 50° C. or more, e.g., about 55° C., about 60° C., about 65° C., about 70° C., about 75° C., about 80° C., or more. In another embodiment, pure Compound 1 Form III is prepared according to steps a), b), c), d), and e).

In another aspect, the present disclosure provides compositions comprising one or more crystalline polymorphic forms or amorphous forms of Compound 1 or Compound 2 and one or more excipients. In one embodiment, compositions comprising Compound 1 Form III and one or more excipients are provided. In another embodiment, compositions comprising amorphous Compound 1 Form X and one or more excipients are provided. In one embodiment, the excipient comprises dimethyl sulfoxide or acetone. In one embodiment, the composition comprises a pharmaceutically acceptable excipient, i.e., a "pharmaceutically acceptable composition." In another embodiment, the composition comprises micronized crystalline polymorphic forms or amorphous forms of Compound 1 or Compound 2. In another embodiment, the composition comprises micronized crystalline Compound 1 Form III. In another embodiment, the pharmaceutically acceptable excipient comprises Miglyol 812, phospholipon 90G, or tocopheryl polyethylene glycol 1000 succinate, or a mixture thereof. In another embodiment, the pharmaceutically acceptable excipient consists essentially of Miglyol 812, phospholipon 90G, and tocopheryl polyethylene glycol 1000 succinate. In another embodiment, the pharmaceutically acceptable excipient comprises Labrasol®. In another embodiment, the pharmaceutically acceptable excipient comprises sorbitan monolaurate, hydroxypropylmethylcellulose acetate succinate, sodium taurocholate, Ethocel™ or palmitoyl-oleoyl-phosphatidylcholine, or a mixture thereof. In another embodiment, the pharmaceutically acceptable excipient comprises hydrogenated soy lecithin. Crystalline polymorphic forms or amorphous forms of Compound 1 or Compound 2 can be admixed with one or more excipients using method well known to those of ordinary skill in the art.

Compositions may contain from 0.01% to 99% by weight of one or more crystalline polymorphic forms or amorphous forms of Compound 1 or Compound 2, e.g., about 1%, about 2%, about 3%, about 4%, about 5%, about 6%, about 7%, about 8%, about 9%, or about 10%, about 15%, about 20%, about 25%, about 30%, about 35%, about 40%, about 45%, about 50%, about 55%, about 60%, about 65%, about 70%, about 75%, about 80%, about 85%, about 90%, or about 95%. The amount in any particular composition will depend upon the effective dose, that is, the dose required to elicit the desired level of gene expression. In one embodiment, the composition comprises from 0.01 to 99% by weight of crystalline Compound 1 Form III. In another embodiment, the composition comprises from 0.01 to 99% by weight of amorphous Compound 1 Form X.

In another aspect, the present disclosure provides methods of making a composition, comprising admixing one or more crystalline polymorphic forms or amorphous forms of Compound 1 or Compound 2 with one or more excipients. In one embodiment, the excipient is a pharmaceutically acceptable excipient. In one embodiment, methods of making a composition comprising admixing Compound 1 Form III and one or more pharmaceutically acceptable excipient are provided. In another embodiment, methods of making a composition comprising admixing amorphous Compound 1 Form X and one or more pharmaceutically acceptable excipient are provided.

In another aspect, the present disclosure provides methods of regulating gene expression of a gene of interest in a host cell, comprising contacting the host cell with one or more crystalline polymorphic forms or amorphous forms of Compound 1 or Compound 2, or a composition thereof. In one embodiment, methods of regulating gene expression of a gene of interest in a host cell, comprising contacting the host cell with a composition comprising crystalline Compound I Form III are provided. In another embodiment, methods of regulating gene expression of a gene of interest in a host cell, comprising contacting the host cell with a composition comprising amorphous Compound 1 are provided. In one embodiment, the host cell comprises a polynucleotide encoding a gene switch comprising a ligand binding domain that binds Compound 1 or Compound 2, wherein the level of expression of the gene of interest is increased, relative to the level of expression of the gene of interest in the absence of Compound 1 or Compound 2, respectively. In another embodiment, the host cell is an isolated host cell. In another embodiment, the host cell is in a subject, e.g., an animal, e.g., a human. In another embodiment, one or more crystalline polymorphic forms of Compound 1 are administered to a subject as a pharmaceutically acceptable composition. In another embodiment, the gene switch comprises an ecdysone receptor ligand binding domain. In another embodiment, the gene switch further comprises a ligand binding domain that dimerizes with the ligand binding domain that binds Compound 1 or Compound 2. In another embodiment, the ligand binding domain that dimerizes with the ligand binding domain that binds Compound 1 or Compound 2 is a retinoic X receptor ligand binding domain. In another embodiment, the ligand binding domain that dimerizes with the ligand binding domain that binds Compound 1 or Compound 2 is a wild-type insect USP (Ultraspiracle protein). In another embodiment, the retinoic X receptor ligand binding domain is a chimeric retinoic X receptor ligand binding domain. In another embodiment, the host cell further comprises a polynucleotide encoding a peptide, protein or polypeptide whose expression is regulated by the gene switch.

In another aspect, the present disclosure provides methods of treating a disease, disorder, injury, or condition in a subject, comprising administering to the subject one or more crystalline polymorphic forms or amorphous forms of Compound 1 or Compound 2, or a composition thereof. In one embodiment, a host cell within the subject comprises a polynucleotide encoding a gene switch that comprises a ligand binding domain that binds Compound 1 or Compound 2. In another embodiment, the subject is human. In another embodiment, the disease, disorder, injury, or condition is selected from the group consisting of cancer, metabolic-related disorder, kidney disease, anemia, autoimmune disorder, ocular disorder, blood disorder, neurological disorder, lung disorder, rheumatologic disorder, and infectious disease. In another embodiment, the disease, disorder, injury, or condition is cancer. In another embodiment, the cancer is melanoma. In another embodiment, the gene switch comprises an ecdysone receptor ligand binding domain. In another embodiment, the gene switch further comprises a ligand binding domain that dimerizes with the ligand binding domain that binds Compound 1. In another embodiment, the ligand binding domain that dimerizes with the ligand binding domain that binds Compound 1 or Compound 2 is a retinoic X receptor ligand binding domain.

In another embodiment, the retinoic X receptor ligand binding domain is a chimeric retinoic X receptor ligand binding domain. In another embodiment, the host cell further comprises a polynucleotide encoding a peptide, protein or polypeptide whose expression is regulated by the gene switch. In another embodiment, the gene switch regulates the expression of a polynucleotide encoding IL-12 or a subunit thereof. (See, for example, WO 2010/042189 A2).

In another embodiment, the present disclosure provides one or more crystalline polymorphic forms or amorphous forms of Compound 1 or Compound 2, or a composition thereof, for use in treating a disease, disorder, injury, or condition in a subject.

In another embodiment, the present disclosure provides one or more crystalline polymorphic forms or amorphous forms of Compound 1 or Compound 2, or a composition thereof, for use in the manufacture of a medicament for treating a disease, disorder, injury, or condition in a subject.

In another aspect, the present disclosure provides kits comprising one or more crystalline polymorphic forms or amorphous forms of Compound 1 or Compound 2, or kits comprising a composition of one or more crystalline polymorphic forms or amorphous forms of Compound 1 or Compound 2 and one or more excipients. In one embodiment, the kit further comprises instructions for administering the one or more crystalline polymorphic forms or amorphous forms of Compound 1 or Compound 2 to an isolated host cell or a subject. In another embodiment, the kit further comprises the RheoSwitch® Therapeutic System (see, for example, the Instruction Manual for "RheoSwitch® Mammalian Inducible Expression System," New England BioLabs® Inc., Version 1.3, November 2007; Karzenowski, D. et al., *BioTechiques* 39:191-196 (2005); Dai, X. et al., *Protein Expr. Purif* 42:236-245 (2005); Palli, S. R. et al., *Eur. J. Biochem.* 270:1308-1515 (2003); Dhadialla, T. S. et al., *Annual Rev. Entomol.* 43:545-569 (1998); Kumar, M. B, et al., *J. Biol. Chem.* 279:27211-27218 (2004); Verhaegent, M. and Christopoulos, T. K., *Annal. Chem.* 74:4378-4385 (2002); Katalam, A. K., et al., *Molecular Therapy* 13:S103 (2006); and Karzenowski, D. et al., *Molecular Therapy* 13:S194 (2006)).

The crystalline polymorphic forms or amorphous forms of Compound 1 or Compound 2 described herein may be administered to a subject in conjunction with other pharmaceutically active compounds. It will be understood by those skilled in the art that pharmaceutically active compounds to be used in combination the crystalline polymorphic forms or amorphous forms of Compound 1 or Compound 2 will be selected in order to avoid adverse effects on the recipient or undesirable interactions between the compounds. Examples of other pharmaceutically active compounds which may be used in combination with one or more crystalline polymorphic forms or amorphous forms of Compound 1 or Compound 2 include, for example, AIDS chemotherapeutic agents, amino acid derivatives, analgesics, anesthetics, anorectal products, antacids and antiflatulents, antibiotics, anticoagulants, antidotes, antifibrinolytic agents, antihistamines, anti-inflamatory agents, antineoplastics, antiparasitics, antiprotozoals, antipyretics, antiseptics, antispasmodics and anticholinergics, antivirals, appetite suppressants, arthritis medications, biological response modifiers, bone metabolism regulators, bowel evacuants, cardiovascular agents, central nervous system stimulants, cerebral metabolic enhancers, cerumenolytics, cholinesterase inhibitors, cold and cough preparations, colony stimulating factors, contraceptives, cytoprotective agents, dental preparations, deodorants, dermatologicals, detoxifying agents, diabetes agents, diagnostics, diarrhea medications, dopamine receptor agonists, electrolytes, enzymes and digestants, ergot preparations, fertility agents, fiber supplements, antifungal agents, galactorrhea inhibitors, gastric acid secretion inhibitors, gastrointestinal prokinetic agents, gonadotropin inhibitors, hair growth stimulants, hematinics, hemorrheologic agents, hemostatics, histamine $H_2$ receptor antagonists, hormones, hyperglycemic agents, hypolipidemics, immunosuppressants, laxatives, leprostatics, leukapheresis adjuncts, lung surfactants, migraine preparations, mucolytics, muscle relaxant antagonists, muscle relaxants, narcotic antagonists, nasal sprays, nausea medications nucleoside analogues, nutritional supplements, osteoporosis preparations, oxytocics, parasympatholytics, parasympathomimetics, Parkinsonism drugs, Penicillin adjuvants, phospholipids, platelet inhibitors, porphyria agents, prostaglandin analogues, prostaglandins, proton pump inhibitors, pruritus medications psychotropics, quinolones, respiratory stimulants, saliva stimulants, salt substitutes, sclerosing agents, skin wound preparations, smoking cessation aids, sulfonamides, sympatholytics, thrombolytics, Tourette's syndrome agents, tremor preparations, tuberculosis preparations, uricosuric agents, urinary tract agents, uterine contractants, uterine relaxants, vaginal preparations, vertigo agents, vitamin D analogs, vitamins, and medical imaging contrast media. In some cases Compound 1 may be useful as an adjunct to drug therapy, for example, to "turn off" a gene that produces an enzyme that metabolizes a particular drug.

For agricultural applications, one or more crystalline polymorphic forms or amorphous forms of Compound 1 or Compound 2 may be used to control the expression of pesticidal proteins such as *Bacillus thuringiensis* (Bt) toxin. Such expression may be tissue or plant specific. In addition, particularly when control of plant pests is also needed, one or more pesticides may be combined with crystalline polymorphic forms or amorphous forms of Compound 1 or Compound 2, thereby providing additional advantages and effectiveness, including fewer total applications, than if the pesticides are applied separately. When mixtures with pesticides are employed, the relative proportions of each component in the composition will depend upon the relative efficacy and the desired application rate of each pesticide with respect to the crops, pests, and/or weeds to be treated. Those skilled in the art will recognize that mixtures of pesticides may provide advantages such as a broader spectrum of activity than one pesticide used alone. Examples of pesticides which can be combined in compositions with crystalline polymorphic forms or amorphous forms of Compound 1 or Compound 2 include fungicides, herbicides, insecticides, miticides, and microbicides.

Ecdysone receptors in insects are naturally responsive to the ecdysone steroid hormone (molting hormone) and other steroidal compounds such as ponasterone A and muristerone A. (Graham et al., *Insect Biochemistry and Molecular Biology* 37:611-626 (2007); Dinan and Hormann, "Ecdysteroid Agonists and Antagonists," *Comprehensive Molecular Insect Science,* 1st ed.:197-242, (2005)). Diacylhydrazines having ecdysone receptor agonist activity have been described as insecticides. (See U.S. Pat. No. 5,530,028).

In another aspect, the present disclosure provides a method of controlling, e.g., reducing or preventing the spread of, or killing, insects comprising contacting the insects or their habitat with an insecticidally effective amount of one or more crystalline polymorphic forms or amorphous forms of Compound 1 or Compound 2, or a composition thereof. In another embodiment, one or more crystalline polymorphic forms or amorphous forms of Compound 1 or Compound 2, or a composition thereof, are insecticidally active against:

(1) insects from the order of the lepidopterans (Lepidoptera), for example, *Agrotis ipsilon, Agrotis segetum, Alabama argillacea, Anficarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalls, Dlatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Hellothis armigera, Hellothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalls, Panolls flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera fruglperda, Spodoptera littoralls, Spodoptera litura, Thaumatopoea pityocampa, Tortrix viridana, Trichoplusia ni* and *Zeiraphera Canadensis;*

(2) beetles (Coleoptera), for example, *Agrilus sinuatus, Agriotes lineatus, Agriotes obscurus, Amphimallus solstitialis, Anisandrus dispar, Anthonomus grandis, Anthonomus pomorum, Aphthona euphoridae, Athous haemorrhoidalis, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Cetonia aurata, Ceuthorrhynchus assimilis, Ceuthorrhynchus napi, Chaetocnema tibialis, Conoderus vespertinus, Crioceris asparagi, Ctenicera* ssp., *Diabrotica longicornis, Diabrotica semipunctata, Diabrotica 12-punctata Diabrotica speciosa, Diabrotica virgifera, Epilachna varivestis, Epitrix hiirtpennis, Eutinobothrus brasiilensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Otiorrhynchus sulcatus, Otiorrhynchus ovatus, Phaedon cochleariae, Phyllobius pyri, Phyllotreta chrysocephala, Phyllophaga* sp., *Phyllopertha horticola, Phyllotreta nemorum, Phyllotreta striolata, Popilliajaponica, Sitona lineatus* and *Sitophilus granaria;*

(3) flies, mosquitoes (Diptera), for example, *Aedes aegypti, Aedes albopictus, Aedes vexans, Anastrepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, Calliphora vicina, Ceratitis capitata, Chrysomya bezziana, Chrysomya hominivorax, Chrysomya macellaria, Chrysops discails, Chrysops silacea, Chrysops allanticus, Cochliomyla hominivorax, Contarinia sorghicola Cordylobia anthropophaga, Culicoides furens, Culex pipiens, Culex nigripalpus, Culex quinquefasciatus, Culex tarsalis, Culiseta inornata, Culiseta melanura, Dacus cucurbitae, Dacus oleae, Dasineura brassicae, Delia antique, Delia coarctata, Delia platura, Della radicum, Dermatobia hominis, Fannia canicularis, Geomyza Tripunctata, Gasterophilus intestinalis, Glossina morsifians, Glossina palpalis, Glossina fuscipes, Glossina tachinoides, Haematobia irritans, Haplodiplosis equestris, Hippelates* spp., *Hylemyia platura, Hypoderma lineata, Leptoconops torrens, Liriomyza sativae, Liriomyza trifolii, Lucilia caprina, Lucilia cuprina, Lucilla sericata, Lycoria pectoralis, Mansonia titillanus, Mayetiola destructor, Musca domestica, Muscina stabulans, Oestrus ovis, Opomyza florum, Oscinella frit, Pegomya hysocyami, Phorbia antiqua, Phorbia brassicae, Phorbia coarctata, Phlebotomus argentipes, Psorophora columbiae, Psila rosae, Psorophora discolor, Prosimullum mixtum, Rhagoletis cerasi, Rhagoletis pomonella, Sarcophaga haemorrhoidalis, Sarcophaga* sp., *Simulium vittatum, Stomoxys calcitrans, Tabanus bovinus, Tabanus atratus, Tabanus lineola*, and *Tabanus similis, Tipula oleracea*, and *Tipulapaludosa:*

(4) thrips (Thysanoptera), for example, *Dichromothrips corbetti, Dichromothrips* ssp, *Frankliniella fusca, Frankllniella occidentalls, Frankllniella tritici, Scirtothrlps citri, Thrips olyzae, Thrips palmi* and *Thrips tabaci,*

(5) termites (Isoptera), for example, *Calotermes flavicollis, Leucotermes flavipes, Heterotermes aureus, Reticulltermes flavipes, Retfculltermes virginicus, Reticulltermes lucifugus, Termes natalensis*, and *Coptotermesformosanus,*

(6) cockroaches (Blattaria-Blattodea), for example, *Blattella germanica, Blattella asahinae, Periplaneta americana, Periplaneta japonica, Periplaneta brunnea, Periplaneta fuligginosa, Periplaneta australasiae*, and *Blatta orientalis;*

(7) true bugs (Hemiptera), for example, *Acrosternum hilare, Blissus leucopterus, Cyrtopeltis notatus, Dysdercus cingulatus, Dysdercus intermedius, Eurygaster integriceps, Euschistus impictivenfris, Leptoglossus phyllopus, Lygus llneolaris, Lygus pratensis, Nezara viriduia, Piesma quadrata, Solubea insularis, Thyanta perditor, Acyrthosiphon onobrychis, Adelges laricis, Aphidula nasturti; Aphis fabae, Aphis forbesi, Aphis pomi, Aphis gossypii, Aphis grossulariae, Aphis schneideri, Aphis spiraecola, Aphis sambuci, Acyrthosiphon pisum, Aulacofthum solani, Bemisia argentifolii, Brachycaudus cardui, Brachycaudus helichrysi, Brachycaudus persicae, Brachycaudus prunicola, Brevicoryne brassicae, Capiftophorus horni, Cerosipha gossypii, Chaetosiphon fragaefolii, Cryptomyzus ribis, Dreyfusia nordmannianae, Dreyfusia piceae, Dysaphis radicola, Dysaulacorthum pseudosolani, Dysaphis plantaginea, Dysaphis pyri, Empoasca fabae, Hyalopterus pruni, Hyperomyzus lactucae, Macrosiphum avenae, Macrosiphum euphorbiae, Macrosiphon rosae, Megoura viciae, Melanaphis pyrarius, Metopolophium dirhodum, Myzus persicae, Myzus ascalonicus, Myzus cerasi, Myzus varians, Nasonovia ribis-nigri, Nilaparvata lugens, Pemphigus bursarius, Perkinsiella saccharicida, Phorodon humuli, Psylla mall, Psylla piri, Rhopalomyzus ascalonicus, Rhopalosiphum maidis, Rhopalosiphum padi, Rhopalosiphum inserfum, Sappaphis mala, Sappaphis mali, Schizaphis graminum, Schizoneura lanuginosa, Sitobion avenae, Trialeurodes vaporariorum, Toxoptera aurantiiand, Viteus vitifolli, Cimex lectularius, Cimex hemipterus, Reduvius senilis, Triatoma* spp., and *Arilus critatus;*

(8) ants, bees, wasps, sawflies (Hymenoptera), for example, *Athalia rosae, Atta cephalotes, Atta capiguara, Atta cephalotes, Afta laevigata, Atta robusta, Atta sexdens, Atta texana, Crematogaster* spp., *Hoplocampa minuta, Hoplocampa testudinea, Monomorium pharaonls, Solenopsis geminata, Solenopsis invicta, Solenopsis richteri, Solenopsis xyloni, Pogonomyrmex barbatus, Pogonomyrmex californicus, Pheidole megacephala, Dasymutilla occidentalis,*

*Bombus* spp. *Vespula squamosa, Paravespula vulgaris, Paravespula pennsylvanica, Paravespula germanica, Dolichovespula maculata, Vespa crabro, Polistes rubiginosa, Camponotus floridanus*, and *Linepithema humile;*

(9) crickets, grasshoppers, locusts (Orthoptera), for example, *Acheta domestica, Gryllotalpa gryllotalpa, Locusta migratoria, Melanoplus bivittatus, Melanoplus femurrubrum, Melanoplus mexicanus, Melanoplus sanguinipes, Melanoplus spretus, Nomadacris septemfasciata, Schistocerca americans, Schistocerca gregaria, Dociostaurus maroccanus, Tachycines asynamorus, Oedaleus senegalensis, Zonozerus variegatus, Hieroglyphus daganensis, Kraussaria angulifera, Calliptamus itallcus, Chortoicetes terminifera*, and *Locustana pardalina;*

(10) Arachnoidea, such as arachnids (Acarina), for example, of the families Argasidae, Ixodidae and Sarcoptidae, such as *Amblyomma americanum, Amblyomma variegatum, Ambryomma maculatum, Argas persicus, Boophilus annulatus, Boophilus decoloratus, Boophilus microplus, Dermacentor silvarum, Dermacentor andersoni, Dermacentor variabllis, Hyalomma truncatum, Ixodes ricinus, Ixodes rubicundus, Ixodes scapularis, Ixodes holocyclus, Ixodes pacificus, Ornithodorus moubata, Ornithodorus hermsi, Ornithodorus turicata, Ornithonyssus bacoti, Otobius megnini, Dermanyssus gallinae, Psoroptes ovis, Rhipicephalus sanguineus, Rhipicephalus appendiculatus, Rhipicephalus evertsi, Sarcoptes scabiei*, and *Eriophyidae* spp. such as *Aculus schlechtendali, Phyllocoptrata oleivora* and *Eriophyes sheldoni, Tarsonemidae* spp. such as *Phytonemus pallidus* and *Polyphagotarsonemus latus; Tenuipalpidae* spp. such as *Brevipalpus phoenicis; Tetranychidae* spp. such as *Tetranychus cinnabarinus, Tetranychus kanzawai, Tetranychus pacificus, Tetranychus telarius* and *Tetranychus urticae, Panonychus ulmi, Panonychus citri*, and *Oligonychus pratensis; Araneida*, e.g., *Lafrodectus mactans*, and *Loxosceles reclusa*,

(11) fleas (Siphonaptera), for example, *Ctenocephalides felis, Ctenocephalides canis, Xenopsylla cheopis, Pulex irriftans, Tunga penefrans*, and *Nosopsyllus fasciatus;*

(12) silverfish, firebrat (Thysanura), for example, *Lepisma saccharins* and *Thermobia domestics:*

(13) centipedes (Chilopoda), for example, *Scutigera coleoptrata*,

(14) millipedes (Diplopoda), for example, *Narceus* spp.,

(15) Earwigs (Dermaptera), for example, *forifcula auricularia*; and/or

(16) lice (Phthiraptera), for example, *Pediculus humanus capitis, Pediculus humanus corporis, Pthirus pubis, Haematopinus eurysternus, Haematopinus suis, Linognathus vituli, Bovicola bovis, Menopon gallinae, Menacanthus stramineus* and *Solenopotes capillatus.*

In another embodiment, one or more crystalline polymorphic forms or amorphous forms of Compound 1 or Compound 2, or a composition thereof, are insecticidally active against insects of the order Diptera, Hemiptera, and/or Lepidoptera. In another embodiment, one or more crystalline polymorphic forms or amorphous forms of Compound 1 or Compound 2, or a composition thereof, are insecticidally active against insects of the order Lepidoptera. In another embodiment, one or more crystalline polymorphic forms or amorphous forms of Compound 1 or Compound 2, or a composition thereof, are insecticidally active against insects of the order Hemiptera.

The crystalline polymorphic forms or amorphous forms of Compound 1 or Compound 2 described herein can be applied to plant foliage as aqueous sprays by methods commonly employed, such as conventional high-liter hydraulic sprays, low-liter sprays, air-blast, and aerial sprays. The dilution and rate of application will depend upon the type of equipment employed, the method and frequency of application desired, and the ligand application rate. It may be desirable to include additional adjuvants in the spray tank. Such adjuvants include surfactants, dispersants, spreaders, stickers, antifoam agents, emulsifiers, and other similar materials described in *McCutcheon's Emulsifiers and Detergents, McCutcheon's Emulsifiers and Detergents/Functional Materials*, and *McCutcheon's Functional Materials*, all published annually by McCutcheon Division of MC Publishing Company (New Jersey). Crystalline polymorphic forms or amorphous forms of Compound 1 or Compound 2 can also be mixed with fertilizers or fertilizing materials before their application. Crystalline polymorphic forms or amorphous forms of Compound 1 or Compound 2 and solid fertilizing material can also be admixed in mixing or blending equipment, or they can be incorporated with fertilizers in granular formulations. Any relative proportion of fertilizer can be used which is suitable for the crops and weeds to be treated. The crystalline polymorphic forms or amorphous forms of Compound 1 or Compound 2 described herein will commonly comprise from 5% to 50% of the fertilizing composition. These compositions provide fertilizing materials which promote the rapid growth of desired plants, and at the same time control gene expression.

As used herein, the term "Compound 1" refers to (R)-3,5-dimethyl-benzoic acid N-(1-tert-butyl-butyl)-N'-(2-ethyl-3-methoxy-benzoyl)-hydrazide. In one embodiment, Compound 1 comprises about 10% or less, i.e., about 9%, about 8%, about 7%, about 6%, about 5%, about 4%, about 3%, about 2%, about 1%, or about 0.5%, or less, of (S)-3,5-dimethyl-benzoic acid N-(1-tert-butyl-butyl)-N'-(2-ethyl-3-methoxy-benzoyl)-hydrazide, by weight. The stereoisomeric purity of Compound 1 can be determined using conventional analytical methods such as chiral HPLC.

As used herein, the term "Compound 2" refers to (S)-3,5-dimethyl-benzoic acid N-(1-tert-butyl-butyl)-N'-(2-ethyl-3-methoxy-benzoyl)-hydrazide. In one embodiment, Compound 2 comprises about 10% or less, i.e., about 9%, about 8%, about 7%, about 6%, about 5%, about 4%, about 3%, about 2%, about 1%, or about 0.5%, or less, of (R)-3,5-dimethyl-benzoic acid N-(1-tert-butyl-butyl)-N'-(2-ethyl-3-methoxy-benzoyl)-hydrazide, by weight. The stereoisomeric purity of Compound 2 can be determined using conventional analytical methods such as chiral HPLC.

As used herein, the term "substantially pure" with reference to a particular crystalline polymorphic form of Compound 1 or Compound 2 means that the polymorphic form comprises about 10% or less, i.e., about 9%, about 8%, about 7%, about 6%, about 5%, about 4%, about 3%, about 2%, or about 1%, or less, by weight of any other physical forms of Compound 1 or Compound 2, respectively.

As used herein, the term "substantially pure" with reference to amorphous Compound 1 or Compound 2 means that the amorphous form comprises about 10% or less, i.e., about 9%, about 8%, about 7%, about 6%, about 5%, about 4%, about 3%, about 2%, or about 1%, or less, by weight of any crystalline forms of Compound 1 or Compound 2, respectively.

As used herein, the term "pure" with reference to a particular crystalline polymorphic form of Compound 1 or Compound 2 means that the polymorphic form comprises about 1% or less, i.e., about 0.9%, about 0.8%, about 0.7%, about 0.6%, about 0.5%, about 0.4%, about 0.3%, about 0.2%, or about 0.1%, or less, by weight of any other physical forms of Compound 1 or Compound 2, respectively. In one embodiment, a "pure" polymorphic form contains no PXRD-detectable amount of any other physical forms of Compound 1.

As used herein, the term "pure" with reference to amorphous Compound 1 or Compound 2 means that the amorphous form comprises about 1% or less, i.e., about 0.9%, about 0.8%, about 0.7%, about 0.6%, about 0.5%, about 0.4%, about 0.3%, about 0.2%, or about 0.1%, or less, by weight of any crystalline forms of Compound 1 or Compound 2, respectively.

As used herein, the term "amorphous" refers to a solid form of Compound 1 or Compound 2 that lacks the long-range order characteristic of a crystal, i.e., the solid is non-crystalline.

As used herein, the term "essentially the same" with reference to PXRD peak positions and relative intensities means that peak position and intensity variability are taken into account when comparing PXRD diffractograms. Likewise, the term "essentially the same" with reference to FT-Raman peak positions means that peak position variability are taken into account when comparing FT-Raman spectra. For example, PXRD peak positions can show inter-apparatus variability, e.g., as much as 0.2°. Relative peak intensities can also show inter-apparatus variability due to degree of crystallinity, orientation, prepared sample surface, and other factors known to those skilled in the art, and should be taken as qualitative measures only.

As used herein, the term "micronization" refers to a process or method by which the size of a population of particles is reduced, typically to the micron scale.

As used herein, the term "micron" or "μm" refer to "micrometer," which is $1 \times 10^{-6}$ meter.

As used herein, the term "therapeutically effective amount," refers to the amount of Compound 1 or Compound 2 sufficient to treat one or more symptoms of a disease, condition, injury, or disorder, or prevent advancement of disease, condition, injury, or disorder, or cause regression of the disease, condition, injury, or disorder. For example, with respect to the treatment of cancer, in one embodiment, a therapeutically effective amount will refer to the amount of Compound 1 or Compound 2 that decreases the rate of tumor growth, decreases tumor mass, decreases the number of metastases, increases time to tumor progression, or increases survival time by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100%.

As used herein, the term "insecticidally effective amount" refers to the amount of Compound 1 or Compound 2 sufficient to control, e.g., reduce or prevent the spread of, or kill, insects. For example, an insecticidally effect amount will refer to the amount of Compound 1 or Compound 2 that induces premature molting and death in an insect.

The terms "a" and "an" refer to one or more than one.

The term "about," as used herein, includes the recited number±10%. Thus, "about 10" means 9 to 11.

As used herein, the term "average particle size distribution" or "$D_{50}$" is the diameter where 50 mass-% of the particles have a larger equivalent diameter, and the other 50 mass-% have a smaller equivalent diameter as determined by laser diffraction in Malvern Master Sizer Microplus equipment or its equivalent, or other suitable techniques.

As used herein, the term "non-solvate forming solvent" refers to a solvent that does not form a solvate or hydrate, with Compound 1 or Compound 2. Non-solvate forming solvents include, but are not limited to, hexane, heptane, cumeme, diethyl ether, toluene, ethyl acetate, tert-butyl methyl ether, n-dodecane, ethanol, and isopropanol.

As used herein, the term "excipient" refers to any ingredient in a composition other than the one or more crystalline polymorphic forms or amorphous forms of Compound 1 or Compound 2. An excipient is typically an inert substance added to a composition to facilitate processing, handling, administration, etc. of the one or more crystalline polymorphic forms or amorphous forms of Compound 1 or Compound 2. Useful excipients include, but are not limited to, adjuvants, antiadherents, binders, carriers, disintegrants, fillers, flavors, colors, diluents, lubricants, glidants, preservatives, sorbents, solvents, surfactants, and sweeteners.

Conventional pharmaceutical excipients are well known to those of skill in the art. In particular, one of skill in the art will recognize that a wide variety of pharmaceutically acceptable excipients can be used in admixture with crystalline polymorphic forms or amorphous forms of Compound 1 or Compound 2, including those listed in the *Handbook of Pharmaceutical Excipients*, Pharmaceutical Press 4th Ed. (2003), and *Remington: The Science and Practice of Pharmacy*, Lippincott Williams & Wilkins, 21st ed. (2005). In one embodiment, the composition comprises one or more of the following excipients: water, Labrasol, Lauroglycol 90, Phosal 53 MCT, Miglyol, Cremophor EL, polysorbate 80, Crillet 1 HP, Isopropyl myristate, Oleic acid, and/or PEG 400 NF. In another embodiment, the composition comprises a lipid.

Pharmaceutically acceptable carriers include fillers such as saccharides, for example, trehalose, lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are flow-regulating agents and lubricants, for example, silica, talc, stearic acid or salts thereof, such as magnesium stearate or calcium stearate, and/or polyethylene glycol. In one embodiment, dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethyl-cellulose phthalate, are used. Dye stuffs or pigments may be added to the tablets or dragee coatings, for example, for identification or in order to characterize combinations of active compound doses.

Pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules or nanoparticles which may optionally be mixed with fillers such as lactose, binders such as starches, and/or lubricants such as talc or magnesium stearate and, optionally, stabilizers. In one embodiment, the is dissolved or suspended in suitable liquids, such as fatty oils, or liquid paraffin, optionally with stabilizers.

Fatty oils may comprise mono-, di- or triglycerides. Mono-, di- and triglycerides include those that are derived from $C_6$, $C_8$, $C_{10}$, $C_{12}$, $C_{14}$, $C_{16}$, $C_{18}$, $C_{20}$ and $C_{22}$ acids. Exemplary diglycerides include, in particular, diolein, dipalmitolein, and mixed caprylin-caprin diglycerides. Preferred triglycerides include vegetable oils, fish oils, animal fats, hydrogenated vegetable oils, partially hydrogenated vegetable oils, synthetic triglycerides, modified triglycerides, fractionated triglycerides, medium and long-chain triglycerides, structured triglycerides, and mixtures thereof. Exemplary triglycerides include: almond oil; babassu oil; borage oil; blackcurrant seed oil; canola oil; castor oil; coconut oil; corn oil; cottonseed oil; evening primrose oil; grapeseed oil; groundnut oil; mustard seed oil; olive oil; palm oil; palm kernel oil; peanut oil; rapeseed oil; safflower oil; sesame oil; shark liver oil; soybean oil; sunflower oil; hydrogenated castor oil; hydrogenated coconut oil; hydrogenated palm oil; hydrogenated soybean oil; hydrogenated vegetable oil; hydrogenated cottonseed and castor oil; partially hydrogenated soybean oil; partially soy and cottonseed oil; glyceryl tricaproate; glyceryl tricaprylate; glyceryl tricaprate; glyceryl triundecanoate; glyceryl trilaurate; glyceryl trioleate; glyceryl trilinoleate; glyceryl trilinolenate; glyceryl tricaprylate/caprate; glyceryl tricaprylate/caprate/laurate; glyceryl tricaprylate/caprate/linoleate; and glyceryl tricaprylate/caprate/stearate.

In one embodiment, the triglyceride is the medium chain triglyceride available under the trade name LABRAFAC CC. Other triglycerides include neutral oils, e.g., neutral plant oils, in particular fractionated coconut oils such as known and commercially available under the trade name MIGLYOL, including the products: MIGLYOL 810; MIGLYOL 812; MIGLYOL 818; and CAPTEX 355. Other triglycerides are caprylic-capric acid triglycerides such as known and commercially available under the trade name MYRITOL, including the product MYRITOL 813. Further triglycerides of this class are CAPMUL MCT, CAPTEX 200, CAPTEX 300, CAPTEX 800, NEOBEE M5 and MAZOL 1400.

Pharmaceutical compositions comprising triglycerides may further comprise lipophilic and/or hydrophilic surfactants which may form clear solutions upon dissolution with an aqueous solvent. One such surfactant is tocopheryl polyethylene glycol 1000 succinate (vitamin E TPGS). Examples of such compositions are described in U.S. Pat. No. 6,267,985.

In another embodiment, the pharmaceutically acceptable carrier comprises LABRASOL (Gattefosse SA), which is PEG-8 caprylic/capric glycerides. In another embodiment, the pharmaceutically acceptable carrier comprises PL90G, vitamin E TPGS, and Miglyol 812N.

As used herein, the term "treat," "treating," or "treatment" is meant to encompass administering to a subject one or more crystalline polymorphic forms or amorphous forms of Compound 1 or Compound 2, or a composition thereof, for the purposes of amelioration or cure of a disease, disorder, injury, or condition, including preemptive treatment.

As used herein, the term "subject" refers to an intact insect, plant, algae, or animal, e.g., human or veterinary animal, e.g., cow, sheep, pig, horse, dog, or cat. In one embodiment, a host cell of the subject comprises a polynucleotide encoding a gene switch that comprises a ligand binding domain that binds Compound 1. In another embodiment, a host cell of the subject comprises a polynucleotide encoding a gene switch that comprises a ligand binding domain that binds Compound 2.

As used herein, the term "gene of interest" is any gene that one wishes to express that encodes a peptide, protein, or polypeptide.

As used herein, the term "gene expression" refers to the transcription of DNA to messenger RNA (mRNA), and/or the translation of mRNA to amino acid sequence.

As used herein, the term "regulating gene expression" refers to increasing the level of gene expression in response to contact of Compound 1 with the ligand binding domain that binds Compound 1, relative to the level of gene expression in the absence of contacting the ligand binding domain that binds Compound 1 with Compound 1.

As used herein, the term "gene switch" refers to peptide, protein or polypeptide complex that functions to (a) bind Compound 1 or Compound 2, i.e., the ligand, and (b) regulate the transcription of a gene of interest in a ligand-dependent fashion. Gene switches are useful for various applications such as gene therapy, production of proteins in cells, cell based high throughput screening assays, functional genomics, and regulation of traits in transgenic plants and animals.

In one embodiment, the polynucleotide encoding a gene switch is a recombinant polynucleotide, i.e., a polynucleotide, that has been engineered, by molecular biological manipulation, to encode the gene switch. In another embodiment, the recombinant polynucleotide is a synthetic polynucleotide.

As used herein, the term "gene" refers to a polynucleotide comprising nucleotides that encode a functional molecule, including functional molecules produced by transcription only (e.g., a bioactive RNA species) or by transcription and translation (e.g. a polypeptide). The term "gene" encompasses cDNA and genomic DNA nucleic acids. "Gene" also refers to a nucleic acid fragment that expresses a specific RNA, protein or polypeptide, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and/or coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. A chimeric gene may comprise coding sequences derived from different sources and/or regulatory sequences derived from different sources. "Endogenous gene" refers to a native gene in its natural location in the genome of an organism. A "foreign" gene or "heterologous" or "exogenous" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

In one embodiment, one or more crystalline polymorphic forms or amorphous forms of Compound 1 or Compound 2 are administered to an isolated host cell or a subject as a composition. In another embodiment, one or more crystalline polymorphic forms or amorphous forms of Compound 1 or Compound 2 are administered to an isolated host cell or a subject as a pharmaceutically acceptable composition.

As used herein, the term "dimerizes with the ligand binding domain that binds Compound 1" refers to a selective protein-protein interaction.

In one embodiment, the gene switch efficacy or "$EC_{50}$" of Compound 1 is about 100 nM or less, e.g., about 75 nM about 50 nM, about 25 nM, about 15 nM, about 10 nM, about 9 nM, about 8 nM, about 7 nM, about 6 nM, about 5 nM, about 4 nM, about 3 nM, about 2 nM, about 1 nM, about 0.5 nM, or less in a cellular gene switch assay. Examples of in vitro assays for measuring gene switch-regulated gene expression are well known to those of ordinary skill in the art. See, for example, Karzenowski et al., *BioTechniques* 39: 191-200 (2005). In another embodiment, the gene switch efficacy of Compound 2 is about 100 nM or less, e.g., about 75 nM about 50 nM, about 25 nM, about 15 nM, about 10 nM, about 9 nM, about 8 nM, about 7 nM, about 6 nM, about 5 nM, about 4 nM, about 3 nM, about 2 nM, about 1 nM, about 0.5 nM, or less in a cellular gene switch assay. As used herein, the "$EC_{50}$" is the "half maximal effective concentration," which refers to the concentration of Compound 1 or Compound 2 that induces a gene switch-regulated change in expression of a polynucleotide encoding an gene of interest that is halfway between the baseline level of expression and the maximum level of expression after a specified exposure time.

As used herein, the term "ligand binding domain that binds Compound 1" refers to an amino acid sequence that selectively binds Compound 1. In the methods disclosed herein, Compound 1 binds to a ligand binding domain, e.g., an ecdysone receptor ligand binding domain, that is part of a ligand-dependent transcriptional activation complex that regulates the expression of a polynucleotide sequence that encodes a gene of interest. Hence, the expression of the gene of interest is regulated in a ligand (Compound 1) dependent fashion. Likewise, the term "ligand binding domain that binds Compound 2" refers to an amino acid sequence that selectively binds Compound 2.

In one embodiment, the ligand binding domain that binds Compound 1, e.g., an ecdysone receptor ligand binding domain, dimerizes with another ligand binding domain, e.g., a retinoid X receptor ligand binding domain, to form a protein-protein complex.

In one embodiment, the expression of the gene of interest is regulated by Compound 1 or Compound 2 in an on/off fashion that is independent of the concentration or dosage of Compound 1 or Compound 2, respectively. In another embodiment, the expression of the gene of interest is regulated by Compound 1 in a concentration (or dosage)-dependent fashion, i.e., there is a dose-response relationship between the concentration (or dosage) of Compound 1 and the level of gene expression of the gene of interest. See, e.g., US 2009/0123441.

The term "operably linked" refers to the association of polynucleotide sequences on a single polynucleotide so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

In one embodiment, the host cell is an isolated host cell. In one embodiment, an "isolated" host cell refers to a cell that is not present in a subject. In one embodiment, an "isolated" host cell refers to one or more host cells in a cell culture apparatus or in a cell culture preparation.

In one embodiment, the host cell is within a subject, and the host cell is contacted by Compound 1 or Compound 2 by administering one or more crystalline polymorphic forms or amorphous forms of Compound 1 or Compound 2, or a composition thereof, to the subject. In another embodiment, the host cell is contacted with one or more crystalline polymorphic forms of Compound 1, or a composition thereof, in vitro. In another embodiment, the host cell is contacted with one or more crystalline polymorphic forms of Compound 1, or a composition thereof, ex vivo. In another embodiment, the host cell is in a human subject. In another embodiment, the host cell is in an animal subject. In another embodiment, the host cell is in a plant subject. In another embodiment, the host cell is in an algae subject. In another embodiment, the host cell is contacted by crystalline Compound 1 Form III, or a composition comprising crystalline Compound 1 Form III and one or more excipients.

In one embodiment, one or more crystalline polymorphic forms or amorphous forms of Compound 1 or Compound 2, or a composition thereof, are administered to a subject. In one embodiment, one or more crystalline polymorphic forms or amorphous forms of Compound 1 or Compound 2, or a composition thereof, are administered to a subject orally. In another embodiment, one or more crystalline polymorphic forms or amorphous forms of Compound 1 or Compound 2, or a composition thereof, are administered to a subject parenterally. In another embodiment, one or more crystalline polymorphic forms or amorphous forms of Compound 1 or Compound 2, or a composition thereof, are administered subcutaneously, intramuscularly, intravenously, intraperitoneally or intratumorally. In another embodiment, crystalline Compound 1 Form III, or a composition thereof, is administered to a subject. In another embodiment, amorphous Compound 1 Form X, or a composition thereof, is administered to a subject.

In addition to or together with the above modes of administration, one or more crystalline polymorphic forms or amorphous forms of Compound 1 or Compound 2, or a composition thereof, can be added to food consumed by a subject. In one embodiment, one or more crystalline polymorphic forms or amorphous forms of Compound 1 or Compound 2, or a composition thereof, is combined, blended, or admixed with food material to provide a "food product." The term "food material" is used in its broadest possible sense, and includes any form, e.g., solid, emulsion, liquid, of ingestible materials consumed by an animal, e.g., a human. Food products may be formulated so the subject takes in an appropriate quantity of one or more crystalline polymorphic forms or amorphous forms of Compound 1 or Compound 2 with its diet. In another embodiment, one or more crystalline polymorphic forms or amorphous forms of Compound 1 or Compound 2, or a composition thereof, is formulated as a premix for addition to food material. In one embodiment, the food product or premix comprises one or more crystalline polymorphic forms or amorphous forms of Compound 1 or Compound 2, or a composition thereof, and one or more lipids.

In one embodiment, the ligand binding domain in the gene switch that binds Compound 1 or Compound 2 is a Group H nuclear receptor ligand binding domain, or a mutant thereof that binds Compound 1 or Compound 2, respectively. In another embodiment, the Group H nuclear receptor ligand binding domain is selected from the group consisting of an ecdysone receptor ligand binding domain, a ubiquitous receptor ligand binding domain, an orphan receptor-1 ligand binding domain, an NER-1 ligand binding domain, a receptor-interacting protein-15 ligand binding domain, a liver X receptor-3 ligand binding domain, a steroid hormone receptor-like protein ligand binding domain, a liver X receptor ligand binding domain, a liver X receptor ligand binding domain, a farnesoid X receptor ligand binding domain, a receptor-interacting protein-14 ligand binding domain, and a farnesol receptor ligand binding domain ligand binding domain, or a mutant thereof that binds Compound 1.

In another embodiment, the Group H nuclear receptor ligand binding domain is an ecdysone receptor ligand binding domain, or a mutant thereof that binds Compound 1 or Compound 2. In another embodiment, the ecdysone receptor ligand binding domain is selected from the group consisting of an Arthropod ecdysone receptor ligand binding domain a Lepidopteran ecdysone receptor ligand binding domain, a Dipteran ecdysone receptor ligand binding domain, an Orthopteran ecdysone receptor ligand binding domain, a Homopteran ecdysone receptor ligand binding domain and a Hemipteran ecdysone receptor ligand binding domain, a spruce budworm *Choristoneura fumiferana* ecdysone receptor ligand binding domain, a beetle *Tenebrio molitor* ecdysone receptor ligand binding domain, a *Manduca sexta* ecdysone receptor ligand binding domain, a *Heliothies virescens* ecdysone receptor ligand binding domain, a midge *Chironomus tentans* ecdysone receptor ligand binding domain, a silk moth *Bombyx mori* ecdysone receptor ligand binding domain, a squinting bush brown *Bicyclus anynana* ecdysone receptor ligand binding domain, a buckeye *Junonia coenia* ecdysone receptor ligand binding domain, a fruit fly *Drosophila melanogaster* ecdysone receptor ligand binding domain, a mosquito *Aedes aegypti* ecdysone receptor ligand binding domain, a blowfly *Lucilia capitata* ecdysone receptor ligand binding domain, a blowfly *Lucilia cuprina* ecdysone receptor ligand binding domain, a blowfly *Calliphora vicinia* ecdysone receptor ligand binding domain, a Mediterranean fruit fly *Ceratitis capitata* ecdysone receptor ligand binding domain, a locust *Locusta migratoria* ecdysone receptor ligand binding domain, an aphid *Myzus persicae* ecdysone receptor ligand binding domain, a fiddler crab *Celuca pugilator* ecdysone receptor ligand binding domain, an ixodid tick *Amblyomma americanum* ecdysone receptor ligand binding domain, a whitefly *Bamecia argentifoli* ecdysone receptor ligand binding domain, a leafhopper *Nephotetix cincticeps* ecdysone receptor ligand binding domain, or a mutant thereof that binds Compound 1 or Compound 2. In another embodiment, the ecdysone receptor ligand binding domain is a spruce budworm *Choristoneura fumiferana* ecdysone receptor ligand binding domain, for which the amino acid sequence is:

Leu Thr Ala Asn Gln Gln Phe Leu Ile Ala Arg Leu Ile Trp Tyr Gln Asp Gly Tyr Glu Gln Pro Ser Asp Glu Asp Leu Lys Arg Ile Thr Gln Thr Trp Gln Gln Ala Asp Asp Glu Asn Glu Glu Ser Asp Thr Pro Phe Arg Gln Ile Thr Glu Met Thr Ile Leu Thr Val Gin Leu Ile Val Glu Phe Ala Lys Gly Leu Pro Gly Phe Ala Lys Ile Ser Gln Pro Asp Gin Ile Thr Leu Leu Lys Ala Cys Ser Ser Glu Val Met Met Leu Arg Val Ala Arg Arg Tyr Asp Ala Ala Ser Asp Ser Val (position 107) Leu Phe Ala Asn Asn Gln Ala Tyr Thr Arg Asp Asn Tyr Arg Lys Ala Gly Met Ala Tyr (position 127) Val Ile Glu Asp Leu Leu His Phe Cys Arg Cys Met Tyr Ser Met Ala Leu Asp Asn Ile His Tyr Ala Leu Leu Thr Ala Val Val Ile Phe Ser Asp Arg Pro Gly Leu Glu Gln Pro Gln Leu Val Glu Glu Ile Gln Arg Tyr Tyr Leu Asn Thr Leu Arg Ile Tyr Ile Leu Asn Gln Leu Ser Gly Ser Ala Arg Ser Ser Val Ile Tyr Gly Lys Ile Leu Ser Ile Leu Ser Glu Leu Arg Thr Leu Gly Met Gin Asn Ser Asn Met Cys Ile Ser Leu Lys Leu Lys Asn Arg Lys Leu Pro Pro Phe Leu Glu Glu Ile Trp Asp Val (SEQ ID NO: 1), which is also set forth as SEQ NO: 1 in U.S. Patent Publication No. 2006/0100416 A1.

In another embodiment, the ecdysone receptor ligand binding domain is a mutant of the spruce budworm *Choristoneura fumiferana* ecdysone receptor ligand binding domain that binds Compound 1.

Suitable ecdysone receptor ligand binding domains include those disclosed, for example, in U.S. Pat. Nos. 7,935,510; 7,919,269; 7,563,879; and in U.S. Patent Publication No. 2006/0100416 A1.

In one embodiment, the gene switch comprises a ligand binding domain that dimerizes with the ligand binding domain that binds Compound 1 or Compound 2. In one embodiment, the ligand binding domain that dimerizes with the ligand binding domain that binds the Compound 1 or Compound 2 is a Group B nuclear receptor ligand binding domain. In another embodiment, the Group B nuclear receptor ligand binding domain is selected from the group consisting of a retinoid X receptor ligand binding domain, an H-2 region II binding protein ligand binding domain, a nuclear receptor co-regulator-1 ligand binding domain, an ultraspiracle protein ligand binding domain, a 2C1 nuclear receptor ligand binding domain, and a chorion factor 1 ligand binding domain. In another embodiment, a ligand binding domain that dimerizes with the ligand binding domain that binds Compound 1 or Compound 2 is not an ecdysone receptor ligand binding domain.

In one embodiment, the ligand binding domain that dimerizes with the ligand binding domain that binds Compound 1 or Compound 2 is a retinoic X receptor ligand binding domain. In another embodiment, the retinoic X receptor ligand binding domain is a vertebrate retinoic X receptor ligand binding domain. In another embodiment, the retinoic X receptor ligand binding domain is a *Homo sapiens* retinoic X receptor ligand binding domain. In another embodiment, the retinoic X receptor ligand binding domain is a retinoic X receptor c isoform. In another embodiment, the retinoic X receptor ligand binding domain is a retinoic X receptor 3 isoform. In another embodiment, the retinoic X receptor ligand binding domain is a retinoic X receptor γ isoform.

In another embodiment, the retinoic X receptor ligand binding domain is an invertebrate retinoic X receptor ligand binding domain. In another embodiment, the invertebrate retinoic X receptor ligand binding domain is a *Locusta migratoria* retinoic X receptor ligand binding domain.

In another embodiment, the invertebrate retinoic X receptor ligand binding domain is a non-Lepidopteran, non-Dipteran retinoic X receptor ligand binding domain.

In one embodiment, the retinoid receptor ligand binding domain is a vertebrate retinoid X receptor ligand binding domain, an invertebrate retinoid X receptor ligand binding domain, an ultraspiracle protein ligand binding domain, or a chimeric retinoid X receptor ligand binding domain.

In one embodiment, the chimeric retinoid X receptor ligand binding domain comprises two polypeptide fragments, wherein the first polypeptide fragment is from a vertebrate retinoid X receptor ligand binding domain, an invertebrate retinoid X receptor ligand binding domain, or an ultraspiracle protein ligand binding domain, and the second polypeptide fragment is from a different vertebrate retinoid X receptor ligand binding domain, a different invertebrate retinoid X receptor ligand binding domain, or a different ultraspiracle protein ligand binding domain.

In another embodiment, the chimeric retinoid X receptor ligand binding domain is one that is disclosed in U.S. Pat. No. 7,531,326, which is hereby incorporated by reference in its entirety.

In another embodiment, the first polypeptide fragment of the chimeric retinoid X receptor ligand binding domain comprises helices 1-6, helices 1-7, helices 1-8, helices 1-9, helices 1-10, helices 1-11, or helices 1-12 of a first species of retinoid X receptor, and the second polypeptide fragment of the chimeric retinoid X receptor ligand binding domain comprises helices 7-12, helices 8-12, helices 9-12, helices 10-12, helices 11-12, helix 12, or F domain of a second species of retinoid X receptor, respectively.

In another embodiment, the first polypeptide fragment of the chimeric retinoid X receptor ligand binding domain comprises helices 1-6 of a first species RXR according to the disclosure, and the second polypeptide fragment of the chimeric retinoid X receptor ligand binding domain comprises helices 7-12 of a second species of retinoid X receptor.

In another embodiment, the first polypeptide fragment of the chimeric retinoid X receptor ligand binding domain comprises helices 1-7 of a first species retinoid X receptor according to the disclosure, and the second polypeptide fragment of the chimeric retinoid X receptor ligand binding domain comprises helices 8-12 of a second species retinoid X receptor.

In another embodiment, the first polypeptide fragment of the chimeric retinoid X receptor ligand binding domain comprises helices 1-8 of a first species of retinoid X receptor, and the second polypeptide fragment of the chimeric retinoid X receptor ligand binding domain comprises helices 9-12 of a second species of retinoid X receptor.

In another embodiment, the first polypeptide fragment of the chimeric retinoid X receptor ligand binding domain comprises helices 1-9 of a first species of retinoid X receptor, and the second polypeptide fragment of the chimeric retinoid X receptor ligand binding domain comprises helices 10-12 of a second species of retinoid X receptor.

In another embodiment, the first polypeptide fragment of the chimeric retinoid X receptor ligand binding domain comprises helices 1-10 of a first species of retinoid X receptor, and the second polypeptide fragment of the chimeric retinoid X receptor ligand binding domain comprises helices 11-12 of a second species of retinoid X receptor.

In another embodiment, the first polypeptide fragment of the chimeric retinoid X receptor ligand binding domain comprises helices 1-11 of a first species of retinoid X receptor, and the second polypeptide fragment of the chimeric retinoid X receptor ligand binding domain comprises helix 12 of a second species of retinoid X receptor.

In another preferred embodiment, the first polypeptide fragment of the chimeric retinoid X receptor ligand binding domain comprises helices 1-12 of a first species of retinoid X receptor, and the second polypeptide fragment of the chimeric retinoid X receptor ligand binding domain comprises an F domain of a second species of retinoid X receptor.

In one embodiment, the first polypeptide fragment in the chimeric retinoid X receptor ligand binding domain is human retinoid X receptor sequence, and the second polypeptide fragment in the chimeric retinoid X receptor ligand binding domain is invertebrate retinoid X receptor sequence. In another embodiment, the invertebrate retinoid X receptor sequence is *Locusta migratoria* retinoid X receptor sequence.

In another embodiment, the first polypeptide fragment of the chimeric retinoid X receptor ligand binding domain comprises helices 1-8 of a human retinoid X receptor, and the second polypeptide fragment of the chimeric retinoid X receptor ligand binding domain comprises helices 9-12 of *Locusta migratoria* retinoid X receptor.

In one embodiment, the gene switch further comprises a DNA binding domain ("DBD"). In another embodiment, the DBD is selected from the group consisting of a GAL4 DBD, a LexA DBD, a transcription factor DBD, a steroid/thyroid hormone nuclear receptor superfamily member DBD, a bacterial LacZ DBD, and a yeast DBD.

In one embodiment, the gene switch further comprises a transactivation domain ("TD"). In another embodiment, the transactivation domain is selected from the group consisting of a VP16 TD, a GAL4 TD, an NF-κB TD, a BP64 TD, and a B42 acidic TD.

In one embodiment, a DNA binding domain, the ligand binding domain that binds Compound 1, a ligand binding domain that dimerizes with the ligand binding domain that binds Compound 1, and a transactivation domain are encoded by polynucleotide sequences that are contained in the same polynucleotide.

In another embodiment, a DNA binding domain, a ligand binding domain that binds Compound 1, a ligand binding domain that dimerizes with the ligand binding domain that binds Compound 1, and a transactivation domain are encoded by polynucleotide sequences that are contained in one or more separate polynucleotide sequences.

In another embodiment, a DNA binding domain, a ligand binding domain that binds Compound 1 or Compound 2, a ligand binding domain that dimerizes with the ligand binding domain that binds Compound 1 or Compound 2, and a transactivation domain are encoded by polynucleotide sequences that are contained in two separate polynucleotide sequences.

In another embodiment, a DNA binding domain and a ligand binding domain that binds Compound 1 or Compound 2 are encoded by polynucleotide sequences that are contained in a first polynucleotide sequence, and a ligand binding domain that dimerizes with the ligand binding domain that binds Compound 1 or Compound 2 and a transactivation domain are encoded by polynucleotide sequences that are contained in a second polynucleotide sequence.

In another embodiment, a DNA binding domain and a ligand binding domain that dimerizes with the ligand binding domain that binds Compound 1 or Compound 2 are encoded by polynucleotide sequences that are contained in a first polynucleotide sequence, and a ligand binding domain that binds Compound 1 or Compound 2 and a transactivation domain are encoded by polynucleotide sequences that are contained in a second polynucleotide sequence.

In embodiments in which one or more of the DNA binding domain, a ligand binding domain that binds Compound 1 or Compound 2, a ligand binding domain that dimerizes with the ligand binding domain that binds Compound 1 or Compound 2, and a transactivation domain are encoded by polynucleotide sequences that are contained in one or more separate polynucleotide sequences, then the one or more separate polynucleotide sequences is operably linked to one or more separate promoters. In another embodiment, the one or more separate polynucleotide sequences are operably linked to one or more separate enhancer elements. In another embodiment, the promoter(s) and/or the enhancer(s) are constitutively active. In another embodiment, the promoter(s) and/or the enhancer(s) are tissue specific promoters and/or enhancers.

In one embodiment, the gene switch comprises a DNA binding domain, an ecdysone receptor ligand binding domain, a ligand binding domain that dimerizes with the ecdysone receptor ligand binding domain, and a transactivation domain.

In another embodiment, the gene switch comprises a DNA binding domain, an ecdysone receptor ligand binding domain, a retinoid X receptor ligand binding domain, and a transactivation domain.

In another embodiment, the gene switch comprises a DNA binding domain, an ecdysone receptor ligand binding domain, a chimeric vertebrate/invertebrate retinoid X receptor ligand binding domain, and a transactivation domain.

In another embodiment, the gene switch comprises a GAL4 DNA binding domain, a *Choristoneura fumiferana* ecdysone receptor ligand binding domain that is engineered to contain the mutations V107I and Y127E of the *Choristoneura fumifrana* ecdysone receptor sequence set forth in SEQ ID NO: 1, a chimeric *Homo sapiens/Locusta migratoria* retinoid X receptor ligand binding, and a VP16 transactivation domain.

The term "V107I" means that the valine amino acid residue at position 107 in SEQ ID NO: 1 is changed to isoleucine. The term "Y127E" means that the tyrosine amino acid residue at position 127 in SEQ ID NO: 1 is changed to glutamate.

In another embodiment, the host cell further comprises a polynucleotide encoding a peptide, protein or polypeptide whose expression is regulated by the gene switch. A promoter that binds the gene switch complex is operably linked to the polynucleotide encoding a peptide, protein or polypeptide whose expression is regulated by the gene switch.

In another embodiment, the polynucleotide encoding a peptide, protein or polypeptide whose expression is regulated by the gene switch is contained in the same polynucleotide as a polynucleotide that encodes one or more of a DNA binding domain, the ligand binding domain that binds Compound 1 or Compound 2, a ligand binding domain that dimerizes with the ligand binding domain that binds Compound 1 or Compound 2, and a transactivation domain. Such constructs are disclosed, for example, in U.S. Patent Publication No. 2009/0123441.

In another embodiment, the polynucleotide encoding a peptide, protein or polypeptide whose expression is regulated by the gene switch is contained in a different polynucleotide than a polynucleotide that encodes one or more of a DNA binding domain, the ligand binding domain that binds Compound 1 or Compound 2, a ligand binding domain that dimerizes with the ligand binding domain that binds Compound 1 or Compound 2, and a transactivation domain.

In one embodiment, the gene switch is more sensitive to Compound 1 or Compound 2 than to a steroid hormone. In another embodiment, the gene switch is more sensitive to Compound 1 than to another diacylhydrazine compound (including Compound 2). In another embodiment, the gene switch is more sensitive to Compound 2 than to another diacylhydrazine compound (including Compound 1).

The sensitivity of a gene switch to Compound 1 or Compound 2, relative to another ligand, can readily be determined in an in vitro assay, for example, an in vitro assay that employs a reporter gene, such as firefly luciferase. Examples of such in vitro assays are well known to those of ordinary skill in the art. See, for example, Karzenowski et al., *BioTechniques* 39: 191-200 (2005).

In one embodiment, the polynucleotide encoding the gene switch is contained in a vector. In one embodiment, the vector selected from the group consisting of a plasmid, an expression vector, a replicon, a phage vector, a cosmid, a viral vector, a liposome, an electrically charged lipid (e.g., a cytofectin), a DNA-protein complex, and a biopolymer.

In another embodiment, the vector is a retroviral vector. In another embodiment, the vector is selected from the group consisting of an adeno-associated viral vector, a pox viral vector, a baculoviral vector, a vaccinia viral vector, a herpes simplex viral vector, an Epstein-Barr viral vector, an adenoviral vector, a gemini viral vector, and a caulimo viral vector.

In one embodiment, the host cell is a prokaryotic host cell. In another embodiment, the host cell is a eukaryotic host cell.

In another embodiment, the host cell is a vertebrate host cell. In another embodiment, the host cell is an invertebrate host cell.

In another embodiment, the host cell is selected from the group consisting of a bacterial cell, a fungal cell, a yeast cell, a nematode cell, an insect cell, a fish cell, a plant cell, an avian cell, an algae cell, an animal cell, and a mammalian cell.

In another embodiment, the host cell is selected from the group consisting of a zebrafish cell, a chicken cell, a hamster cell, a mouse cell, a rat cell, a rabbit cell, a cat cell, a dog cell, a bovine cell, a goat cell, a cow cell, a pig cell, a horse cell, a sheep cell, a simian cell, a monkey cell, a chimpanzee cell, and a human cell.

In another embodiment, the host cell is selected from the group consisting of an *Aspergillus* cell, a *Trichoderma* cell, a *Saccharomyces* cell, a *Pichia* cell, a *Candida* cell, a *Hansenula* cell.

In another embodiment, the host cell is selected from the group consisting of a *Synechocystis* cell, a *Synechococcus* cell, a *Salmonella* cell, a *Bacillus* cell, a *Acinetobacter* cell, a *Rhodococcus* cell, a *Streptomyces* cell, an *Escherichia* cell, a *Pseudomonas* cell, a *Methylomonas* cell, a *Methylobacter* cell, a *Alcaligenes* cell, a *Synechocystis* cell, a *Anabaena* cell, a *Thiobacillus* cell, a *Methanobacterium* cell and a *Klebsiella* cell.

In another embodiment, the host cell is selected from the group consisting of an apple cell, an *Arabidopsis* cell, a bajra cell, a banana cell, a barley cell, a bean cell, a beet cell, a blackgram cell, a chickpea cell, a chili cell, a cucumber cell, an eggplant cell, a favabean cell, a maize cell, a melon cell, a millet cell, a mungbean cell, an oat cell, an okra cell, a *Panicum* cell, a papaya cell, a peanut cell, a pea cell, a pepper cell, a pigeonpea cell, a pineapple cell, a *Phaseolus* cell, a potato cell, a pumpkin cell, a rice cell, a sorghum cell, a soybean cell, a squash cell, a sugarcane cell, a sugarbeet cell, a sunflower cell, a sweet potato cell, a tea cell, a tomato cell, a tobacco cell, a watermelon cell, a mushroom cell, and a wheat cell.

In another embodiment, the host cell is selected from the group consisting of a hamster cell, a mouse cell, a rat cell, a rabbit cell, a cat cell, a dog cell, a bovine cell, a goat cell, a cow cell, a pig cell, a horse cell, a sheep cell, a monkey cell, a chimpanzee cell, and a human cell.

Host cell transformation is well known in the art and may be achieved by a variety of methods including but not limited to electroporation, viral infection, plasmid (or vector) transfection, non-viral vector mediated transfection, *Agrobacterium*-mediated transformation, particle bombardment, and the like. Expression of desired gene products involves culturing the transformed host cells under suitable conditions and inducing expression of the transformed gene.

Culture conditions and gene expression protocols in prokaryotic and eukaryotic cells are well known in the art. Cells may be harvested and the gene products isolated according to protocols specific for the gene product.

In addition, a host cell may be chosen which modulates the expression of the inserted polynucleotide, or modifies and processes the polypeptide product in the specific fashion desired. Different host cells have characteristic and specific mechanisms for the translational and post-translational processing and modification (e.g., glycosylation, cleavage (e.g., of signal sequence)) of proteins. Appropriate cell lines or host systems can be chosen to ensure the desired modification and processing of the foreign protein expressed. For example, expression in a bacterial system can be used to produce a non-glycosylated core protein product. However, a polypeptide expressed in bacteria may not be properly folded. Expression in yeast can produce a glycosylated product. Expression in eukaryotic cells can increase the likelihood of "native" glycosylation and folding of a heterologous protein. Moreover, expression in mammalian cells can provide a tool for reconstituting, or constituting, the polypeptide's activity. Furthermore, different vector/host expression systems may affect processing reactions, such as proteolytic cleavages, to a different extent.

In one embodiment, the host cell comprises two or more orthogonal gene switches. Two or more individually operable gene regulation systems are said to be "orthogonal" when (a) modulation of each of the given gene switches by its respective ligand results in a measurable change in the magnitude of expression of the gene that is regulated by that gene switch, and (b) the change is statistically significantly different than the change in expression of all other gene switches that are in the host cell. In one embodiment, regulation of each individually operable gene switch system effects a change in gene expression at least 2-fold, 3-fold, 4-fold, 5-fold, 10-fold, 20-fold, 50-fold, 70-fold, 100-fold, 200-fold, 300 fold, 400-fold or 500-fold greater than all of the other operable gene switches in the host cell. Non-limiting examples of orthogonal gene switch systems are set forth in U.S. Patent Publication No. US 2002/0110861 A1.

In another embodiment, one or more crystalline polymorphic forms or amorphous forms of Compound 1 or Compound 2, or a composition thereof, are administered to a subject to treat cancer in the subject, for example, a cancer selected from the group consisting of myelodysplasia, breast cancer, prostate cancer, lymphoma, skin cancer, pancreatic cancer, colon cancer, melanoma, malignant melanoma, ovarian cancer, brain cancer, primary brain carcinoma, head-neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, acute myelogenous leukemia, chronic myelogenous leukemia, chronic granulocytic leukemia, acute granulocytic leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, mesothelioma, osteogenic sarcoma, primary macroglobulinemia, and retinoblastoma, and the like.

In another embodiment, one or more crystalline polymorphic forms or amorphous forms of Compound 1 or Compound 2, or a composition thereof, are administered to a subject to treat a metabolic-related disorder in the subject, for example, a metabolic disorder selected from the group consisting of dyslipidemia, atherosclerosis, insulin resistance, diabetes (e.g., diabetes type I, diabetes type II, MODY, and gestational diabetes), obesity, impaired glucose tolerance, atheromatous disease, hypertension, heart disease (which includes, but is not limited to, coronary heart disease, stroke, cardiac insufficiency, coronary insufficiency, and high blood pressure), hyperlipidemia, glucose intolerance, insulin resistance, hyperglycemia, hyperinsulinemia, metabolic syndrome X (or syndrome X, or insulin resistance syndrome, or Reaven's syndrome, or the metabolic cardiovascular risk syndrome), hypertension, chronic fatigue, accelerated aging, degenerative disease, endocrine deficiencies of aging, $G_m1$ gangliosidosis, Morquio-B disease, Krabbe's disease, Fabry's disease, Gaucher's disease, Tay-Sachs disease, Sandhoff disease, fucosidosis, disorders of carbohydrate metabolism (e.g., glycogen storage disease), disorders of amino acid metabolism (e.g., phenylketonuria, maple syrup urine disease, glutaric acidemia type 1), disorders of organic acid metabolism (e.g., alcaptonuria), disorders of fatty acid oxidation and mitochondrial metabolism (e.g., medium chain acyl dehydrogenase deficiency), disorders of porphyrin metabolism (e.g., acute intermittent porphyria), disorders of purine or pyrimidine metabolism (e.g., Lesch-Nyhan syndrome), disorders of steroid metabolism (e.g., congenital adrenal hyperplasia), disorders of mitochondrial function (e.g., Kearns-Sayre syndrome), and disorders of peroxisomal function (e.g., Zellweger syndrome).

In another embodiment, one or more crystalline polymorphic forms or amorphous forms of Compound 1 or Compound 2, or a composition thereof, are administered to a subject to treat kidney disease in the subject. In one embodiment, the kidney disease is renal failure. In another embodiment, the kidney disease is chronic renal failure.

In another embodiment, one or more crystalline polymorphic forms or amorphous forms of Compound 1 or Compound 2, or a composition thereof, are administered to a subject to treat anemia in the subject. In one embodiment, the anemia is anemia associated with kidney disease, for example, renal failure or chronic renal failure. In another embodiment, the anemia is associated with cancer therapy with, for example, one or more chemotherapeutic agents. In another embodiment, the anemia is associated with advanced age. In another embodiment, the anemia is associated with impaired lung function. In another embodiment, the anemia is associated with myelodisplasia. In another embodiment, the anemia is associated with radiation therapy. In another embodiment, the anemia is associated with a critical illness. In another embodiment, the anemia is associated with cardiac disease. In another embodiment, the anemia is not a cardiac disease. Nonlimiting types of "cardiac disease" are congestive heart failure, hypoxia, ischemic heart disease, hypertensive heart disease, coronary artery disease, peripheral vascular disease and ischemic cardiac events, e.g., myocardial infarction, heart attack, heart failure, arrhythmia, myocardial rupture, pericarditis, cardiogenic shock, thrombosis, embolism, atherosclerosis, and arterial stenosis.

In another embodiment, the one or more crystalline polymorphic forms or amorphous forms of Compound 1 or Compound 2, or a composition thereof, are administered to a subject to treat an autoimmune disorder in the subject, for example, an autoimmune disorder selected from the group consisting of Achlorhydra Autoimmune Active Chronic Hepatitis, Acute Disseminated Encephalomyelitis, Acute hemorrhagic leukoencephalitis, Addison's Disease, gamma-globulinemia, Agammaglobulinemia, Alopecia areata, Amyotrophic Lateral Sclerosis, Ankylosing Spondylitis, Anti-GBM/TBM Nephritis, Antiphospholipid syndrome, Antisynthetase syndrome, Arthritis, Atopic allergy, Atopic Dermatitis, Aplastic Anemia, Autoimmune cardiomyopathy, Autoimmune hemolytic anemia, Autoimmune hepatitis, Autoimmune inner ear disease, Autoimmune lymphoproliferative syndrome, Autoimmune peripheral neuropathy, Autoimmune pancreatitis, Autoimmune polyendocrine syndrome Types I, II, & III, Autoimmune progesterone dermatitis, Autoimmune thrombocytopenic purpura, Autoimmune uveitis, Balo disease/Balo concentric sclerosis, Bechets Syndrome, Berger's disease, Bickerstaffs encephalitis, Blau syndrome, Bullous Pemphigoid, Castleman's disease, Chronic Fatigue Immune Dysfunction Syndrome, chronic inflammatory demyelinating polyneuropathy, Chronic recurrent multifocal ostomyelitis, Churg-Strauss syndrome, Cicatricial Pemphigoid, Coeliac Disease, Cogan syndrome, Cold agglutinin disease, Complement component 2 deficiency, Cranial arteritis, CREST syndrome, Crohns Disease, Cushing's Syndrome, Cutaneous leukocytoclastic angiitis, Dego's disease, Dermatitis herpetiformis, Dermatomyositis, Diabetes mellitus type 1, Diffuse cutaneous systemic sclerosis, Dressler's syndrome, Discoid lupus erythematosus, eczema, Enthesitis-related arthritis, Eosinophilic fasciitis, Epidermolysis bullosa acquisita, Erythema nodosum, Essential mixed cryoglobulinemia, Evan's syndrome, Fibrodysplasia ossificans progressiva, Fibromyositis, Fibrosing aveolitis, Gastritis, Gastrointestinal pemphigoid, Giant cell arteritis, Goodpasture's syndrome, Graves' disease, Guillain-Barré syndrome (GBS), Hashimoto's encephalitis, Hashimoto's thyroiditis, Hemolytic anaemia, Henoch-Schonlein purpura, Herpes gestationis, Hughes syndrome (or Antiphospholipid syndrome), Hypogammaglobulinemia, Idiopathic Inflammatory Demyelinating Diseases, Idiopathic pulmonary fibrosis, Idiopathic thrombocytopenic purpura, IgA nephropathy (or Berger's disease), Inclusion body myositis, ory demyelinating polyneuopathy, Juvenile idiopathic arthritis, Juvenile rheumatoid arthritis, Lambert-Eaton myasthenic syndrome, Leukocytoclastic vasculitis, Lichen planus, Lichen sclerosus, Linear IgA disease (LAD), Lou Gehrig's Disease, Lupoid hepatitis, Lupus erythematosus, Majeed syndrome, Meniere's disease, Microscopic polyangiitis, Miller-Fisher syndrome, Mixed Connective Tissue Disease, Mucha-Habermann disease, Muckle-Wells syndrome, Multiple Myeloma, Myasthenia gravis, Myositis, Narcolepsy, Neuromyelitis optica (also Devic's Disease), Occular cicatricial pemphigoid, Ord thyroiditis, Palindromic rheumatism, PANDAS (Pediatric Autoimmune Neuropsychiatric Disorders Associated with *Streptococcus*), Paraneoplastic cerebellar degeneration, Paraneoplastic cerebellar degeneration, Parry Romberg syndrome, Parsonnage-Turner syndrome, Pars planitis, *Pemphigus, Pemphigus vulgaris*, Pernicious anaemia, Perivenous encephalomyelitis, POEMS syndrome, Polyarteritis nodosa, Polymyalgia rheumatica, Polymyositis, Primary biliary cirrhosis, psoriasis, psoriatic arthritis, Pyoderma gangrenosum, pure red cell aplasia, Rasmussen's encephalitis, Raynaud phenomenon, Relapsing polychondritis, Reiter's syndrome, Retroperitoneal fibrosis, Rheumatoid arthritis, Rheumatoid fever, Schmidt syndrome, Schnitzler syndrome, Scleritis, Sjögren's syndrome, Spondyloarthropathy, sticky blood syndrome, Still's Disease, Subacute bacterial endocarditis (SBE), Susac's syndrome, Sweet syndrome, Sydenham Chorea, Sympathetic ophthalmia, Takayasu's arteritis, Temporal arteritis, Tolosa-Hunt syndrome, Transverse Myelitis, Ulcerative Colitis, Undifferentiated connective tissue disease, Undifferentiated spondyloarthropathy, vasculitis, Wegener's granulomatosis, Wilson's syndrome, and Wiskott-Aldrich syndrome.

In another embodiment, one or more crystalline polymorphic forms or amorphous forms of Compound 1 or Compound 2, or a composition thereof, are administered to a subject to treat an ocular disorder in the subject, for example, an ocular disorder selected from the group consisting of glaucoma including Open Angle Glaucoma (e.g., Primary Open Angle Glaucoma, Pigmentary Glaucoma, and Exfoliative Glaucoma, Low Tension Glaucoma), Angle Closure Glaucoma (also known clinically as closed angle glaucoma, narrow angle glaucoma, pupillary block glaucoma, and ciliary block glaucoma) (e.g., Acute Angle Closure Glaucoma and Chronic Angle Closure Glaucoma), Aniridic Glaucoma, Congenital Glaucoma, Juvenile Glaucoma, Lens-Induced Glaucoma, Neovascular Glaucoma (e.g., using vectors composed of Vascular Endothelial Growth Factor (VEGF) decoy, Pigment Derived Growth Factor (PDGF), Endostatin, Angiostatin, or Angiopoetin-1), Post-Traumatic Glaucoma, Steroid-Induced Glaucoma, Sturge-Weber Syndrome Glaucoma, and Uveitis-Induced Glaucoma, diabetic retinopathy (e.g., using vectors composed of VEGF decoy, PDGF, Endostatin, Angiostatin, or Angiopoetin-1), macular degeneration (e.g., vectors composed of VEGF decoy, PDGF, Endostatin, Angiostatin, Angiopoetin-1, ATP Binding Casette Subfamily A Member 4), macular degeneration (e.g., using vectors composed of VEGF decoy, PDGF, Endostatin, Angiostatin, Angiopoetin-1, ATP Binding Casette Subfamily A Member 4), choroidal neovascularization, (e.g., using vectors composed of VEGF decoy, PDGF, Endostatin, Angiostatin, or Angiopoetin-1), vascular leak, and/or retinal edema, bacterial conjunctivitis, fungal conjunctivitis, viral conjunctivitis, uveitis, keratic precipitates, macular edema (e.g., using vectors composed of VEGF decoy, PDGF, Endostatin, Angiostatin, or Angiopoetin-1), inflammation response after intra-ocular lens implantation, uveitis syndromes (for example, chronic iridocyclitis or chronic endophthalmitis), retinal vasculitis (for example, as seen in rheumatoid arthritis, juvenile rheumatoid arthritis, systemic lupus erythymatosus, progressive systemic sclerosis, polyarteritis nodosa, Wegener's granulomatosis, termporal arteritis, Adamantiades Bechcet disease, Sjorgen's, relapsing polychondritis and HLA-B27 associated spondylitis), sarcoidosis, Eales disease, acute retinal necrosis, Vogt Koyanaki Harada syndrome, occular toxoplasmosis, radiation retinopathy, proliferative vitreoretinopathy, endophthalmitis, ocular glaucomas (for example, inflammatory glaucomas), optic neuritis, ischemic optic neuropathy (e.g., vectors composed of Allotopic NADH dehydrogenase Unit 4), thyroid associated orbitopathy, orbital pseudotumor, pigment dispersion syndrome (pigmentary glaucoma), scleritis, episcleritis choroidopathies (for example, "White-dot" syndromes including, but not limited to, acute multifocal posterior placoid), retinopathies (for example, cystoid macular edema, central serous choroidopathy and presumed ocular histoplasmosis syndrome (e.g., vectors composed of Glial Cell Derived Neurotropic Factor, Peripherin-2)), retinal vascular disease (for example, diabetic retinopathy, Coat's disease and retinal arterial macroaneurysm), retinal artery occlusions, retinal vein occlusions, retinopathy of prematurity, retinitis pigmentosa (e.g., vectors composed of Retinal Pigment Specific 65 kDa protein), familial exudative vitreoretinopathy (FEVR), idiopathic polypoidal choroidal vasculopathy, epiretinal macular membranes and cataracts.

In another embodiment, one or more crystalline polymorphic forms or amorphous forms of Compound 1 or Compound 2, or a composition thereof, are administered to a subject to treat a blood disorder in the subject, for example, a blood disorder selected from the group consisting of a blood disorder selected from the group consisting of anemia, bleeding and clotting disorders (e.g., disseminated intravascular coagulation (DIC), hemophilia, Henoch-Schonlien Purpura, hereditary hemorrhagic telangiectasia, thrombocytopenia (ITP, TTP), thrombophilia, Von Willebrand's disease), leukemias (e.g., acute lymphocytic leukemia, acute myelocytic leukemia, chronic lymphocytic leukemia, chronic myelocytic leukemia), lymphomas (e.g., Hodgkin lymphoma, non-Hodgkin lymphoma), myeloproliferative disorders (e.g., myelofibrosis, Polycythemia Vera, thrombocythemia), plasma cell disorders (e.g., macroglobulinemia, monoclonal gammopathies of undetermined significance, multiple lyeloma), spleen disorders, white blood cell disorders (e.g., basophilic disorder, eosinophilic disorder, lymphocytopenia, monocyte disorders, neutropenia, neutrophillic leukocytosis), thrombosis, deep vein thrombosis (DVT), hemochromatosis, menorrhagia, sickle cell disease, and thalassemia.

In another embodiment, one or more crystalline polymorphic forms or amorphous forms of Compound 1 or Compound 2, or a composition thereof, are administered to a subject to treat a neurological disorder in the subject, for example, a neurological disorder selected from the group consisting of Gaucher disease, Parkinson's disease, Alzheimer's disease, amyotrophic lateral sclerosis (ALS), multiple sclerosis (MS), Huntington's disease, Fredrich's ataxia, Mild Cognitive Impairment, Cerebral Amyloid Angiopathy, Parkinsonism Disease, Lewy Body Disease, Frontotemporal Dementia (FTD) Multiple System Atrophy (MSA), Progressive Supranuclear Palsy, and movement disorders (including ataxia, cerebral palsy, choreoathetosis, dystonia, Tourette's syndrome, kernicterus) and tremor disorders, and leukodystrophies (including adrenoleukodystrophy, metachromatic leukodystrophy, Canavan disease, Alexander disease, Pelizaeus-Merzbacher disease), neuronal ceroid lipofucsinoses, ataxia telangectasia, Rett Syndrome, alpha.-synucleinopathy (e.g., Lewy Body Disease, Multiple System Atrophy, Hallervorden-Spatz disease, or Frontotemporal Dementia), Niemann-Pick Type C disease (NPCD), spinocerebellar ataxia Type 1, Type 2, and Type 3, and dentatorubral pallidoluysian atrophy (DRLPA).

In another embodiment, one or more crystalline polymorphic forms or amorphous forms of Compound 1 or Compound 2, or a composition thereof, are administered to a subject to treat a lung disorder in the subject, for example, a lung disorder selected from the group consisting of asthma, atelectasis, bronchitis, COPD (chronic obstructive pulmonary disease), emphysema, Lung cancer, mesothelioma, pneumonia, asbestosis, Aspergilloma, Aspergillosis, Aspergillosis—acute invasive, bronchiectasis, bronchiolitis obliterans organizing pneumonia (BOOP), eosinophilic pneumonia, necrotizing pneumonia, ral effusion, pneumoconiosis, pneumothorax, pulmonary actinomycosis, monary alveolar proteinosis, pulmonary anthrax, pulmonary arteriovenous malformation, pulmonary fibrosis, pulmonary embolus, pulmonary histiocytosis X (eosinophilic granuloma), pulmonary hypertension, pulmonary edema, pulmonary hemorrhage, pulmonary nocardiosis, pulmonary tuberculosis, pulmonary veno-occlusive disease, rheumatoid lung disease, sarcoidosis, radiation fibrosis, hypersensitivity pneumonitis, acute respiratory distress syndrome (ARDS), infant respiratory distress syndrome, idiopathic pulmonary fibrosis, idiopathic interstitial pneumonia, lymphangioleiomyomatosis, pulmonary Langerhans' cell histiocytosis, pulmonary alveolar proteinosis, sinusitis, tonsillitis, otitis media, pharyngitis, laryngitis, Pulmonary hamartoma, pulmonary sequestration, congenital cystic adenomatoid malformation (CCAM), and cystic fibrosis.

In another embodiment, one or more crystalline polymorphic forms or amorphous forms of Compound 1 or Compound 2, or a composition thereof, are administered to a subject to treat a rheumatologic disorder in the subject, for example, a rheumatologic disorder selected from the group consisting of systemic lupus erythematosus, dermatomyositis, scleroderma, systemic necrotizing arteritis, cutaneous necrotizing venulitis, rheumatoid arthritis, Sjogren's Syndrome, Raynaud's phenomenon, Reiter's syndrome, arthritis, psoriatic arthritis, seronegative spondyloarthropathies, Sjogren's syndrome, systemic sclerosis, dermatomyositis/polymyositis, mixed connective tissue disease, and ankylosing spondylitis.

In another embodiment, one or more crystalline polymorphic forms or amorphous forms of Compound 1 or Compound 2, or a composition thereof, are administered a subject to treat an infectious disease in the subject, for example, an infectious disease selected from the group consisting of fungal diseases such as dermatophytosis (e.g., trichophytosis, ringworm or tinea infections), athletes foot, paronychia, *pityriasis versicolor*, erythrasma, intertrigo, fungal diaper rash, *candida* vulvitis, *candida* balanitis, otitis externa, candidiasis (cutaneous and mucocutaneous), chronic mucocandidiasis (e.g., thrush and vaginal candidiasis), cryptococcosis, geotrichosis, trichosporosis, aspergillosis, penicilliosis, fusariosis, zygomycosis, sporotrichosis, chromomycosis, coccidioidomycosis, histoplasmosis, blastomycosis, paracoccidioidomycosis, pseudallescheriosis, mycetoma, mycotic keratitis, otomycosis, pneumocystosis, and fungemia, *Acinetobacter* infections, Actinomycosis, African sleeping sickness, AIDS (Acquired immune deficiency syndrome), Amebiasis, Anaplasmosis, Anthrax, Arcanobacterium haemolyticum infection, Argentine hemorrhagic fever, Ascariasis, Aspergillosis, atrovirus infection, Babesiosis, *Bacillus cereus* infection, Bacterial pneumonia, Bacterial vaginosis (BV), *Bacteroides* infection, Balantidiasis, *Baylisascaris* infection, BK virus infection, Black piedra, *Blastocystis hominis* infection, *Borrelia* infection, Botulism (and Infant botulism), Brazilian hemorrhagic fever, Brucellosis, *Burkholderia* infection, Buruli ulcer, Calcivirus infection (Norovirus and Sapovirus), Candidiasis, Cat-scratch disease, Cellulitis, Chagas Disease (American trypanosomiasis), Chancroid, Chickenpox, *Chlamydia*, Cholera, Chromoblastomycosis, Clonorchiasis, *Clostridium difficile*, Coccidioidomycosis, Colorado tick fever (CTF), Common cold (Acute viral rhinopharyngitis; Acute coryza), Creutzfeldt-Jakob disease (CJD), Cryptococcosis, Cryptosporidiosis, ous larva migrans (CLM), Dengue fever, Dientamoebiasis, Diphtheria, Diphyllobothriasis, Diphyllobothriasis, Dracunculiasis, Ebola hemorrhagic fever, Echinococcosis, Ehrlichiosis, Enterobiasis (Pinworm infection), *Enterococcus* infection, Enterovirus infection, Epidemic typhus, Erythema infectiosum, Exanthem subitum, Fasciolopsiasis, Fasciolosis, Fatal familial insomnia (FFI), Filariasis, *Fusobacterium* infection, Gas gangrene (Clostridial myonecrosis), Geotrichosis, Gerstmann-Straussler-Scheinker syndrome (GSS), Giardiasis Glanders, Gnathostomiasis, Gonorrhea, Granuloma inguinale (Donovanosis), Group A streptococcal infection, Group B streptococcal infection, *Haemophilus influenzae*, Hand, foot and mouth disease (HFMD), Hantavirus Pulmonary Syndrome (HPS) *Helicobacter pylori* infection, ic-uremic syndrome (HUS), Hemorrhagic fever with renal syndrome (HFRS), Hepatitis A, B, C, D, E, Herpes simplex, Histoplasmosis, Hookworm infection, n bocavirus infection, Human ewingii ehrlichiosis, Human granulocytic anaplasmosis (HGA), Human granulocytic anaplasmosis (HGA), Human monocytic ehrlichiosis, Human papillomavirus (HPV) infection, Human parainfluenza virus infection, Hymenolepiasis, Epstein-Barr Virus Infectious Mononucleosis (Mono), Influenza (flu), Isosporiasis, Kawasaki disease, Keratitis, Kingella kingae infection, Kuru, Lassa fever, Legionellosis (Legionnaires' disease), Legionellosis (Pontiac fever), Leishmaniasis, Leprosy, Leptospirosis, Listeriosis, Lyme disease (Lyme borreliosis), Lymphatic filariasis (Elephantiasis), Lymphocytic choriomeningitis, Malaria, Marburg hemorrhagic fever (MHF), Measles, Melioidosis (Whitmore's disease), Meningitis, Meningococcal disease, Metagonimiasis, Microsporidiosis, Molluscum contagiosum (MC), Mumps, Murine typhus (Endemic typhus), Mycoplasma pneumonia, Mycetoma, Myiasis, Neonatal conjunctivitis (Ophthalmia neonatorum), (New) Variant Creutzfeldt-Jakob disease (vCJD, nvCJD), Nocardiosis, Onchocerciasis (River blindness), Paracoccidioidomycosis (South American blastomycosis), Paragonimiasis, Pasteurellosis, *Pediculosis capitis* (Head lice), *Pediculosis corporis* (Body lice), *Pediculosis pubis* (Pubic lice, Crab lice), Pelvic inflammatory disease (PID), Pertussis (Whooping cough), Plague, Pneumococcal infection, Pneumocystis pneumonia (PCP), Pneumonia, Poliomyelitis, Poliomyelitis, Prevotella infection, mary amoebic meningoencephalitis (PAM), Progressive multifocal leukoencephalopathy, Psittacosis, Q fever, Rabies, Rat-bite fever, Respiratory syncytial virus infection, Rhinosporidiosis, inovirus infection, Rickettsial infection, Rickettsialpox, Rift Valley fever (RVF), Rocky mountain spotted fever (RMSF), Rotavirus infection, Rubella, Salmonellosis, SARS (Severe Acute Respiratory Syndrome), Scabies, Schistosomiasis, Sepsis, Shigellosis (Bacillary dysentery), Shingles (Herpes zoster), Smallpox (Variola), Sporotrichosis, Staphylococcal food poisoning, Staphylococcal infection, Strongyloidiasis, Syphilis, Taeniasis, tanus (Lockjaw), *Tinea barbae* (Barber's itch), *Tinea capitis* (Ringworm of the Scalp), *Tinea corporis* (Ringworm of the Body), *Tinea cruris* (Jock itch), *Tinea manuum* (Ringworm of the Hand), *Tinea nigra, Tinea unguium* (Onychomycosis), *Tinea versicolor* (*Pityriasis versicolor*), Toxocariasis (Visceral Larva Migrans (VLM)), Toxoplasmosis, Trichinellosis, Trichomoniasis, Trichuriasis (Whipworm infection), Tuberculosis, Tularemia, *Ureaplasma urealyticum* infection, Venezuelan equine encephalitis, Venezuelan hemorrhagic fever, viral pneumonia, West Nile Fever, White piedra (*Tinea blanca*), Yersiniapseudotuberculosis infection, Yersiniosis, Yellow fever, and Zygomycosis.

In another embodiment, one or more crystalline polymorphic forms or amorphous forms of Compound 1 or Compound 2, or a composition thereof, are administered to a subject to treat angioedema in the subject. In another embodiment, the angioedema is hereditary angioedema.

In another embodiment, one or more crystalline polymorphic forms or amorphous forms of Compound 1 or Compound 2, or a composition thereof, are administered to a subject treat a disease, condition or disorder selected from the group consisting of sepsis, hypercoagulability, pulmonary dysfunction, hypoxemia, hemorrhagic pancreaitis, myocardial infarction, lung transplantation, trauma, thermal injury and vascular leak in the subject.

In another embodiment, one or more crystalline polymorphic forms of Compound lor Compound 2, or a composition thereof, are administered to a subject to treat a disease, condition or disorder in which inhibition of kallikrein provides a therapeutically beneficial effect. Examples of such diseases, conditions or disorders include, but are not limited to, disease, conditions or disorders of the contact system. See e.g., Shariat-Madar et al., *Innate Immunity*, vol. 10, no. 1, 3-13 (2004) and Frick, et al., *EMBO J.*, (2006) 25, 5569-5578 (2006). In another embodiment, one or more crystalline polymorphic forms or amorphous forms of Compound 1 or Compound 2, or a composition thereof, are administered a subject to treat a disease, condition or disorder selected from the group consisting of atherothrombosis, coronary artery disease, Alzheimer's Disease, inflammatory bowel disease (for example, Crohn's Disease), vascular leak, acute respiratory distress syndrome and bradykinin-mediated inflammation in the subject.

In another embodiment, one or more crystalline polymorphic forms or amorphous forms of Compound 1 or Compound 2, or a composition thereof, are administered to a subject to treat a disease, condition or disorder in which inhibition of bradykinin B2 receptor provides a therapeutically beneficial effect. In another embodiment, one or more crystalline polymorphic forms or amorphous forms of Compound 1 or Compound 2, or a composition thereof, are administered to a subject treat a disease, condition or disorder selected from the group consisting of glomerulosclerosis, Alzheimer's Disease, cerebral edema, vascular leak, acute respiratory distress syndrome, pain, inflammation, trauma, burns, shock, allergy, and cardiovascular disease in the subject.

In another embodiment, one or more crystalline polymorphic forms or amorphous forms of Compound 1 or Compound 2, or a composition thereof, are administered to a subject to treat an infectious disease in the subject, for example, an infectious disease selected from the group consisting of Bovine respiratory disease, Porcine respiratory disease, Avian influenza, Avian infectious bronchitis, Bovine spongiform encephalopathy, Canine leishmaniasis, Chronic wasting disease, human immune deficiency virus (HIV), hepatitis, hepatitis A, hepatitis B, hepatitis C, Classical swine fever, *Echinococcus*, Enzootic pneumonia, FIP, Foot-and-mouth disease, Jaagsiekte, Maedi-Visna, Mastitis in animals, *Microsporum canis*, Orf (animal disease), Peste des petits ruminants, Pox diseases, Psittacine beak and feather disease, Rabies, Mediterranean fever (Brucellosis) or Bang's disease or undulant fever, Malta fever, contagious abortion, epizootic abortion, *Salmonella* food poisoning, enteric paratyphosis, Bacillary dysentery, Pseudotuberculosis, plague, pestilential fever, Tuberculosis, Vibrios, Circling disease, Weil's disease (Leptospirosis) or canicola fever, Hemorrhagic jaundice (Leptospira icterohaemorrhagiae), dairy worker fever (*L. hardjo*), Relapsing fever, tick-borne relapsing fever, spirochetal fever, vagabond fever, famine fever, Lyme arthritis, Bannworth's syndrome (lime disease), tick-borne meningopolyneuritis, erythema chronicum migrans, Vibriosis, Colibacteriosis, colitoxemia, white scours, gut edema of swine, enteric paratyphosis, Staphylococcal alimentary toxicosis, staphylococcal gastroenteritis, Canine Corona Virus (CCV) or canine parvovirus enteritis, feline infectious peritonitis virus, transmissible gastroenteritis (TGE) virus, Hagerman Redmouth Disease (ERMD), Infectious Hematopoietic necrosis (IHN), porcine *Actinobacillus* (*Haemophilus*) pleuropneumonia, Hansen's disease, Streptotrichosis, Mycotic Dermatitis of Sheep, Pseudoglanders, Whitmore's disease, Francis' disease, deerfly fever, rabbit fever, O'Hara disease, Streptobacillary fever, Haverhill fever, epidemic arthritic erythema, sodoku, Shipping or transport fever, hemorrhagic septicemia, Ornithosis, Parrot Fever, Chlamydiosis, North American blastomycosis, Chicago disease, Gilchrist's disease, Cat Scratch Fever, Benign Lymphoreticulosis, Benign nonbacterial Lymphadenitis, Bacillary Angiomatosis, Bacillary Peliosis Hepatis, Query fever, Balkan influenza, Balkan grippe, abattoir fever, Tick-borne fever, pneumorickettsiosis, American Tick Typhus, Tick-borne Typhus Fever, Vesicular Rickettsiosis, Kew Gardens Spotted Fever, Flea-borne Typhus Fever, Endemic Typhus Fever, Urban Typhus, Ringworm, Dermatophytosis, *Tinea*, Trichophytosis, Microsporosis, Jock Itch, Athlete's Foot, *Sporothrix schenckii*, dimorphic fungus, Cryptococcosis and histoplasmosis, Benign Epidermal Monkeypox, BEMP, Herpesvirus simiae, Simian B Disease, Venezuelan equine encephalitis, Type C lethargic encephalitis, Yellow fever, Black Vomit, hantavirus pulmonary syndrome, Korean Hemorrhagic Fever, Nephropathia Epidemica, Epidemic Hemorrhagic Fever, Hemorrhagic Nephrosonephritis, lymphocytic choriomeningitis, California encephalitis/La crosse encephalitis, African Hemorrhagic Fever, Green or Vervet Monkey Disease, Hydrophobia, Lyssa, Infectious hepatitis, Epidemic hepatitis, Epidemic jaundice, Rubeola, Morbilli, Swine and Equine Influenza, Fowl Plague, Newcastle disease, Piroplasmosis, toxoplasmosis, African Sleeping Sickness, Gambian Trypanosomiasis, Rhodesian Trypanosomiasis, Chagas's Disease, Chagas-Mazza Disease, South American Trypanosomiasis, *Entamoeba histolytica*, Balantidial dysentery, cryptosporidiosis, giardiasis, Cutaneous leishmaniasis: Chiclero ulcer, espundia, pianbols, uta, and buba (in the Americas); oriental sore, Aleppo boil (in the Old World); Bagdad boil, Delhi boil, Bauru ulcer, Visceral leishmaniasis: kala-azar, Microsporidiosis, Anisakiasis, Trichinosis, Angiostrongylosis, eosinophilic meningitis or meningoencephalitis (*A. cantonensis*), abdominal angiostrongylosis (*A. costaricensis*), Uncinariasis, Necatoriasis, Hookworm Disease, Capillariasis, Brugiasis, Toxocariasis, Oesophagostomiasis, Strongyloidiasis, Trichostrongylosis, Ascaridiasis, Diphyllobothriasis, Sparganosis, Hydatidosis, Hydatid Disease, *Echinococcus granulosis*, Cystic hydatid disease, Tapeworm Infection, and Schistosoma.

In another embodiment, one or more crystalline polymorphic forms or amorphous forms of Compound 1, or Compound 2 or a composition thereof, are administered to a subject to treat chronic renal disease, osteoarthritis, oncology, viral upper respiratory infection, feline plasma cell stomatitis, feline eosinophillic granulomas, feline leukemia virus infection, canine distemper infection, systemic fungal infections, cardiomyopathy, and mucopolysaccharidosis VII in the subject.

In the methods of the present disclosure, the gene switch regulates the expression of a polynucleotide encoding a peptide, protein, or polypeptide of interest. In one embodiment, gene switch regulates the expression of a polynucleotide encoding a peptide, protein, or polypeptide of therapeutic interest for the treatment of a disease, condition, or disorder in a subject, e.g., a human. In another embodiment, the peptide, protein or polypeptide of interest is selected from the group consisting of Her-2/neu (ERBB2/c-erbB-2), Osteocalcin, stromelysin-1, prostate specific antigen, human sodium-iodide symporter, H19, IF-1, IGF-2, thymosin β15, T cell factor, cartilage-derived retinoic acid-sensitive protein, Prostasin, telomerase catalytic subunit, cyclin-A, midkine; c-erbB-2, prostate-specific membrane antigen, p51, telomerase RNA, prostatic acid phosphatase, PCA3dd3, DF3/MUC1, hex II, cyclooxygenase-2, super PSA, skp2, PRL-3, CA125/M17S2, IAI.3B, CRG-L2, TRPM4, RTVP, TARP, telomere reverse transcriptase, A4 amyloid protein, amyloid β-protein precursor, precursor of the Alzheimer's Disease A4 amyloid protein, neuropeptide FF, endoplasmic reticulum stress elements, urocortin II, tyrosine hydroxylase, complement factor 3; serum amyloid A3, tissue inhibitor of metalloproteinase-3 (TIMP-3), p75 tumor necrosis factor receptor, tumor necrosis factor-α, TRPM4, RTVP, TARP, telomere reverse transcriptase, A4 amyloid protein, amyloid β-protein precursor, precursor of the Alzheimer's Disease A4 amyloid protein, neuropeptide FF, endoplasmic reticulum stress elements, urocortin II, tyrosine hydroxylase, complement factor 3; serum amyloid A3, tissue inhibitor of metalloproteinase-3 (TIMP-3), p75 tumor necrosis factor receptor, tumor necrosis factor-α, peroxisome proliferator activated receptor/IIA-1 nonpancreatic secreted phospholipase A2, SOCS-3, SR-BI, Ob, site-1 protease, TIGR, VL30, excitatory amino acid transporter-2, MDTS9, LIM, pyrroline 5-carboxylate reductase, SIM2, Bax, Fas, bbc3, PINK-1, troponin T, myoD, Actin, smooth muscle 22a, Utrophin, Myostatin, smooth muscle myosin heavy chain, cardiac ankyrin repeat protein, MLP, Smoothelin, MYBPC3, Tα1 α-tubulin, intercellular adhesion molecule-4 (ICAM-4), γ-aminobutyric acid type A receptor β1 subunit, neuronal nicotinic acetylcholine receptor β2-subunit, presenilin-1, calcium-calmodulin-dependent kinase IIa, CRF2a receptor, nerve growth factor, GLP-2 receptor, type I transglutaminase, K14, stearoyl-CoA desaturase, Megsin, Prolactin, GDF-9, PSP94, NRL, NGAL, long whey acidic protein, mammary associated amyloid A, endothelin-1, Serglycin, platelet-endothelial cell adhesion molecule-1 (PECAM-1), Tie receptor tyrosine kinase, KDR/flk-1, Endoglin, CCR5, CD11d, platelet glycoprotein IIb, preproendothelin-1, interleukin-18 binding protein, CD34, Tec tyrosine kinase, MLH1, MSH2, MSH6, PMS1, APC, LEF-1, F2 receptor, TGF-β type II receptor, EYA4, PCA3, K2, PROST 03, PCAM-1, PCADM-1, PCA3dd3, PCAV, PAcP, ATBo, CSA-1, SYG972, Urb-ctf, BCU399, TBX2, Cyr61, DIAPH3, BEHAB, IL-8, BLSA, BP1, DAP-kinase, HOXA9, ARP, Nbk, CD43, β7-hcG, β6-hCG, β6e-hCG, β5-hCG, β8-hcG, β3-hCG, MTAls, Old-35, Old-64, LAGE-1, CIF150/hTAFII150, P65 oncofetal protein, Telomerase, CYP1B1, 14-3-30, NES1, CAR-1, HMGI, MAG, ELL2, Ephrin B2, WAF1, CIF130, C35, BMP2, BUB3, Polymerase kappa, EAG1, EAG2, HMG I, HLTF, Barx2, Pp 32rl, BMP4, TS10q23.3, Nuclear spindle-associating protein, PFTAIRE, SEMA3B, MOGp, Fortilin, IGFBP-3, Polyhomeotic 2, PNQALRE, SCN5A, miR15, miR16, Headpin, PAOhl/SMO, Hippo, Mst2, PSMA-like, JAB 1, NF-AT, P28ING5, MTG16, ErbB-2, HDAC9, GPBP, MG20, KLF6, ARTS1, Dock 3, Annexin 8, MH15, DELTA-N p73, RapR6, StarD10, Cizl, HLJ1, RapR7, A34, Sef, Killin, SGA-1M, TGFβ Type II receptor, GCA-associated genes, PRV-1, Vezfl, MLP, VEGI, PRO256, AOP2, Remodelin, Phosphodiesterase 4D, Prostaglandin receptor subtype EP3, CARP, HOP, PLTP, UCP-2, FLJ11011, Codanin-1, Resistin, Archipelin, Neuronatin, Ncb5or, 7B2, PTHrP, PEX, KChIP1, SLIT-3, CX3CR1, SMAP-2, IC-RFX, E2IG4, UCP2, Ob receptor, Ob, Dpl, NRG-1, Synapsin III, NRG1AG1, AL-2, Proline dehydrogenase, MNR2, ATM, Ho-1, CON202, Ataxin-1, NR3B, NIPA-1, DEPP, adrenomedullin, csdA, Inf-20, EOPA, SERT, FRP-1, Serum amyloid A, BMP2, BMPRIA, ACLP, Resistin-like molecule J3, Dlg5, TRANCE, Matrilin-3, Synoviolin, HIV LTR, SHIVA, EBI 1, EBI 2, EBI 3, NM23, Eps8, Beta-10, Hair follicle growth factor, Corneodesmosin, GCR9, Bg, FGF23, BBSR, MIC-1, MIA-2, IL-17B, Formylglycine generating enzyme, LPLA2, CXCL1O, HFE2A, IL-1, IL-2, IL-3, IL-4, IL-5, IL-7, IL-8, IL-9, IL-10R DN or a subunit thereof, IL-15, IL-18, IL-21, IL-23, IL-24, IL-27, GM-CSF, IFN-alpha, IFN-gamma, IFN-alpha 1, IFN alpha 2, IL-15-R-alpha, CCL3 (MIP-1a), CCL5 (RANTES), CCL7 (MCP3), XCL1 (lymphotactin), CXCL1 (MGSA-alpha), CCR7, CCL19 (MIP-3b), CXCL9 (MIG), CXCL10 (IP-10), CXCL12 (SDF-1), CCL21 (6Ckine), OX40L, 4-1BBL, CD40, CD70, GITRL, LIGHT, b-Defensin, HMGB1, Flt3L, IFN-beta, TNF-alpha, dnFADD, BCG, TGF-alpha, PD-L1 RNAi, a PD-L1 antisense oligonucleotide, TGFbRII DN, ICOS-L, S100, CD40L, p53, survivin, p53-survivin fusion, MAGE3, myelin basic protein, PSA and PSMA.

In another embodiment, the gene switch regulates the expression of a polynucleotide encoding an IL-12 or a subunit thereof. In another embodiment, the IL-12 or subunit thereof is human IL-12 or subunit thereof.

In another embodiment, the gene switch regulates the expression of a polynucleotide encoding a C1 esterase inhibitor (for example, a human C1 esterase inhibitor), a kallikrein inhibitor, or a bradykinin B2 receptor antagonist.

Examples of kallikrein inhibitors include, but are not limited to, ecallantide and those kallikrein inhibitors set forth U.S. Patent Publication Nos. 2010/0034805, 2009/0264350, 2009/0234009, 2008/0221031, 2007/0213275, 2006/0264603 and 2005/0089515.

Examples of bradykinin B2 receptor inhibitors include, but are not limited to, helokinestatin and anti-bradykinin B2 receptor antibodies. The amino acid sequence of helokinestatin is Gly-Pro-Pro-Tyr-Gln-Pro-Leu-Val-Pro-Arg (SEQ ID NO: 2) (Kwok, H. F. et al., *Peptides* 29I 65-72 (2008), which is incorporated by reference in its entirety). Nonlimiting examples of anti-bradykinin B2 receptor antibodies are set forth in Alla, S. A. et al., *J. Biol. Chem.* 271: 1748-1755 (1996).

In another embodiment, the gene switch regulates the expression of a polynucleotide encoding an IL-12 or a subunit thereof for the treatment of cancer, e.g., melanoma, in a subject, e.g., a human.

In another embodiment, a polynucleotide encodes (a) a gene switch that comprises a GAL4 DNA binding domain, the *Choristoneura fumiferana* ecdysone receptor ligand binding domain having the mutations V107I and Y127E (relative to SEQ ID NO: 1), a chimeric RXR ligand binding domain consisting of helices 1-8 of *Homo sapiens* RXR and helices 9-12 of *Locusta migratoria* RXR, the VP16 transactivation domain, and (b) human IL-12, and the gene switch encoded by the polynucleotide regulates the expression of human IL-12 when the ecdysone receptor ligand binding domain in the gene switch binds Compound 1 or Compound 2. In a further embodiment, the polynucleotide is administered to a subject having a cancer such as melanoma. The polynucleotide may be administered intratumorally either in a pharmaceutically acceptable carrier, or contained by an immune cell such as a dendritic cell. In one embodiment, the polynucleotide is administered to a subject followed by administration of one or more polymorphic forms of Compound 1, or composition thereof. In another embodiment, one or more polymorphic forms of Compound 1, or composition thereof, is administered to a subject followed by administration of the polynucleotide. For example, one or more polymorphic forms or amorphous forms of Compound 1, or composition thereof, may be administered to the subject on day −1, 0, +1, +2, +3, +4, +5, +6, +7, or more, relative to the day the polynucleotide is administered to the subject.

In another embodiment, the gene switch regulates the expression of a polynucleotide encoding a transcription factor, e.g., GATA-1, friend of GATA (FOG-1), EKLF (a Kruppel-like transcription factor), p45/nuclear factor-erythroid 2 (NF-E2), stem cell leukemia (SCL) or T-cell acute lymphocytic leukemia-1, OCT4, or Sry-related high-mobility group box transcription factor (Sox6), or growth factor, e.g., IGFII, bFGF, Flt3, stem cell factor (SCF), thrombopoietin (TPO), bone morphogenetic protein 4 (BMP4), recombinant human vascular endothelial growth factor (VEGF-A165), interleukin-3 (IL-3) interleukin-6 (IL-6), or interleukin-11 (IL-11), or erythropoietin, for use in regenerative medicine, e.g., differentiation, trans-differentiation, reprogramming, self-renewal, or expansion of hematopoietic stem cells, haematopoietic progenitor cells, or induced pluripotent stem cells in the process of blood pharming, i.e., production of red blood cells or other blood products, in a subject.

EXAMPLES

Instrumentation—Typical Measurement Conditions

Powder X-Ray Diffraction (PXRD)
Bruker D8 Advance diffractometer in Bragg-Brentano reflection geometry; Cu Kα radiation, 40 kV/40 mA; variable divergence slit; LynxEye detector with 30 window; step size, 0.02° 2θ; step time, 37 s; scanning range 2-50° in 2θ. The samples were rotated (0.5 rps) during the measurement and prepared without any special treatment other than slight pressure to get a flat surface. The measurement was performed under ambient laboratory conditions in a silicon single crystal sample holder, 0.1- or 1-mm deep.
FT-Raman Spectroscopy:
Bruker RFS 100 FT-Raman system; FT-Raman spectra were recorded with a NIR Nd:YAG laser operating at 1064 nm and a liquid-nitrogen cooled germanium detector; 300 mW nominal laser power; 64 scans with resolution 2 cm-1; sample measured in an aluminum sample holder under ambient laboratory conditions.
Differential Scanning Calorimetry (DSC):
Perkin Elmer DSC7; closed gold crucibles filled under nitrogen atmosphere; heating rate 10° C./min.
Dynamic Vapor Sorption (DVS):
Projekt Messtechnik SPS 11-100n multi-sample water vapor sorption analyzer or Surface Measurement Systems Ltd. DVS-1 water vapour sorption analyzer. The sample was allowed to equilibrate at 50% r.h. before starting a predefined humidity program.
Program: 50% r.h.→0% r.h.→95% r.h.→50% r.h., Δr.h.=5%/h
Hygroscopicity was classified as follows:
deliquescent sufficient water is absorbed to form a liquid
very hygroscopic increase of the mass is ≥15%
hygroscopic increase of the mass is less than 15% and greater than or equal to 2%
slightly hygroscopic increase of the mass is less than 2% and greater than or equal to 0.2%
not hygroscopic increase of the mass is less than 0.2%
Thermogravimetry Coupled to Fourier-Transform Infrared Spectroscopy (Tg-Ftir):

Netzsch Thermo-Microbalance TG 209 coupled to a Bruker Vector 22 FTIR spectrometer; aluminum crucible with a pinhole, measurement under N2 atmosphere, heating rate 10° C./min.

Example 1

(R)-3,5-dimethyl-benzoic acid N-(1-tert-butyl-butyl)-N'-(2-ethyl-3-methoxy-benzoyl)-hydrazide (Compound 1)

Compound 1 was prepared according to Scheme 1 as described in US 2009/0163592 (see Example 1).

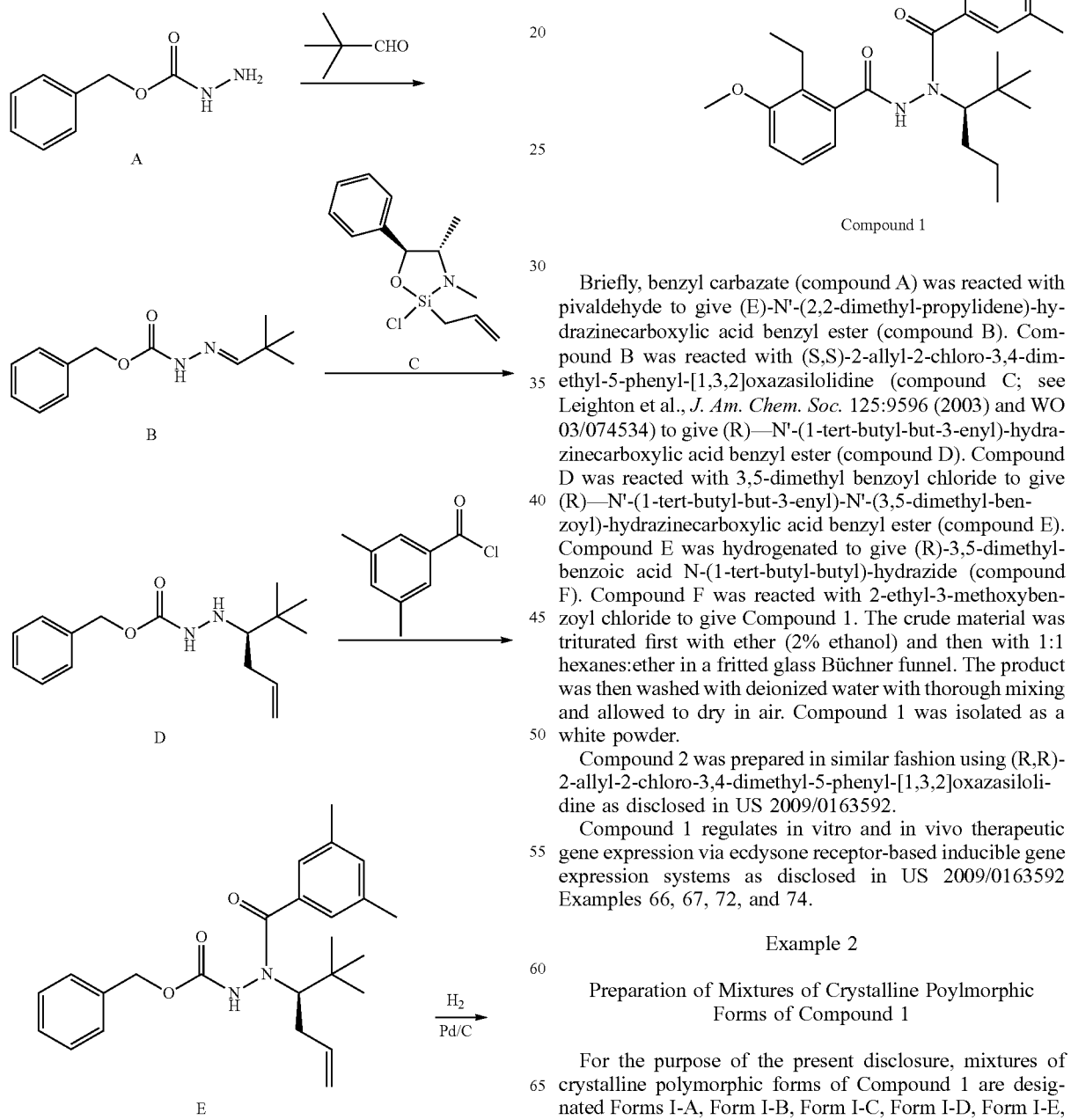

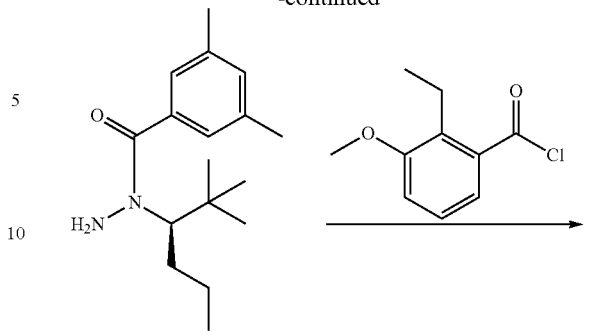

Briefly, benzyl carbazate (compound A) was reacted with pivaldehyde to give (E)-N'-(2,2-dimethyl-propylidene)-hydrazinecarboxylic acid benzyl ester (compound B). Compound B was reacted with (S,S)-2-allyl-2-chloro-3,4-dimethyl-5-phenyl-[1,3,2]oxazasilolidine (compound C; see Leighton et al., *J. Am. Chem. Soc.* 125:9596 (2003) and WO 03/074534) to give (R)—N'-(1-tert-butyl-but-3-enyl)-hydrazinecarboxylic acid benzyl ester (compound D). Compound D was reacted with 3,5-dimethyl benzoyl chloride to give (R)—N'-(1-tert-butyl-but-3-enyl)-N'-(3,5-dimethyl-benzoyl)-hydrazinecarboxylic acid benzyl ester (compound E). Compound E was hydrogenated to give (R)-3,5-dimethyl-benzoic acid N-(1-tert-butyl-butyl)-hydrazide (compound F). Compound F was reacted with 2-ethyl-3-methoxybenzoyl chloride to give Compound 1. The crude material was triturated first with ether (2% ethanol) and then with 1:1 hexanes:ether in a fritted glass Büchner funnel. The product was then washed with deionized water with thorough mixing and allowed to dry in air. Compound 1 was isolated as a white powder.

Compound 2 was prepared in similar fashion using (R,R)-2-allyl-2-chloro-3,4-dimethyl-5-phenyl-[1,3,2]oxazasilolidine as disclosed in US 2009/0163592.

Compound 1 regulates in vitro and in vivo therapeutic gene expression via ecdysone receptor-based inducible gene expression systems as disclosed in US 2009/0163592 Examples 66, 67, 72, and 74.

Example 2

Preparation of Mixtures of Crystalline Poylmorphic Forms of Compound 1

For the purpose of the present disclosure, mixtures of crystalline polymorphic forms of Compound 1 are designated Forms I-A, Form I-B, Form I-C, Form I-D, Form I-E, Form I-F, Form I-G, and Form I-H.

Method 1

Figure 2:
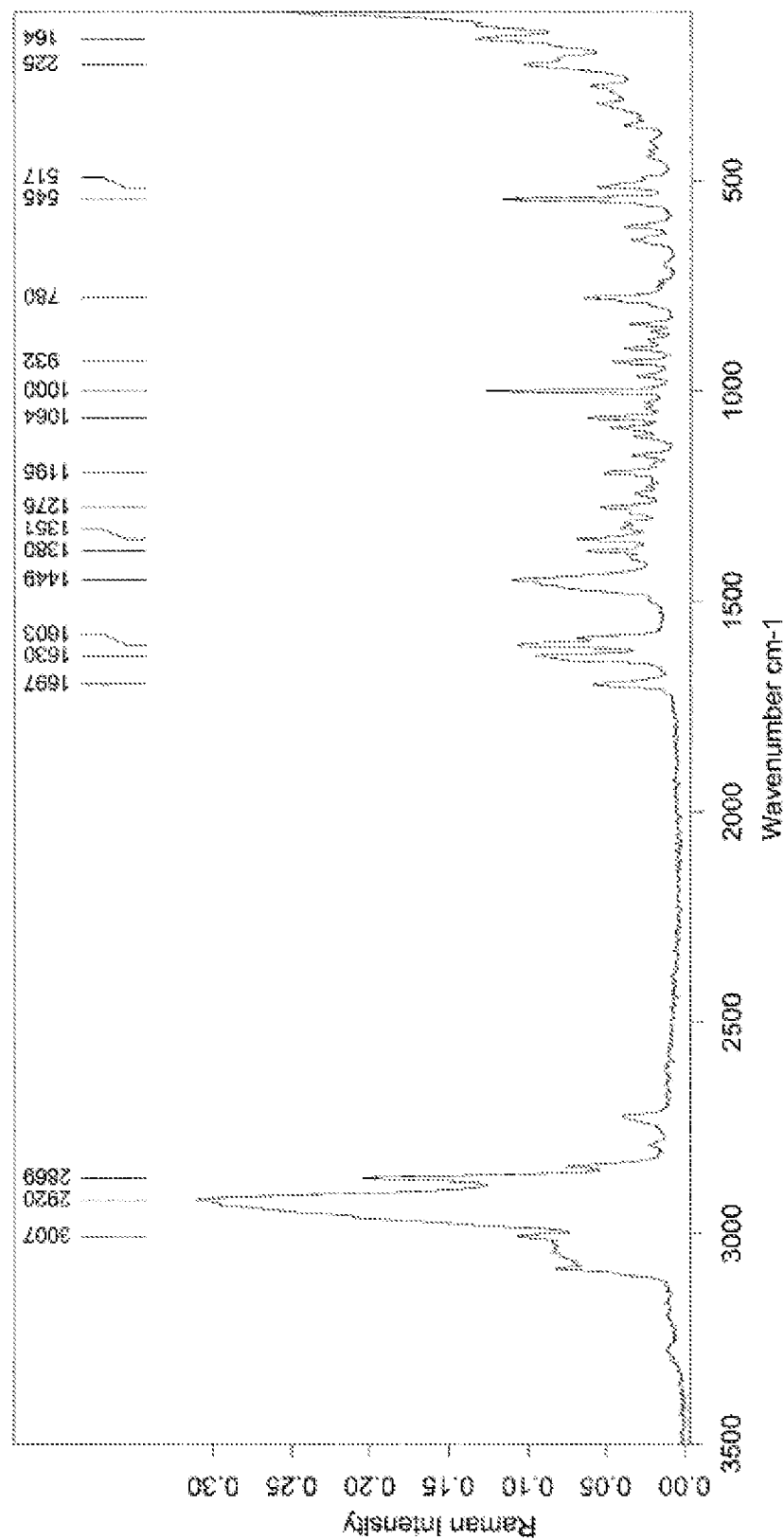
FIG. 2 is a FT-Raman spectrum of Form I-A of Compound 1.
Figure 3:
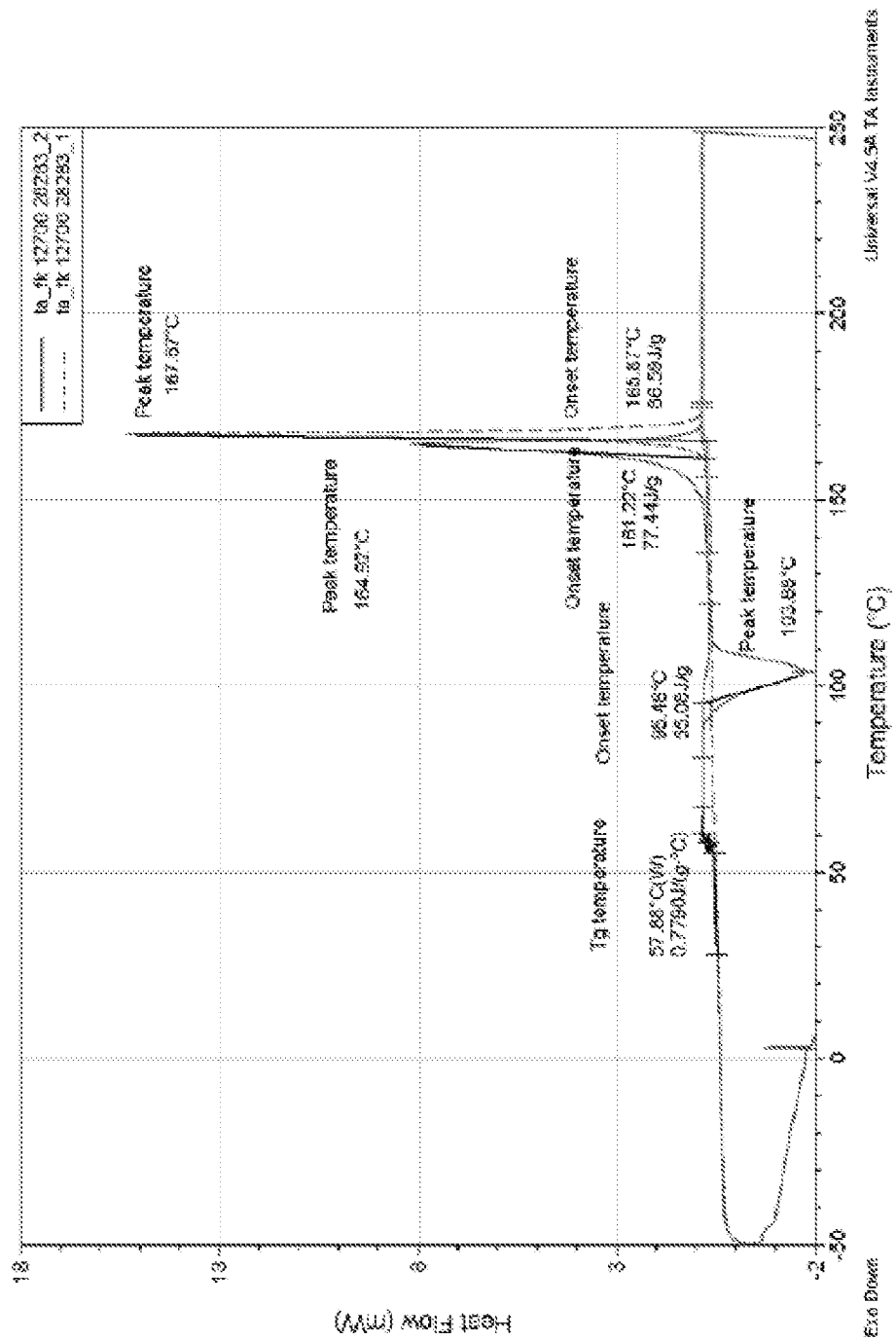
FIG. 3 DCS thermogram of Form I-A of Compound 1.

Compound 1 obtained using the methodology described in Example 1 was recrystallized from toluene/heptane, filtered, and dried under vacuum. This crystalline solid obtained was subjected to a second recrystallization from methanol/water, filtered, and dried under vacuum. The crystalline solid obtained was micronized to give crystalline Compound 1 Form I-A as a mixture of polymorphic forms (Form II with traces of Form IV), as characterized by PXRD, FT-Raman spectroscopy, and DSC (FIGS. 1-3, respectively). Micronized Compound 1 Form I-A was used as the starting material to prepare pure Forms II, III, IV, V, VI, VII, VIII, and IX, and mixtures thereof, in Methods 2-40 herein below.

Figure 4:
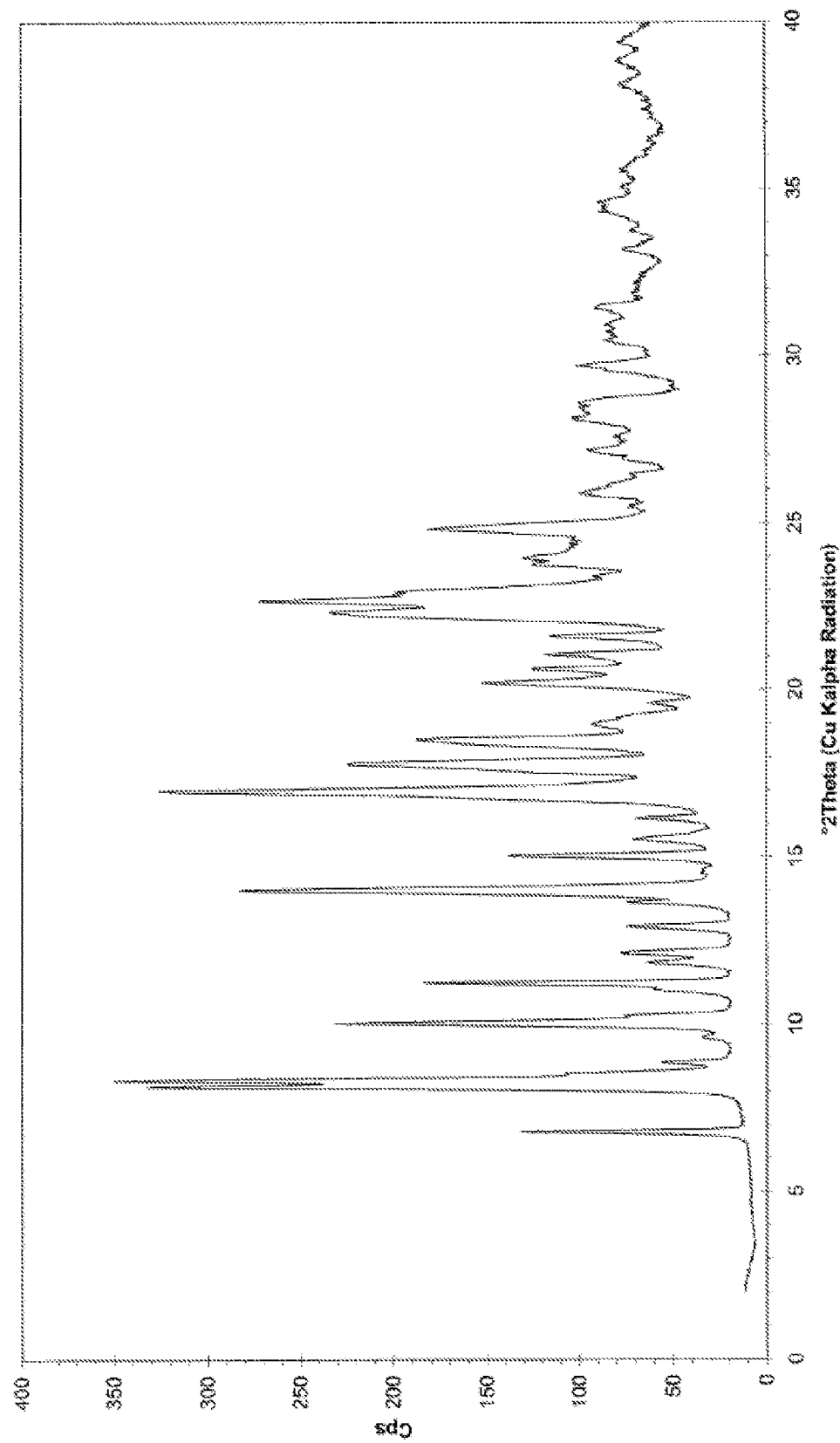
FIG. 4 is a PXRD diffractogram of Form I-B of Compound 1.
Figure 5:
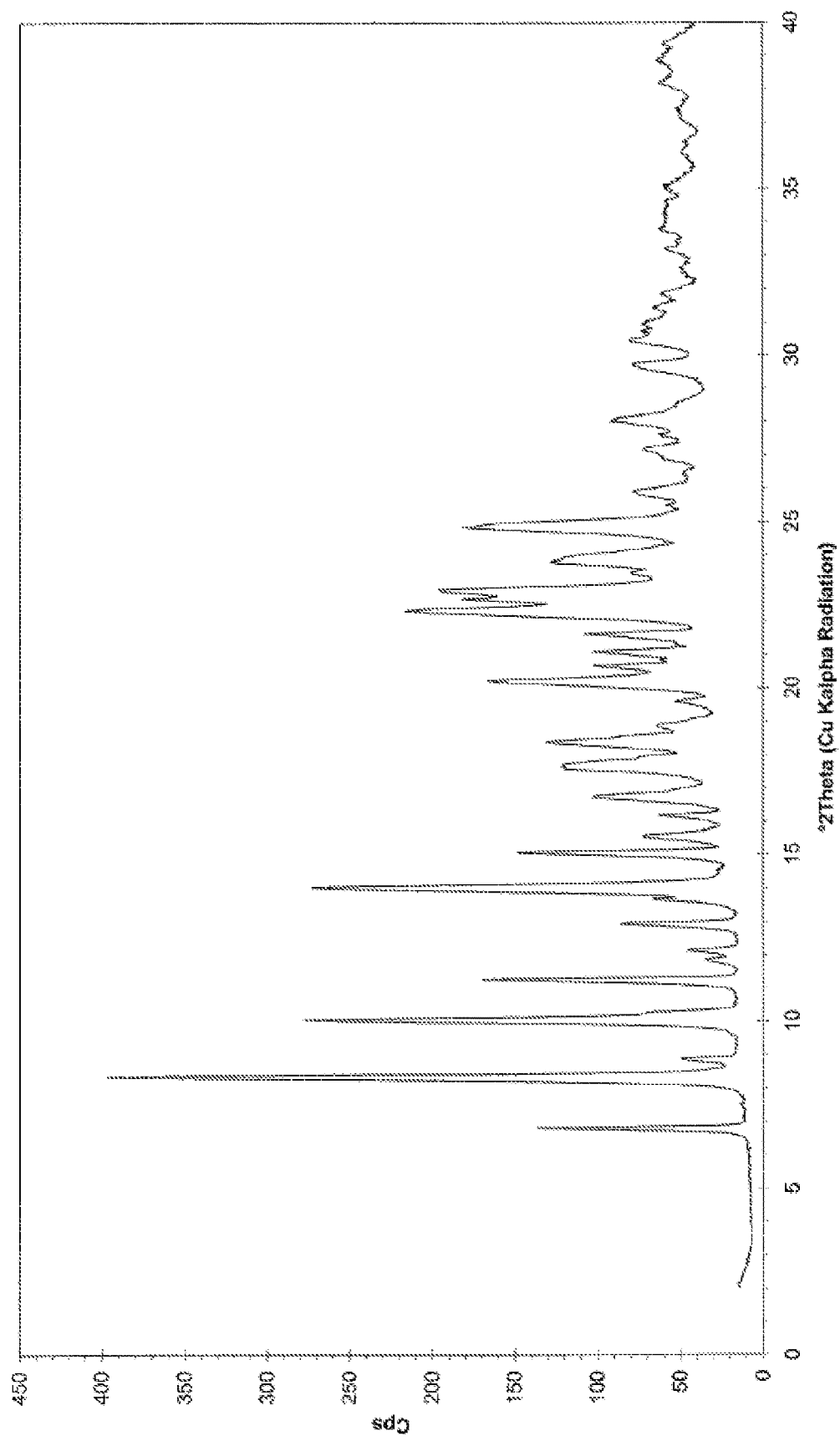
FIG. 5 is a PXRD diffractogram of Form I-C of Compound 1.
Figure 6:
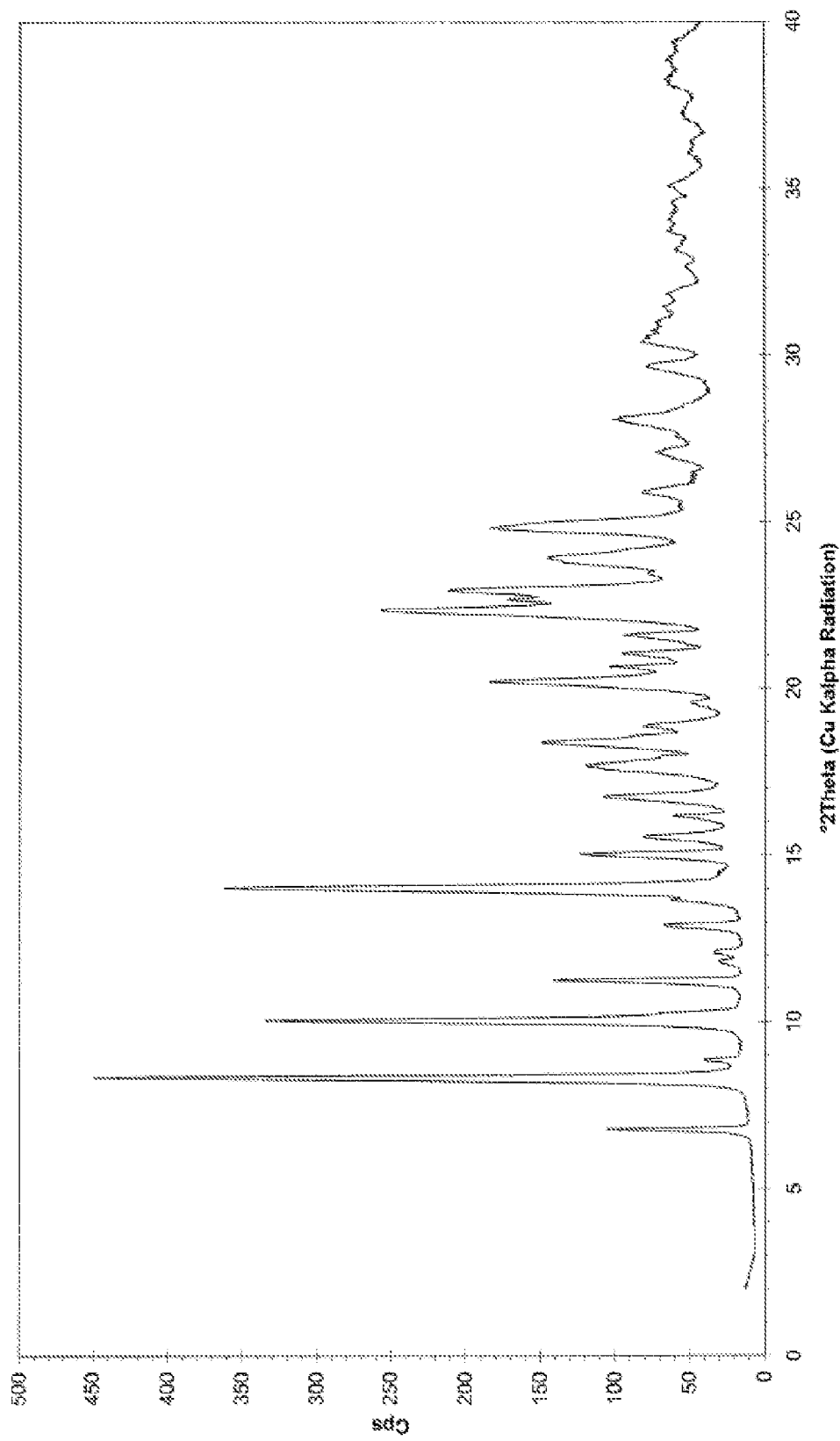
FIG. 6 is a PXRD diffractogram of Form I-D of Compound 1.

Using basically the same procedure as described in Method 1 without micronization, Compound 1 Form I-B (mixture of Form II, Form III, and Form IV), Form I-C (mixture of Form II and Form IV), and Form I-D (mixture of Form II and Form IV) were obtained (FIGS. 4-6, respectively).

Method 2

Figure 7:
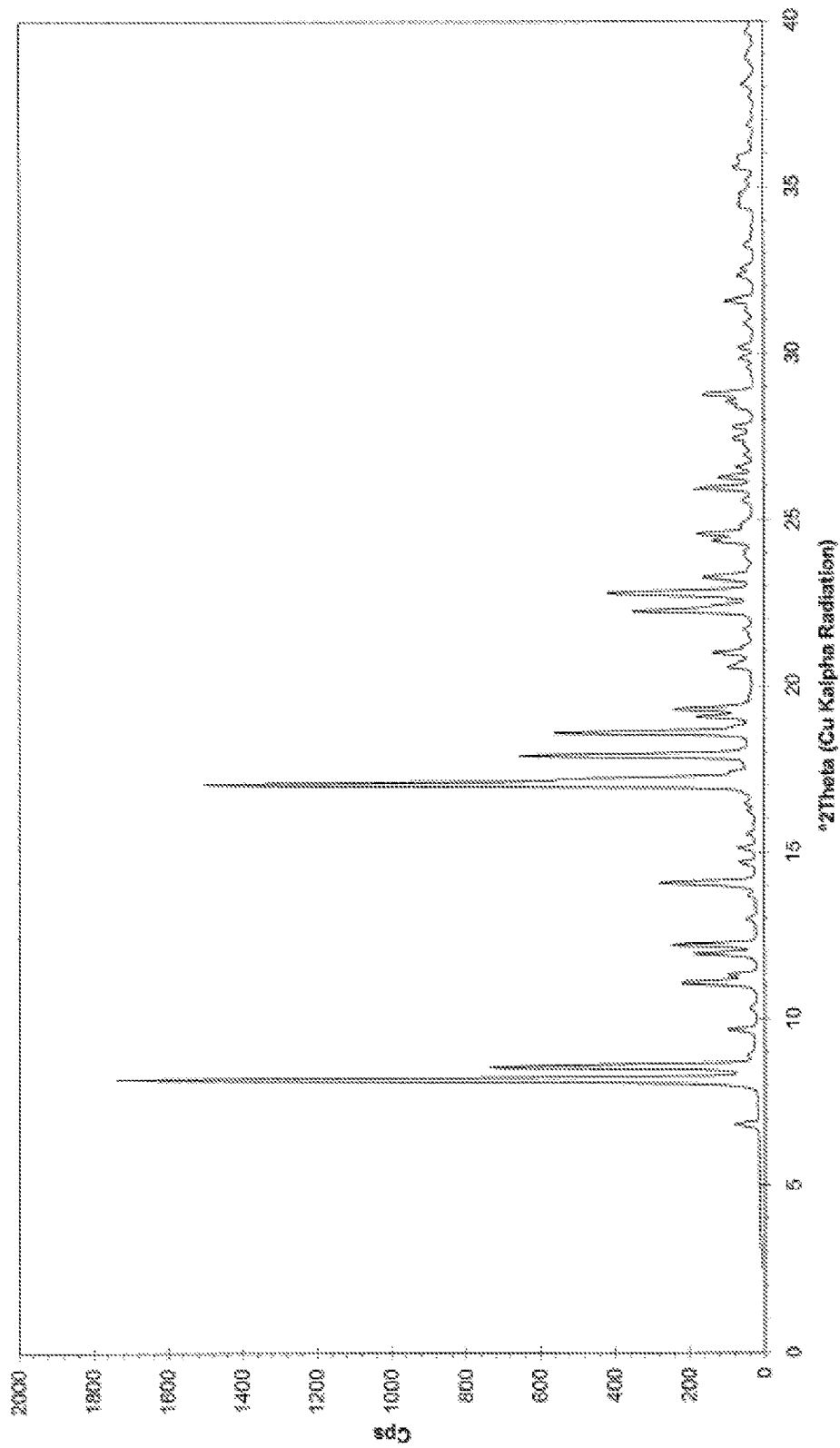
FIG. 7 is a PXRD diffractogram of Form I-E of Compound 1.

102 mg of Compound 1 Form I-A was suspended in 2.0 mL of n-hexane and sonicated. After stirring for 16 days at 5° C., the solid was collected by filtration and dried under vacuum for 30 minutes to give Form I-E (mixture of Form III with traces of Form IV, FIG. 7).

Method 3

Figure 8:
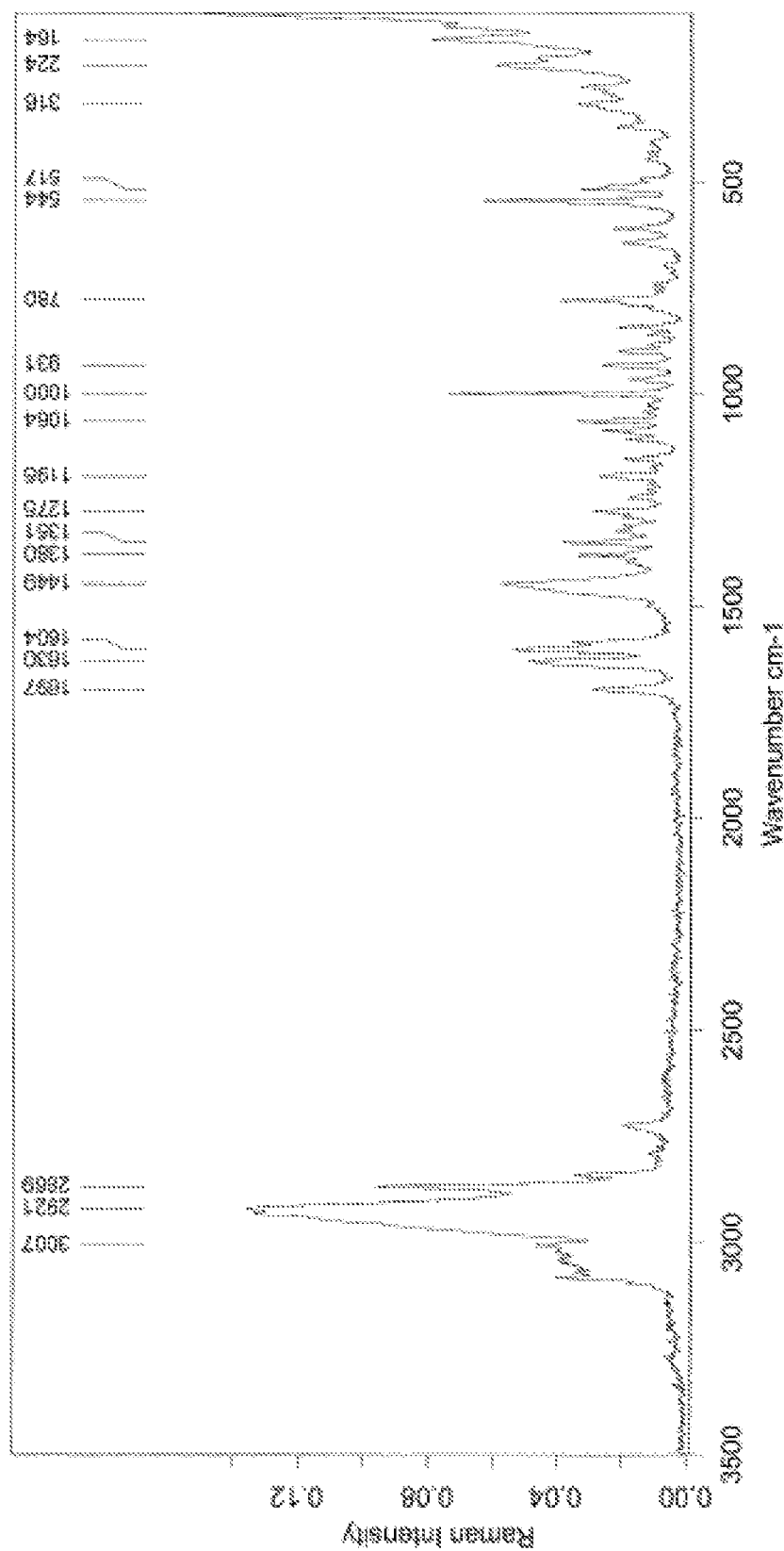
FIG. 8 is a FT-Raman spectrum of Form I-F of Compound 1.

103 mg of Compound 1 Form I-A was dissolved in 0.25 mL of isopropyl acetate. The solvent was evaporated under a stream of nitrogen of 1 day. The solid was dried under vacuum for 35 minutes to give Form I-F (mixture of Form II with traces of Form IV, FIG. 8).

Method 4

Figure 9:
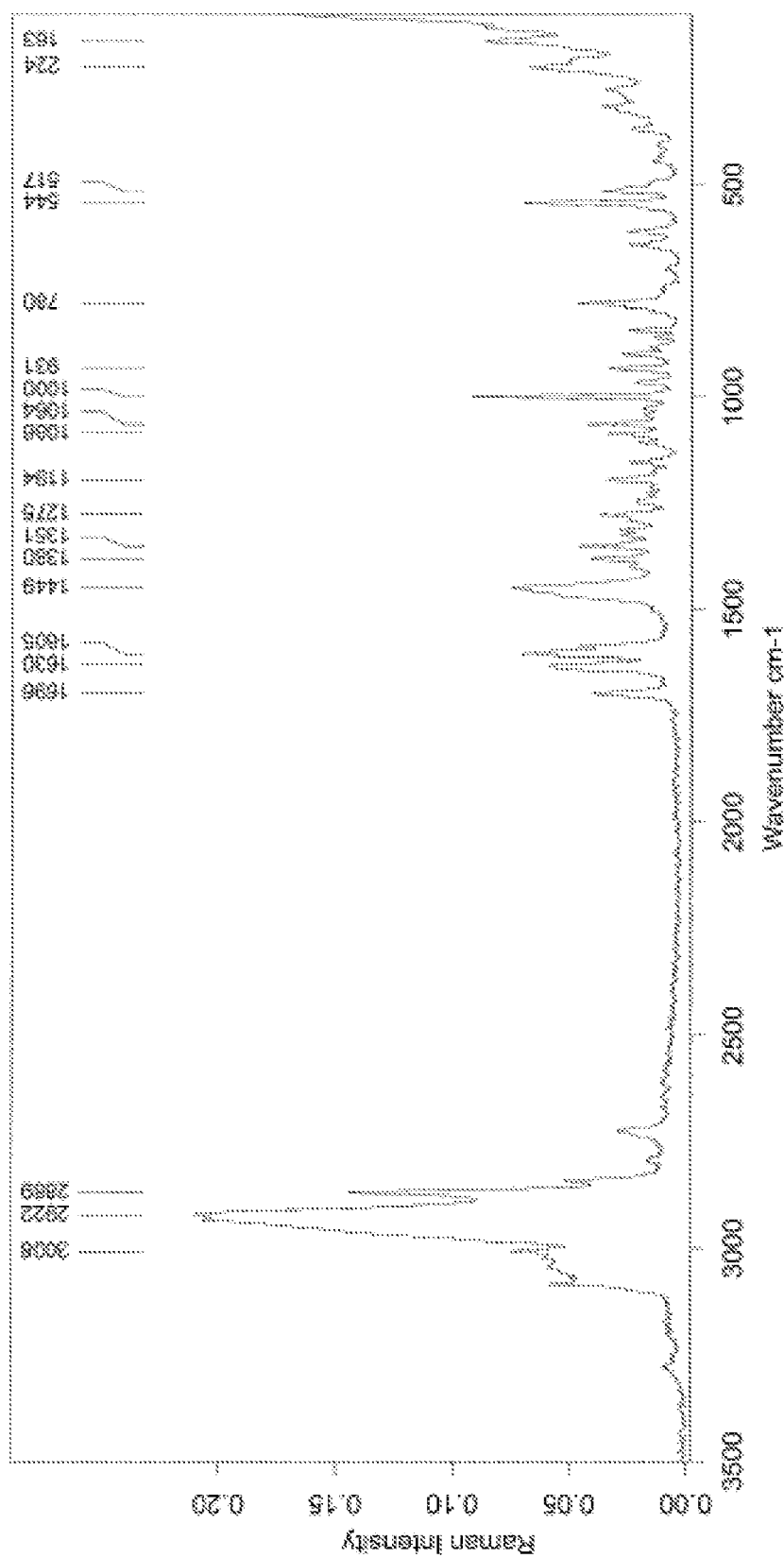
FIG. 9 is a FT-Raman spectrum of Form I-G of Compound 1.

100 mg of Compound 1 Form I-A was dissolved in 0.15 mL of tetrahydrofuran. The solvent was evaporated under a stream of nitrogen of 1 day. The solid was dried under vacuum for 35 minutes to give a mixture of Form I-G (mixture of Form II with traces of Form IV, FIG. 9).

Method 5

Figure 10:
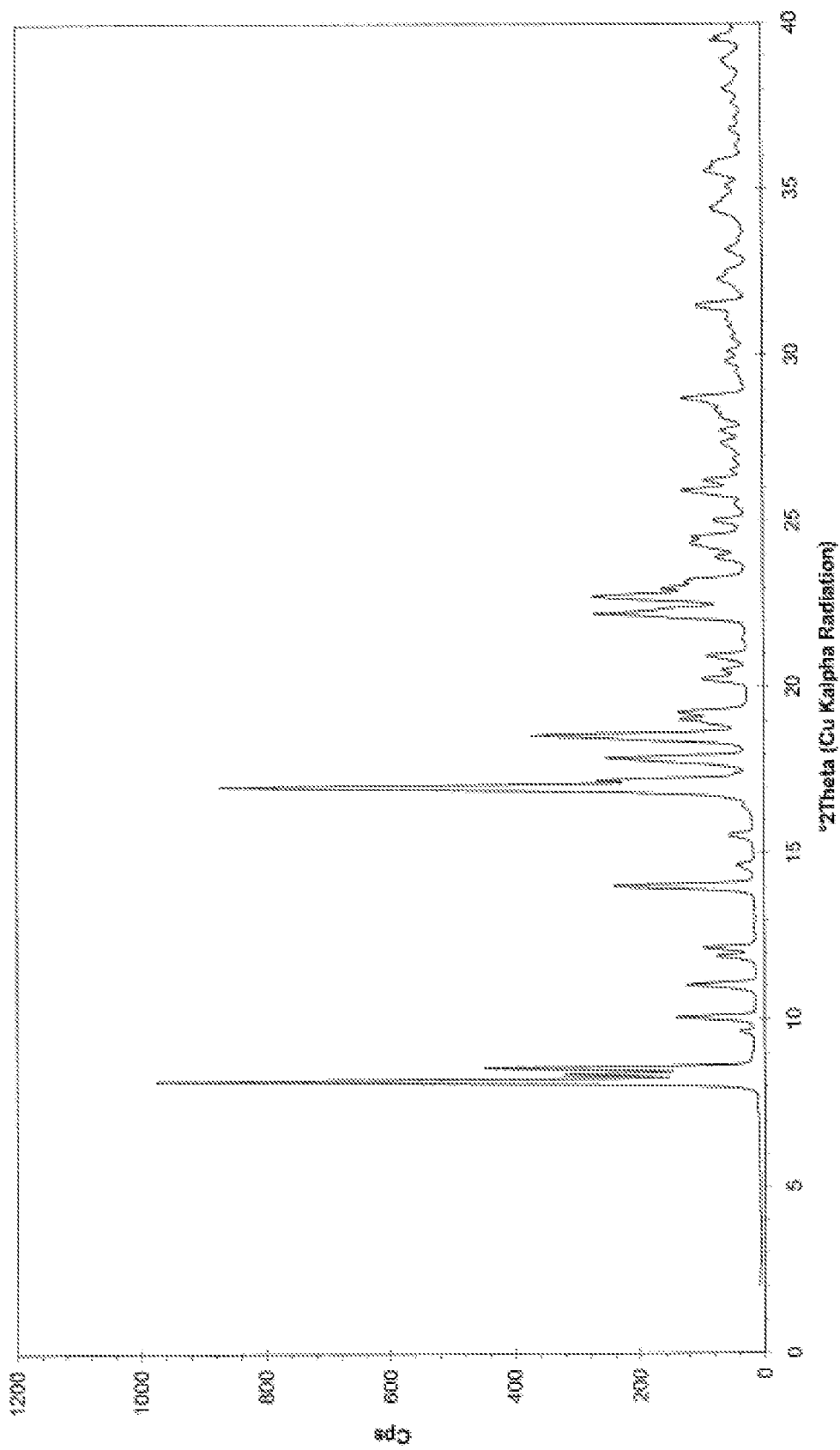
FIG. 10 is a PXRD diffractogram of Form I-H of Compound 1.

108 mg of Compound 1 Form I-A was dissolved in 3.7 mL of diisopropylether at 60° C. and the solution was heated to 65° C. The solution was cooled at 3° C./hour to 5° C. to give a suspension. The solid was collected by filtration and dried under vacuum for 1 hour to give Form I-H (mixture of Form II and Form III, FIG. 10).

Example 3

Preparation of Compound 1 Form II

Pure crystalline Compound 1 Form II was prepared according to the following methods:

Method 6

101 mg of Compound 1 Form I-A was suspended in 1.0 mL of cyclohexane and sonicated. After stirring for 17 days at 60° C., the solid was collected by filtration and dried under vacuum for 1 hour to give Form II.

Method 7

101 mg of Compound 1 Form I-A was suspended in 0.1 mL of 1:1 (v/v) benzyl alcohol/cyclohexane and sonicated. After stirring for 17 days at 60° C., the solid was collected by filtration and dried under vacuum for 1 hour to give Form II.

Method 8

99 mg of Compound 1 Form I-A was suspended in 0.1 mL of 3:2 (v/v) n-heptane/toluene and sonicated. After stirring for 17 days at 60° C., the solid was collected by filtration and dried under vacuum for 1 hour to give Form II.

Method 9

100 mg of Compound 1 Form I-A was suspended in 0.2 mL of 10:1 (v/v) n-heptane/toluene and sonicated. After stirring for 17 days at 60° C., the solid was collected by filtration and dried under vacuum for 1 hour to give Form II.

Method 10

105 mg of Compound 1 Form I-A was suspended in 0.1 mL of 1:10 (v/v) n-heptane/toluene and sonicated. After stirring for 17 days at 60° C., the solid was collected by filtration and dried under vacuum for 1 hour to give Form II.

Method 11

105 mg of Compound 1 Form I-A was suspended in 0.2 mL of 3:2 (v/v) n-heptane/toluene and sonicated. After stirring for 5 days at 90° C., an additional 0.1 mL of solvent was added. After stirring 2 more days at 90° C., the solid was collected by filtration and dried under vacuum for 20 minutes to give Form II.

Method 12

203 mg of Compound 1 Form I-A was dissolved in 0.2 mL of methyl ethyl ketone, and 2.0 mL of n-dodecane was added to give a precipitate. The precipitate was collected by filtration and dried under vacuum for 25 minutes to give Form II.

Method 13

105 mg of Compound 1 Form I-A was dissolved in 0.25 mL of acetonitrile. The solvent was evaporated under a stream of nitrogen for 1 day. The solid was dried under vacuum for 35 minutes to give Form II.

Method 14

105 mg of Compound 1 Form I-A was dissolved in 0.25 mL of isopropyl acetate. The solvent was evaporated under a stream of nitrogen for 1 day. The solid was dried under vacuum for 35 minutes to give Form II.

Method 15

112 mg of Compound 1 Form I-A was dissolved in 0.15 mL of dichloromethane. The solvent was evaporated under a stream of nitrogen for 1 day. The solid was dried under vacuum for 35 minutes to give Form II.

Figure 11:
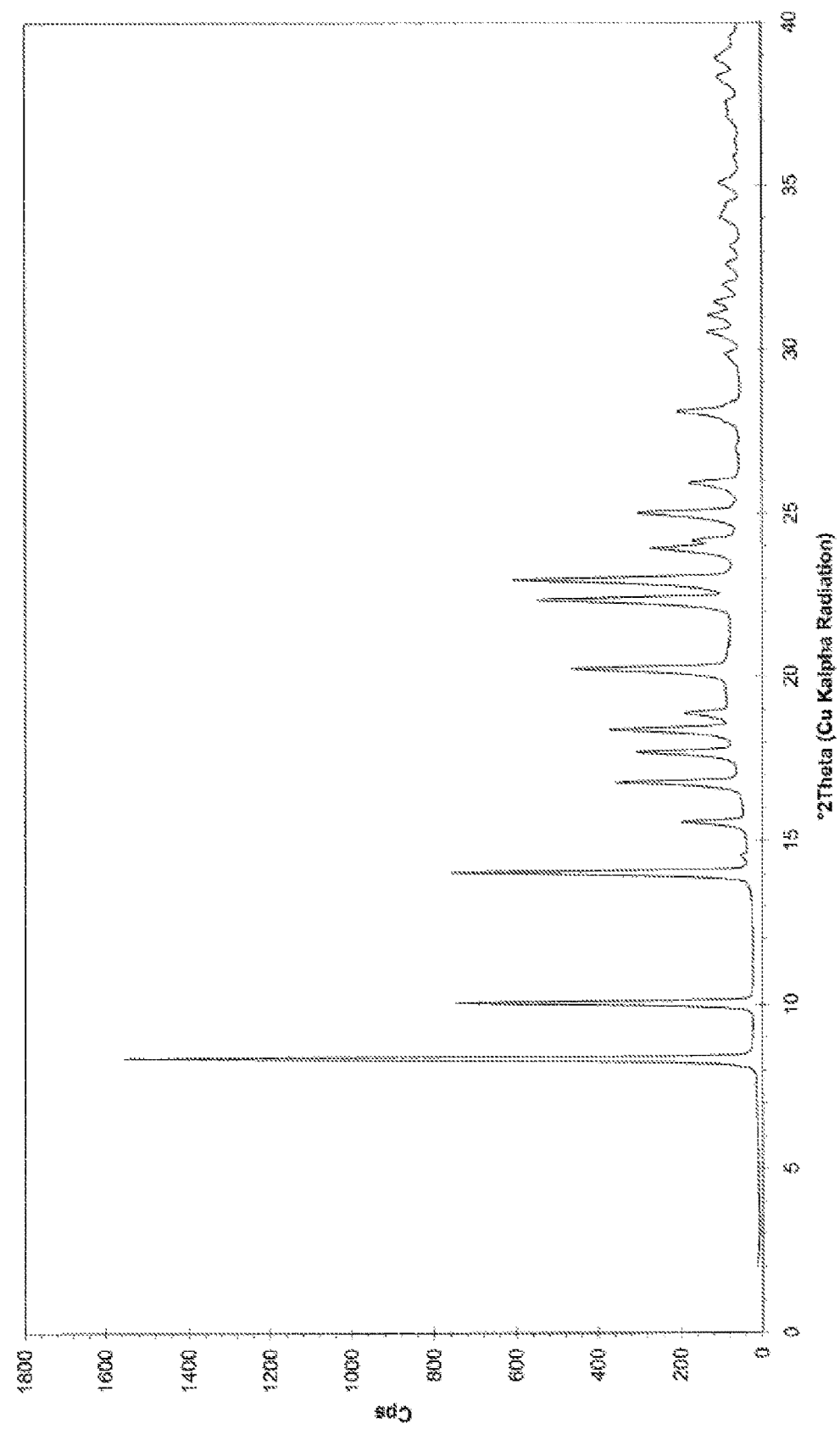
FIG. 11 is a PXRD diffractogram of pure Form II of Compound 1.
Figure 12:
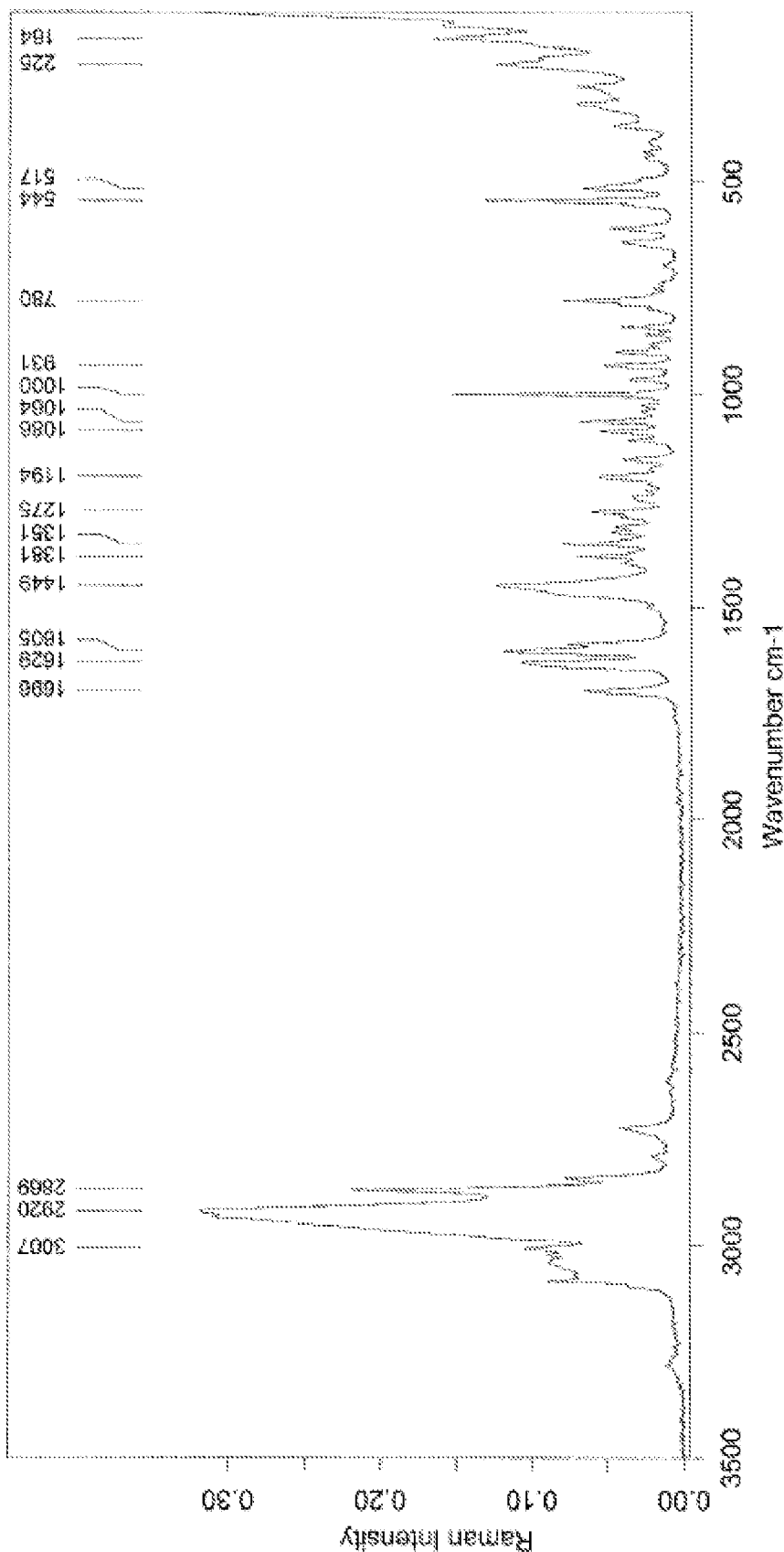
FIG. 12 is a FT-Raman spectrum of pure Form II of Compound 1.
Figure 13:
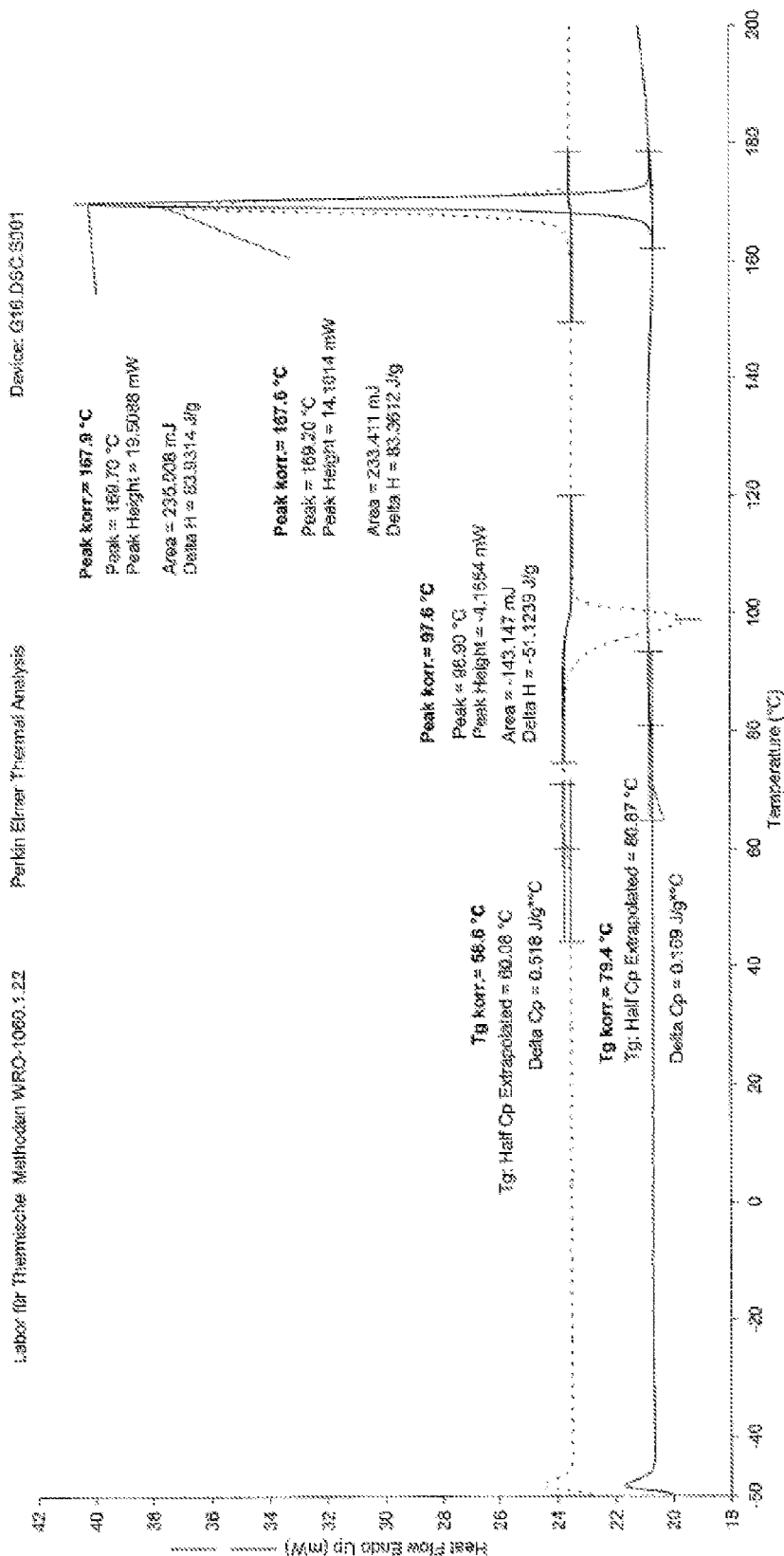
FIG. 13 is a DCS thermogram of pure Form II of Compound 1.

PXRD, FT-Raman, and DSC characterization of Compound 1 Form II is provided in FIGS. 11-13, respectively. Table 1 lists the PXRD peak positions, peak intensities, and d values of Compound I Form II. TG-FTIR showed that it is a non-solvated, i.e., anhydrous form. DVS showed that it is non- to slightly-hygroscopic as a water content of 0.1 wt.-% is gained from 0% relative humidity (r.h.) to 85% r.h.

TABLE 1

| Angle (2-Theta °) | d value (Angstrom) | Intensity (Cps) | Intensity (%) |
| --- | --- | --- | --- |
| 8.34 | 10.6 | 1033 | 100 |
| 10.06 | 8.8 | 506 | 49 |
| 14.01 | 6.3 | 522 | 51 |
| 14.51 | 6.1 | 37 | 4 |
| 15.55 | 5.69 | 139 | 14 |
| 16.77 | 5.28 | 246 | 24 |
| 17.70 | 5.01 | 217 | 21 |
| 18.40 | 4.82 | 260 | 25 |
| 18.88 | 4.70 | 130 | 13 |
| 20.23 | 4.39 | 317 | 31 |
| 22.36 | 3.97 | 384 | 37 |
| 22.97 | 3.87 | 428 | 42 |
| 23.91 | 3.72 | 192 | 19 |
| 24.15 | 3.68 | 122 | 12 |
| 25.00 | 3.56 | 215 | 21 |
| 25.92 | 3.43 | 126 | 12 |
| 26.96 | 3.30 | 44 | 4 |
| 28.09 | 3.17 | 148 | 14 |
| 28.33 | 3.15 | 59 | 6 |

TABLE 1-continued

| Angle (2-Theta °) | d value (Angstrom) | Intensity (Cps) | Intensity (%) |
|---|---|---|---|
| 29.84 | 2.99 | 60 | 6 |
| 30.52 | 2.93 | 95 | 9 |
| 31.05 | 2.88 | 93 | 9 |
| 31.45 | 2.84 | 84 | 8 |
| 31.97 | 2.80 | 67 | 7 |
| 32.61 | 2.74 | 60 | 6 |
| 33.17 | 2.70 | 55 | 5 |
| 34.02 | 2.63 | 74 | 7 |
| 34.45 | 2.60 | 61 | 6 |
| 35.07 | 2.56 | 72 | 7 |

In a separate experiment, 86.9 mg of Compound 1 Form II was stored in an open container in an autoclave under 1 bar of $CO_2$ atmosphere and over saturated NaCl solution (75-76% relative humidity) for 1 month to give unchanged Form II. There was no indication of hydrate (Form IV) or $CO_2$ adduct formation.

Two types of experiments elucidated the mechanical stability of Compound 1 Form II. First, about 200 mg of Form II was pressed in an IR press with a force of 10 metric tons (13 mm diameter of pellet) for 30 min. The resulting pellets were analyzed by PXRD. Second, about 150 mg of Form II was vigorously ground and analyzed by PXRD. The PXRD patterns of the samples after mechanical treatment show no change in crystalline form after grinding or pressurizing.

Example 4

Preparation of Compound 1 Form III

Pure crystalline Compound 1 Form III was prepared according to the following methods:

Method 16

109 mg of Compound 1 Form I-A was suspended in 2.0 mL of cyclohexane and sonicated. After stirring for 14 days at room temperature, the solid was collected by filtration and dried under vacuum for 30 minutes to give Form III.

Method 17

113 mg of Compound 1 Form I-A was suspended in 2.0 mL of n-heptane and sonicated. After stirring for 14 days at room temperature, the solid was collected by filtration and dried under vacuum for 30 minutes to give Form III.

Method 18

106 mg of Compound 1 Form I-A was suspended in 2.0 mL of cumeme and sonicated. After stirring for 1 day at room temperature, an additional 28 mg of Compound 1 Form I-A was added. After stirring for 13 days at room temperature, the solid was collected by filtration and dried under vacuum for 30 minutes to give Form III.

Method 19

109 mg of Compound 1 Form I-A was suspended in 1.0 mL of diethyl ether and sonicated. After stirring for 14 days at room temperature, the solid was collected by filtration and dried under vacuum for 30 minutes to give Form III.

Method 20

165 mg of Compound 1 Form I-A was suspended in 0.2 mL of ethyl acetate and sonicated. After stirring for 14 days at room temperature, the solid was collected by filtration and dried under vacuum for 30 minutes to give Form III.

Method 21

105 mg of Compound 1 Form I-A was suspended in 1.0 mL of tert-butyl methyl ether (TBME) and sonicated. After stirring for 14 days at room temperature, the solid was collected by filtration and dried under vacuum for 30 minutes to give Form III.

Method 22

103 mg of Compound 1 Form I-A was suspended in 0.2 mL of toluene and sonicated. After stirring for 14 days at room temperature, the solid was collected by filtration and dried under vacuum for 30 minutes to give Form III.

Method 23

101 mg of Compound 1 Form I-A was suspended in 2.0 mL of n-dodecane and sonicated. After stirring for 14 days at room temperature, the solid was collected by filtration and dried under vacuum for 30 minutes to give Form III.

Method 24

133 mg of Compound 1 Form I-A was suspended in 0.2 mL of 1:1 (v/v) n-hexane/ethanol and sonicated. After stirring for 14 days at room temperature, the solid was collected by filtration and dried under vacuum for 30 minutes to give Form III.

Method 25

178 mg of Compound 1 Form I-A was suspended in 0.2 mL of 1:1 (v/v) n-octane/acetone and sonicated. After stirring for 14 days at room temperature, the solid was collected by filtration and dried under vacuum for 30 minutes to give Form III.

Method 26

111 mg of Compound 1 Form I-A was suspended in 0.7 mL of 3:2 (v/v) n-heptane/toluene and sonicated. After stirring for 14 days at room temperature, the solid was collected by filtration and dried under vacuum for 2.5 hours to give Form III.

Method 27

97 mg of Compound 1 Form I-A was suspended in 0.8 mL of 10:1 (v/v) n-heptane/toluene and sonicated. After stirring for 14 days at room temperature, the solid was collected by filtration and dried under vacuum for 2.5 hours to give Form III.

Method 28

100 mg of Compound 1 Form I-A was suspended in 0.5 mL of 1:10 (v/v) n-heptane/toluene and sonicated. After stirring for 1 day at room temperature, 30 mg of Compound 1 Form I-A was added. After stirring for 13 days at room temperature, the solid was collected by filtration and dried under vacuum for 2.5 hours to give Form III.

Method 29

105 mg of Compound 1 Form I-A was suspended in 0.7 mL of 3:2 (v/v) n-heptane/toluene and sonicated. After stirring for 16 days at 5° C., the solid was collected by filtration and dried under vacuum for 30 minutes to give Form III.

Method 30

102 mg of Compound 1 Form I-A was suspended in 0.7 mL of 10:1 (v/v) n-heptane/toluene and sonicated. After stirring for 16 days at 5° C., the solid was collected by filtration and dried under vacuum for 30 minutes to give Form III.

Method 31

115 mg of Compound 1 Form I-A was suspended in 0.7 mL of 1:10 (v/v) n-heptane/toluene and sonicated. After stirring for 16 days at 5° C., the solid was collected by filtration and dried under vacuum for 30 minutes to give Form III.

These experiments show that at 5° C. and room temperature Form III is more stable than Form II.

Figure 14:
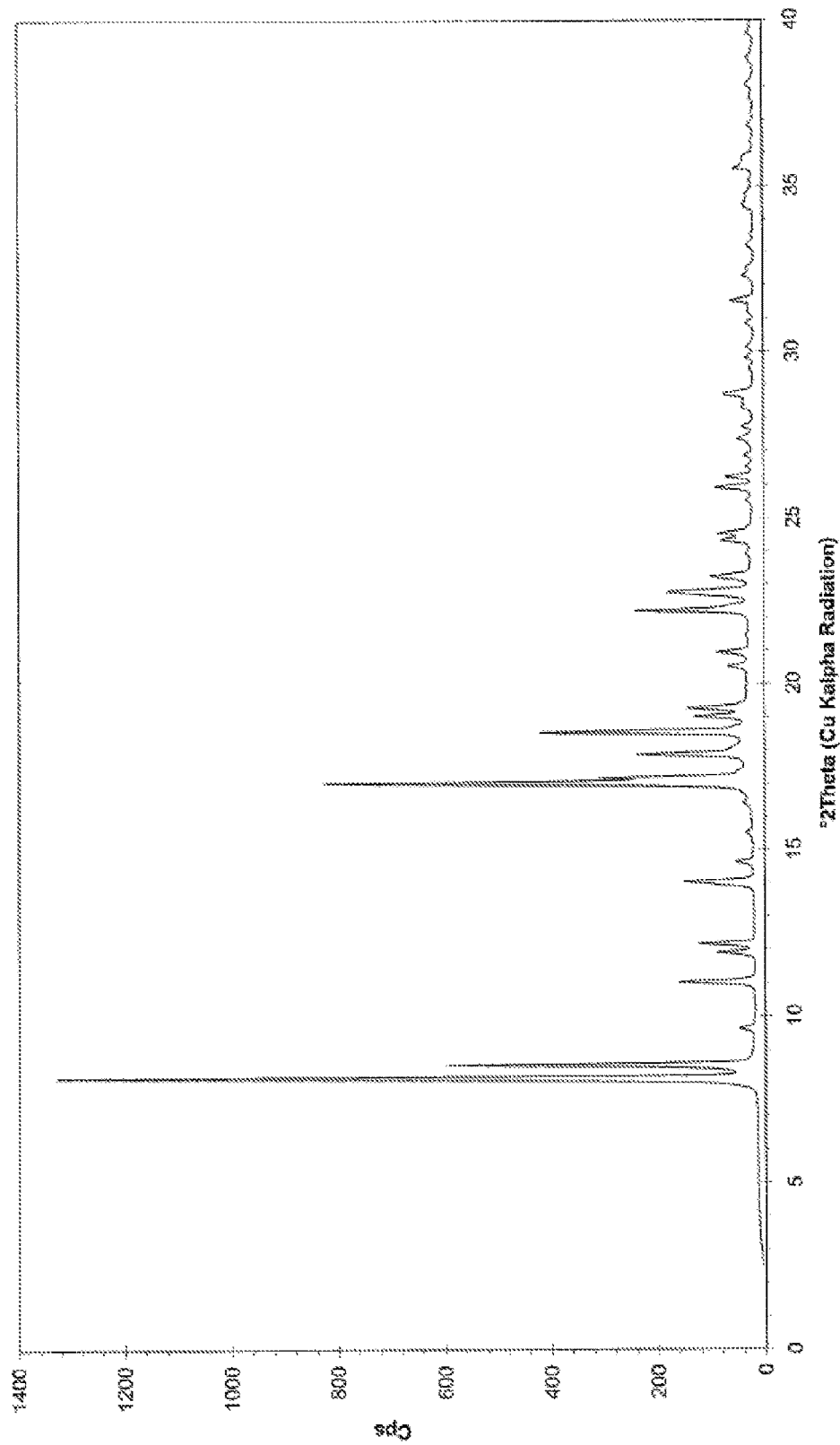
FIG. 14 is a PXRD diffractogram of pure Form III of Compound 1.
Figure 15:
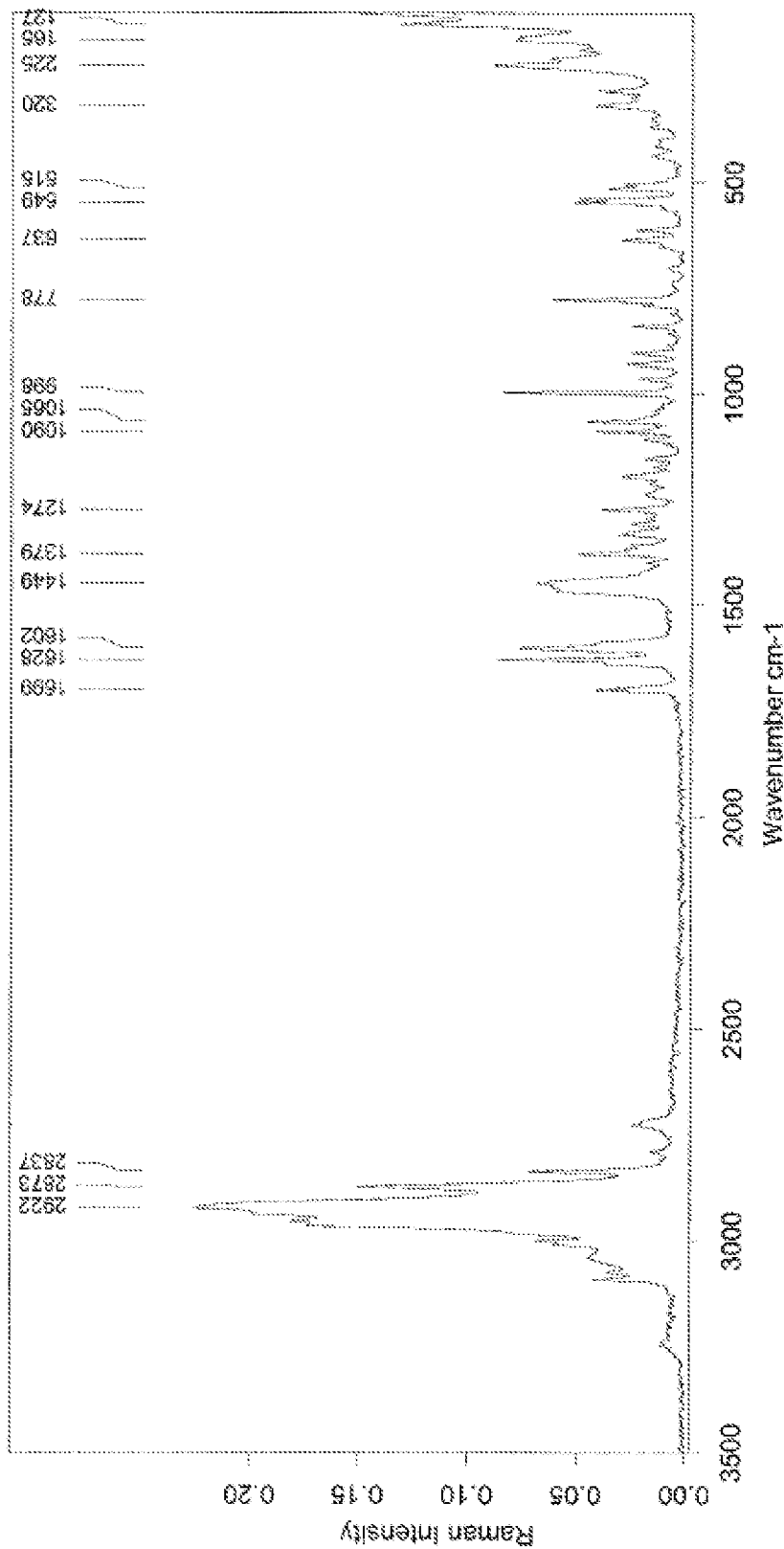
FIG. 15 is a FT-Raman spectrum of pure Form III of Compound 1.
Figure 16:
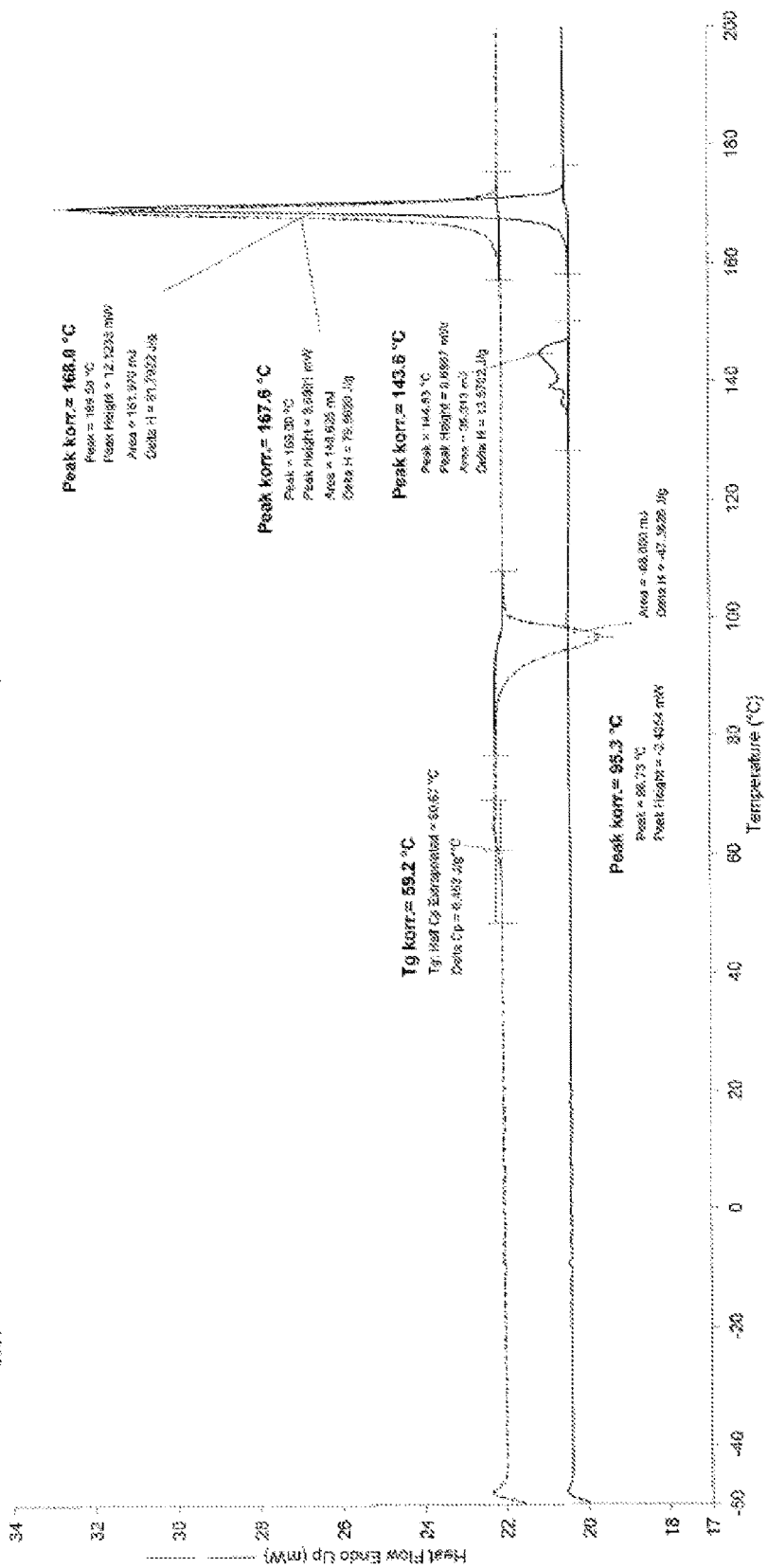
FIG. 16 is a DCS thermogram of pure Form III of Compound 1.

PXRD, FT-Raman, and DSC characterization of Compound 1 Form III is provided in FIGS. 14-16, respectively. Table 2 lists the PXRD peak positions, peak intensities, and d values of Compound I Form III. TG-FTIR investigation shows that it is a non-solvated, i.e., anhydrous form. DVS showed that it is non- to slightly-hygroscopic as a water content of 0.1 wt.-% is gained from 0% relative humidity (r.h.) to 85% r.h.

TABLE 2

| Angle (2-Theta °) | d value (Angstrom) | Intensity (Cps) | Intensity (%) |
|---|---|---|---|
| 8.14 | 10.9 | 899 | 100 |
| 8.52 | 10.4 | 402 | 45 |
| 9.62 | 9.2 | 34 | 4 |
| 11.02 | 8.0 | 116 | 13 |
| 11.90 | 7.4 | 63 | 7 |
| 12.16 | 7.3 | 86 | 10 |
| 14.02 | 6.3 | 105 | 12 |
| 14.62 | 6.1 | 38 | 4 |
| 17.00 | 5.21 | 611 | 68 |
| 17.88 | 4.96 | 172 | 19 |
| 18.56 | 4.78 | 321 | 36 |
| 19.02 | 4.66 | 100 | 11 |
| 19.24 | 4.61 | 106 | 12 |
| 20.51 | 4.33 | 50 | 6 |
| 20.93 | 4.24 | 68 | 8 |
| 22.19 | 4.00 | 194 | 22 |
| 22.73 | 3.91 | 129 | 14 |
| 23.22 | 3.83 | 69 | 8 |
| 24.31 | 3.66 | 61 | 7 |
| 24.53 | 3.63 | 67 | 8 |
| 25.91 | 3.44 | 71 | 8 |
| 26.22 | 3.40 | 58 | 6 |
| 27.36 | 3.26 | 39 | 4 |
| 27.73 | 3.21 | 30 | 3 |
| 28.70 | 3.11 | 57 | 6 |
| 30.84 | 2.90 | 24 | 3 |
| 31.52 | 2.84 | 52 | 6 |
| 32.30 | 2.77 | 28 | 3 |
| 33.19 | 2.70 | 22 | 3 |
| 34.39 | 2.61 | 24 | 3 |

In a separate experiment, 52.4 mg of Compound 1 Form III was stored in an open container in an autoclave under 1 bar of $CO_2$ atmosphere and over saturated NaCl solution (75-76% relative humidity) for 1 month to give unchanged Form III. There was no indication of hydrate (Form IV) or $CO_2$ adduct formation.

Two types of experiments elucidated the mechanical stability of Compound 1 Form III. First, about 200 mg of Form III was pressed in an IR press with a force of 10 metric tons (13 mm diameter of pellet) for 30 min. The resulting pellets were analyzed by PXRD. Second, about 150 mg of Form III was vigorously ground and analyzed by PXRD. The PXRD patterns of the samples after mechanical treatment show no change in crystalline form after grinding or pressurizing.

Example 5

Preparation of Compound 1 Form IV

Pure crystalline Compound 1 Form IV was prepared according to the following methods:
Method 32
106 mg of Compound 1 Form I-A was suspended in 2.0 mL of water and sonicated. After stirring for 14 days at room temperature, the solid was collected by filtration and dried under vacuum for 30 minutes to give Form IV. TG-FTIR investigation shows Form IV is a hydrate with a loss of 3.5 wt.-% water from 25° C.-150° C. (3.9 wt.-% would correspond to a monohydrate). According to TG-FTIR, the hydrate releases water near 100° C.

Method 33
100 mg of Compound 1 Form I-A was suspended in 5.0 mL of 1:1 (v/v) water:ethanol and sonicated. After stirring for 16 days at 5° C., the solid was collected by filtration and dried under vacuum for 30 minutes to give Form IV.
Method 34
109 mg of Compound 1 Form I-A was suspended in 5.0 mL of 1:1 (v/v) water:2-propanol and sonicated. After stirring for 16 days at 5° C., the solid was collected by filtration and dried under vacuum for 30 minutes to give Form IV.

PXRD, FT-Raman, and DSC (2 thermograms) characterization of Compound I Form IV is provided in FIGS. 17-20, respectively. Table 3 lists the PXRD peak positions, peak intensities, and d values of Compound I Form IV.

TABLE 3

| Angle (2-Theta °) | d value (Angstrom) | Intensity (Cps) | Intensity (%) |
|---|---|---|---|
| 6.83 | 12.9 | 364 | 83 |
| 8.38 | 10.5 | 83 | 19 |
| 8.91 | 9.9 | 82 | 19 |
| 10.11 | 8.7 | 63 | 14 |
| 10.31 | 8.6 | 129 | 30 |
| 11.30 | 7.8 | 437 | 100 |
| 11.89 | 7.4 | 74 | 17 |
| 12.18 | 7.3 | 97 | 22 |
| 12.98 | 6.8 | 214 | 49 |
| 13.69 | 6.5 | 119 | 27 |
| 14.14 | 6.3 | 77 | 18 |
| 15.11 | 5.86 | 306 | 70 |
| 15.81 | 5.60 | 39 | 9 |
| 16.23 | 5.46 | 118 | 27 |
| 17.60 | 5.03 | 98 | 22 |
| 17.99 | 4.93 | 116 | 27 |
| 18.60 | 4.77 | 83 | 19 |
| 19.15 | 4.63 | 38 | 9 |
| 19.66 | 4.51 | 75 | 17 |
| 20.28 | 4.38 | 60 | 14 |
| 20.70 | 4.29 | 156 | 36 |
| 21.15 | 4.20 | 178 | 41 |
| 21.68 | 4.10 | 148 | 34 |
| 22.44 | 3.96 | 47 | 11 |
| 22.71 | 3.91 | 196 | 45 |
| 23.50 | 3.78 | 68 | 16 |
| 23.79 | 3.74 | 91 | 21 |
| 24.06 | 3.70 | 62 | 14 |
| 24.86 | 3.58 | 187 | 43 |
| 25.55 | 3.48 | 41 | 9 |
| 26.53 | 3.36 | 46 | 10 |
| 26.94 | 3.31 | 45 | 10 |
| 27.21 | 3.28 | 72 | 17 |
| 27.60 | 3.23 | 50 | 12 |
| 28.67 | 3.11 | 35 | 8 |
| 29.79 | 3.00 | 75 | 17 |
| 30.50 | 2.93 | 43 | 10 |
| 30.75 | 2.91 | 51 | 12 |
| 31.55 | 2.83 | 32 | 7 |
| 31.89 | 2.80 | 35 | 8 |
| 32.78 | 2.73 | 27 | 6 |
| 33.25 | 2.69 | 33 | 8 |
| 33.48 | 2.68 | 38 | 9 |
| 33.81 | 2.65 | 44 | 10 |
| 34.68 | 2.59 | 46 | 11 |

Example 6

Preparation of Compound 1 Form V

Method 35
126 mg of Compound 1 Form I-A was dissolved in 0.55 mL of methanol. The solvent was evaporated under a stream of nitrogen for 1 day. The solid was dried under vacuum for 35 minutes to give Form V. TG-FTIR investigation showed that Form V was a methanol monosolvate with a loss of 6.7 wt.-% of methanol from 50-150° C. (6.8 wt.-% would correspond to a monosolvate).

Figure 21:
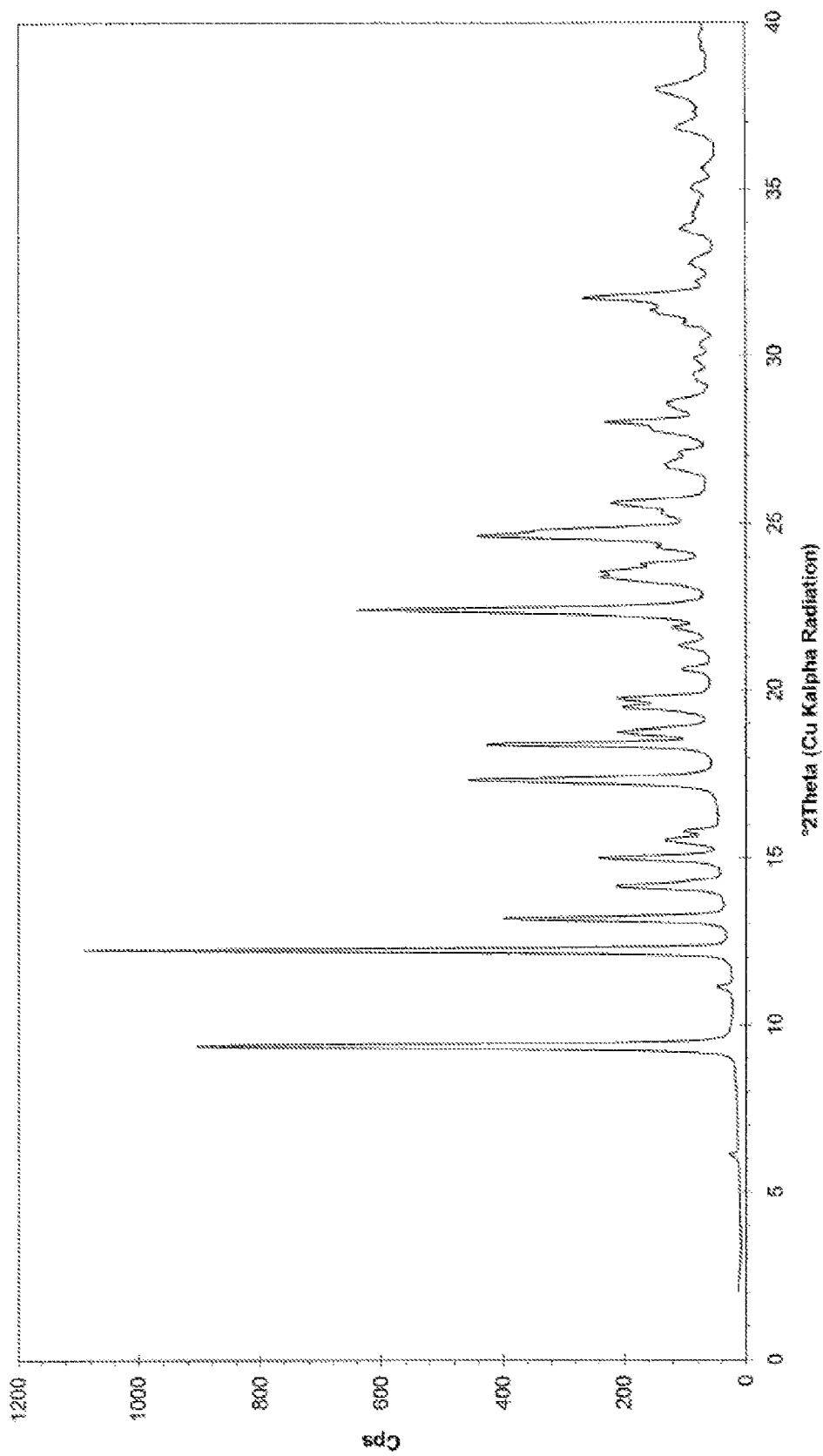
FIG. 21 is a PXRD diffractogram of pure Form V of Compound 1.
Figure 22:
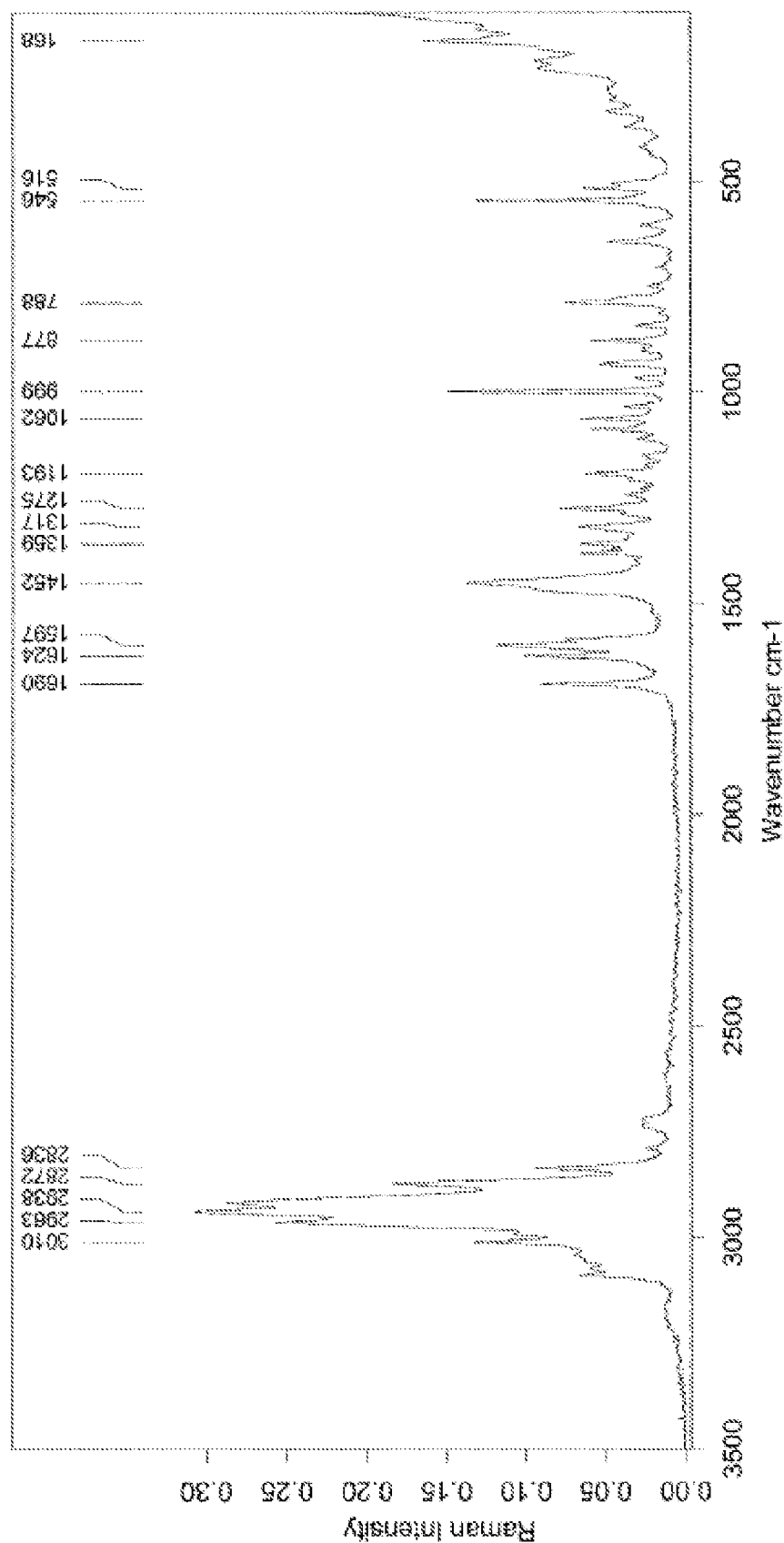
FIG. 22 is a FT-Raman spectrum of pure Form V of Compound 1.

PXRD and FT-Raman characterization of Compound I Form V is provided in FIGS. 21 and 22, respectively. Table 4 lists the PXRD peak positions, peak intensities, and d values of Compound I Form V.

TABLE 4

| Angle (2-Theta °) | d value (Angstrom) | Intensity (Cps) | Intensity (%) |
|---|---|---|---|
| 6.11 | 14.5 | 18 | 2 |
| 9.38 | 9.4 | 607 | 81 |
| 11.13 | 7.9 | 33 | 4 |
| 12.22 | 7.2 | 746 | 100 |
| 13.18 | 6.7 | 271 | 36 |
| 14.14 | 6.3 | 143 | 19 |
| 14.98 | 5.91 | 160 | 22 |
| 15.52 | 5.71 | 90 | 12 |
| 15.78 | 5.61 | 70 | 9 |
| 17.32 | 5.12 | 310 | 42 |
| 18.40 | 4.82 | 309 | 42 |
| 18.75 | 4.73 | 145 | 19 |
| 19.48 | 4.55 | 139 | 19 |
| 19.74 | 4.49 | 142 | 19 |
| 20.63 | 4.30 | 74 | 10 |
| 21.33 | 4.16 | 75 | 10 |
| 21.88 | 4.06 | 85 | 11 |
| 22.41 | 3.97 | 444 | 60 |
| 23.40 | 3.80 | 163 | 22 |
| 23.55 | 3.78 | 164 | 22 |
| 23.76 | 3.74 | 118 | 16 |
| 24.27 | 3.67 | 103 | 14 |
| 24.63 | 3.61 | 314 | 42 |
| 24.79 | 3.59 | 232 | 31 |
| 25.61 | 3.48 | 150 | 20 |
| 26.66 | 3.34 | 91 | 12 |
| 27.10 | 3.29 | 77 | 10 |
| 27.81 | 3.21 | 104 | 14 |
| 28.02 | 3.18 | 170 | 23 |
| 28.58 | 3.12 | 87 | 12 |
| 29.91 | 2.99 | 58.5 | 8 |
| 30.35 | 2.94 | 51.2 | 7 |
| 30.95 | 2.89 | 74.9 | 10 |
| 31.32 | 2.85 | 100 | 14 |
| 31.77 | 2.82 | 198 | 27 |
| 32.77 | 2.73 | 64.4 | 9 |
| 33.81 | 2.65 | 74.2 | 10 |
| 34.98 | 2.56 | 61.4 | 8 |

Example 7

Preparation of Compound 1 Form VI

Method 36

101 mg of Compound 1 Form I-A was suspended in 5.0 mL of 1:1 (v:v) water:methanol and sonicated. After stirring for 14 days at room temperature, the solid was collected by filtration and dried under vacuum for 30 minutes to give Form VI. The PXRD pattern of the dried sample is different from a superposition of Form IV (hydrate) and Form V (methanol monosolvate). Form VI is probably a mixed methanol solvate/hydrate. In this form, the methanol/water ratio can affect the solid structure, and this would likely result in PXRD peak position shifts. TG-FTIR investigation shows a loss of 3.8 wt.-% methanol (and some water) from 25° C.-90° C. and 2.1 wt.-% water (and some methanol) from 90-130° C. (3.5 wt.-% methanol would correspond to a hemi-solvate; 2.0 wt.-% water would correspond to a hemi-hydrate).

Figure 23:
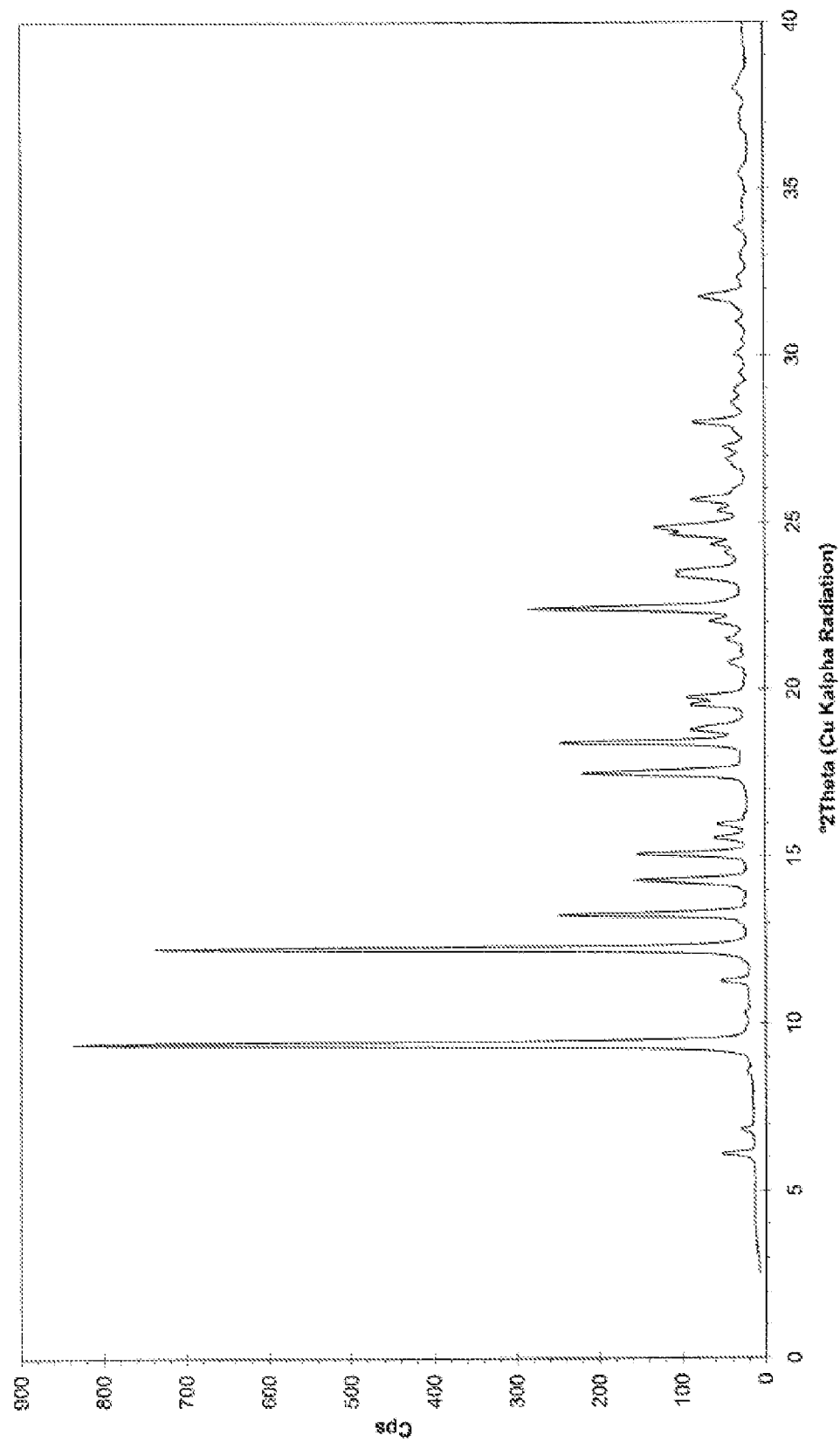
FIG. 23 is a PXRD diffractogram of pure Form VI of Compound 1.
Figure 24:
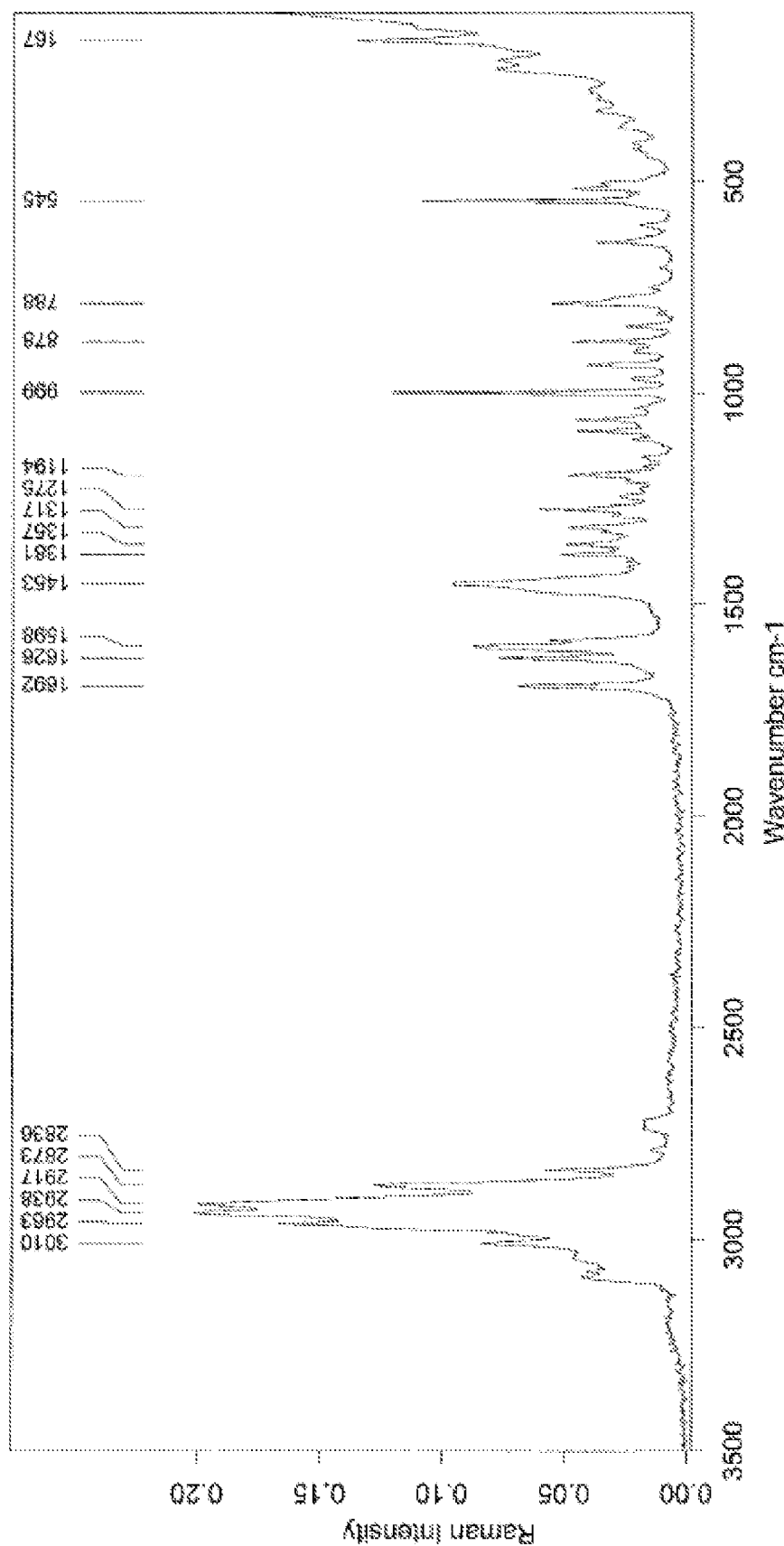
FIG. 24 is a FT-Raman spectrum of pure Form VI of Compound 1.

PXRD and FT-Raman characterization of Compound I Form VI is provided in FIGS. 23 and 24, respectively. Table 5 lists the PXRD peak positions, peak intensities, and d values of Compound I Form VI.

TABLE 5

| Angle (2-Theta °) | d value (Angstrom) | Intensity (Cps) | Intensity (%) |
|---|---|---|---|
| 6.09 | 14.5 | 34 | 6 |
| 6.82 | 12.9 | 21 | 4 |
| 8.57 | 10.3 | 16 | 3 |
| 9.38 | 9.4 | 566 | 100 |
| 11.26 | 7.9 | 36 | 6 |
| 12.23 | 7.2 | 513 | 91 |
| 13.25 | 6.7 | 174 | 31 |
| 14.27 | 6.2 | 108 | 19 |
| 15.05 | 5.88 | 107 | 19 |
| 15.54 | 5.70 | 45 | 8 |
| 15.95 | 5.55 | 39 | 7 |
| 17.48 | 5.07 | 156 | 28 |
| 18.41 | 4.82 | 177 | 31 |
| 18.79 | 4.72 | 63 | 11 |
| 19.54 | 4.54 | 62 | 11 |
| 19.76 | 4.49 | 68 | 12 |
| 20.79 | 4.27 | 29 | 5 |
| 21.48 | 4.13 | 33 | 6 |
| 22.02 | 4.03 | 47 | 8 |
| 22.41 | 3.96 | 213 | 38 |
| 23.42 | 3.80 | 73 | 13 |
| 24.07 | 3.69 | 33 | 6 |
| 24.34 | 3.65 | 47 | 8 |
| 24.64 | 3.61 | 78 | 14 |
| 24.83 | 3.58 | 90 | 16 |
| 25.34 | 3.51 | 40 | 7 |
| 25.67 | 3.47 | 63 | 11 |
| 26.74 | 3.33 | 25 | 4 |
| 26.87 | 3.32 | 31 | 5 |
| 27.24 | 3.27 | 35 | 6 |
| 27.99 | 3.19 | 64 | 11 |
| 28.56 | 3.12 | 27 | 5 |
| 28.93 | 3.08 | 25 | 4 |
| 29.47 | 3.03 | 21 | 4 |
| 30.04 | 2.97 | 26 | 5 |
| 30.98 | 2.88 | 24 | 4 |
| 31.75 | 2.82 | 56 | 10 |
| 32.34 | 2.77 | 22 | 4 |
| 32.96 | 2.72 | 19 | 3 |
| 33.84 | 2.65 | 25 | 4 |

Example 8

Preparation of Compound 1 Form VII

Method 37

101 mg of Compound 1 Form I-A was suspended in 0.5 mL of DMSO and sonicated. After stirring for 14 days at room temperature, the solid was collected by filtration and dried under vacuum for 30 minutes to give Form VII. TG-FTIR investigation showed that Form VII was a DMSO solvate with a loss of 9.9 wt.-% of DMSO from 25° C.-150° C. (8.2 wt.-% DMSO would correspond to a hemi-solvate; 15.1 wt.-% would correspond to a monosolvate) indicating the Form VII is a DMSO solvate. PXRD and FT-Raman characterization of Compound I Form VII is provided in FIGS. 25 and 26, respectively. Table 6 lists the PXRD peak positions, peak intensities, and d values of Compound I Form VII.

TABLE 6

| Angle (2-Theta °) | d value (Angstrom) | Intensity (Cps) | Intensity (%) |
|---|---|---|---|
| 6.64 | 13.3 | 175 | 19 |
| 8.18 | 10.8 | 185 | 20 |
| 9.71 | 9.1 | 928 | 100 |
| 10.44 | 8.5 | 114 | 12 |
| 10.80 | 8.2 | 30 | 3 |
| 11.69 | 7.6 | 81 | 9 |
| 13.30 | 6.7 | 236 | 26 |
| 13.64 | 6.5 | 93 | 10 |
| 15.35 | 5.77 | 71 | 8 |
| 16.22 | 5.46 | 201 | 22 |
| 16.44 | 5.39 | 117 | 13 |
| 17.23 | 5.14 | 58 | 6 |
| 17.73 | 5.00 | 290 | 31 |
| 18.16 | 4.88 | 70 | 8 |
| 19.46 | 4.56 | 178 | 19 |
| 19.72 | 4.50 | 90 | 10 |
| 19.97 | 4.44 | 147 | 16 |
| 20.70 | 4.29 | 60 | 7 |
| 20.98 | 4.23 | 416 | 45 |
| 21.20 | 4.19 | 309 | 33 |
| 21.52 | 4.13 | 59 | 6 |
| 21.98 | 4.04 | 75 | 8 |
| 22.57 | 3.94 | 105 | 11 |
| 22.76 | 3.90 | 361 | 39 |
| 23.09 | 3.85 | 161 | 17 |
| 23.75 | 3.74 | 107 | 12 |
| 24.37 | 3.65 | 173 | 19 |
| 24.68 | 3.60 | 188 | 20 |
| 25.31 | 3.52 | 42 | 5 |
| 25.97 | 3.43 | 93 | 10 |
| 26.25 | 3.39 | 65 | 7 |
| 26.49 | 3.36 | 67 | 7 |
| 26.72 | 3.33 | 226 | 24 |
| 28.13 | 3.17 | 40 | 4 |
| 29.39 | 3.04 | 271 | 29 |
| 29.88 | 2.99 | 46 | 5 |
| 30.92 | 2.89 | 52 | 6 |
| 31.17 | 2.87 | 50 | 5 |
| 31.70 | 2.82 | 88 | 10 |
| 31.96 | 2.80 | 60 | 6 |
| 33.57 | 2.67 | 59 | 6 |
| 34.83 | 2.57 | 45 | 5 |

TABLE 7

| Angle (2-Theta °) | d value (Angstrom) | Intensity (Cps) | Intensity (%) |
|---|---|---|---|
| 7.48 | 11.8 | 16 | 5 |
| 8.31 | 10.6 | 9 | 3 |
| 10.05 | 8.8 | 332 | 96 |
| 10.77 | 8.2 | 346 | 100 |
| 12.27 | 7.2 | 15 | 4 |
| 13.65 | 6.5 | 30 | 9 |
| 14.06 | 6.3 | 106 | 31 |
| 15.60 | 5.68 | 44 | 13 |
| 16.03 | 5.53 | 25 | 7 |
| 16.76 | 5.29 | 264 | 76 |
| 16.96 | 5.23 | 31 | 9 |
| 17.16 | 5.16 | 40 | 12 |
| 18.11 | 4.90 | 147 | 43 |
| 18.32 | 4.84 | 100 | 29 |
| 18.43 | 4.81 | 79 | 23 |
| 18.65 | 4.75 | 38 | 11 |
| 19.89 | 4.46 | 56 | 16 |
| 20.28 | 4.38 | 28 | 8 |
| 20.89 | 4.25 | 149 | 43 |
| 21.71 | 4.09 | 193 | 56 |
| 21.87 | 4.06 | 68 | 20 |
| 24.07 | 3.69 | 105 | 30 |
| 24.90 | 3.57 | 200 | 58 |
| 25.28 | 3.52 | 61 | 18 |
| 25.54 | 3.49 | 20 | 6 |
| 25.86 | 3.44 | 18 | 5 |
| 26.22 | 3.40 | 10 | 3 |
| 26.66 | 3.34 | 5 | 2 |
| 27.74 | 3.21 | 31 | 9 |
| 28.44 | 3.14 | 30 | 9 |
| 28.71 | 3.11 | 208 | 60 |
| 29.08 | 3.07 | 11.6 | 3 |
| 30.26 | 2.95 | 15 | 4 |
| 31.16 | 2.87 | 18.3 | 5 |
| 32.59 | 2.75 | 7.95 | 2 |
| 32.85 | 2.72 | 31.4 | 9 |
| 34.01 | 2.63 | 18.7 | 5 |
| 34.68 | 2.59 | 11.9 | 3 |
| 35.09 | 2.56 | 15.7 | 5 |

Example 9

Preparation of Compound 1 Form VIII

Method 38

Figure 27:
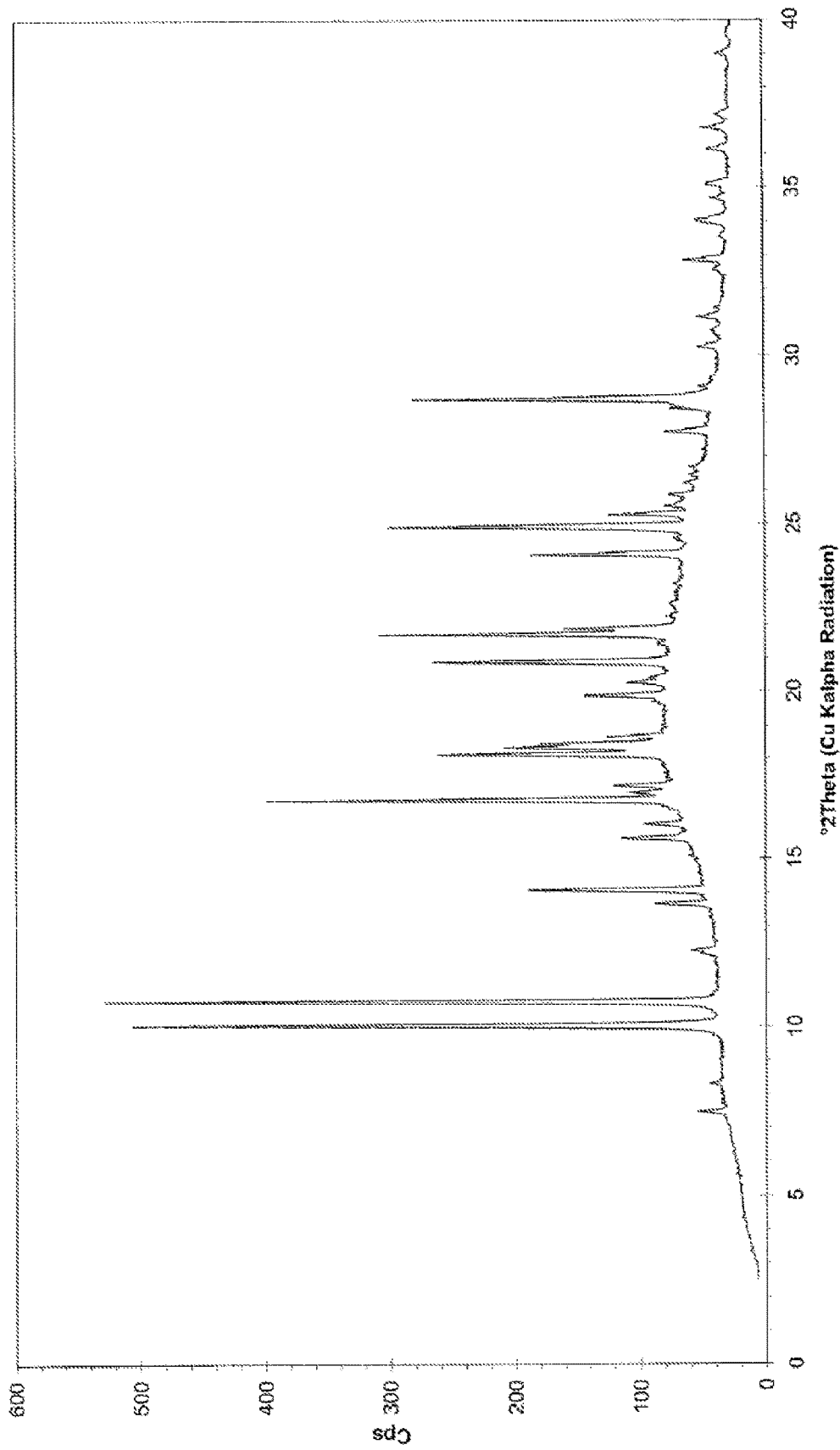
FIG. 27 is a PXRD diffractogram of pure Form VIII of Compound 1.
Figure 28:
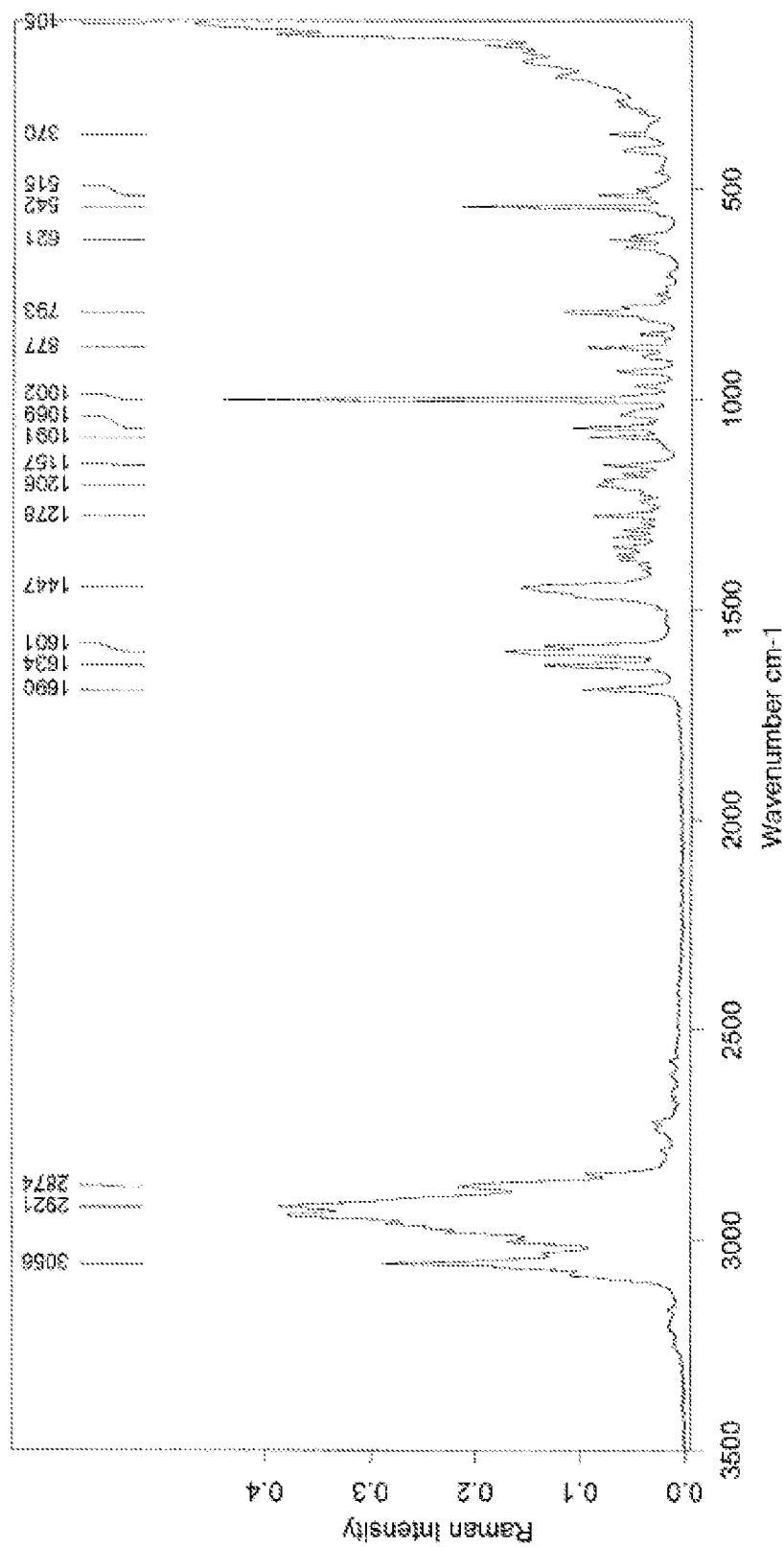
FIG. 28 is a FT-Raman spectrum of pure Form VIII of Compound 1.

199 mg of Compound 1 Form I-A was dissolved in 0.32 mL of benzyl alcohol and 2.0 mL of methylcyclohexane was added. After stirring at 5° C. for 4 h a turbid solution was obtained. The solvent was evaporated at 5° C. The solid was collected by filtration and dried under vacuum for 45 minutes to give Form VIII. (FIGS. 27 and 28). Table 7 lists the PXRD peak positions, peak intensities, and d values of Compound I Form VIII. TG-FTIR investigation showed a loss of 63.0 wt.-% benzyl alcohol from 25° C.-250° C. The sample was likely incompletely dried but might also correspond to a solvate. The sample was investigated again after 2 weeks. It was found to be still in a wet state and to correspond to the same form. Then the sample was dried for 1 day under nitrogen flow and subsequently for 6 days under vacuum at room temperature. It then appeared to be a dry powder, the FT-Raman spectrum corresponded to Form VIII, and TG-FTIR investigation showed a loss of 8.9 wt.-% of benzyl alcohol (not all solvent released).

Example 10

Preparation of Compound 1 Form IX

Method 39

Figure 29:
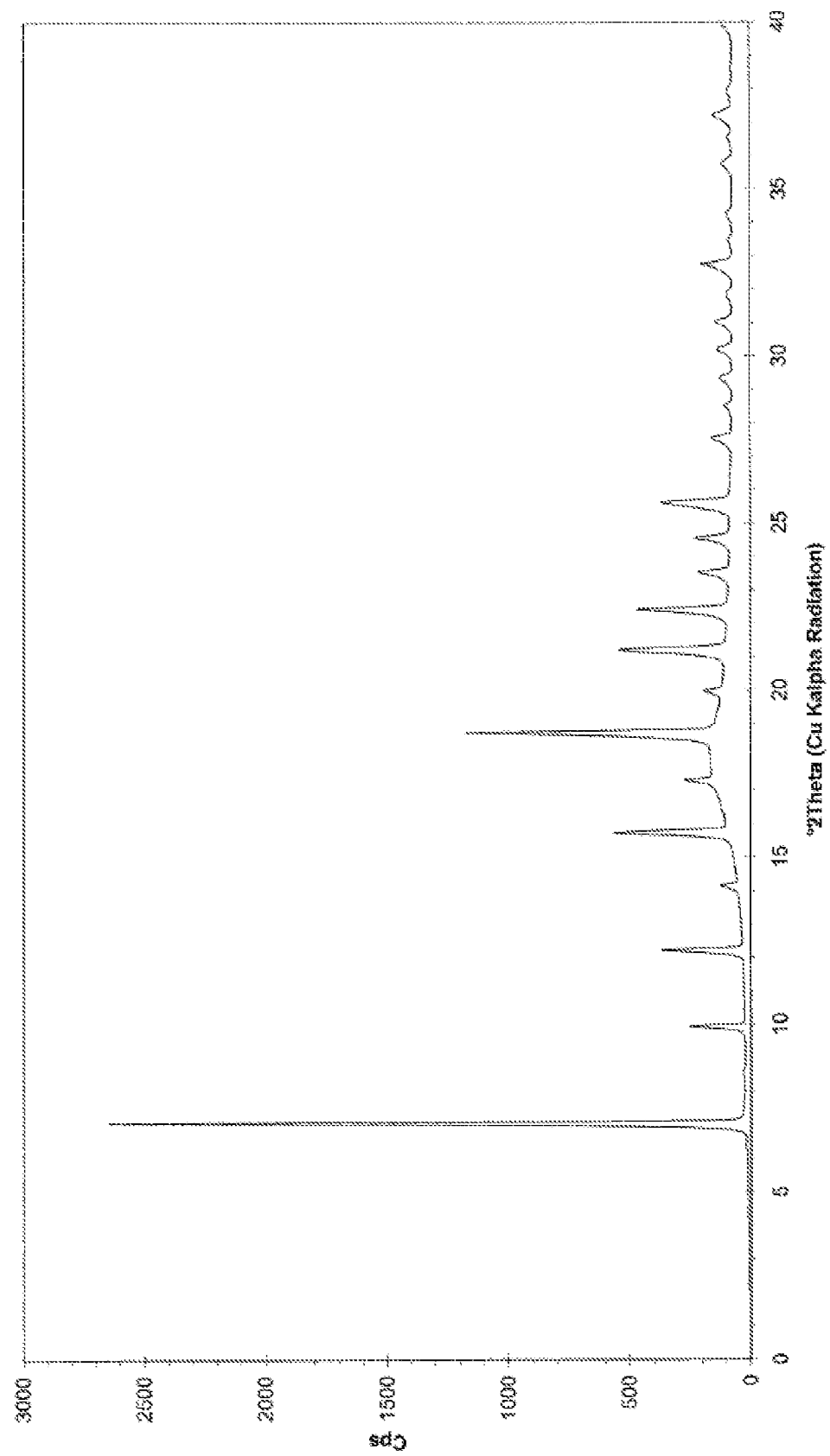
FIG. 29 is a PXRD diffractogram of pure Form IX of Compound 1.
Figure 30:
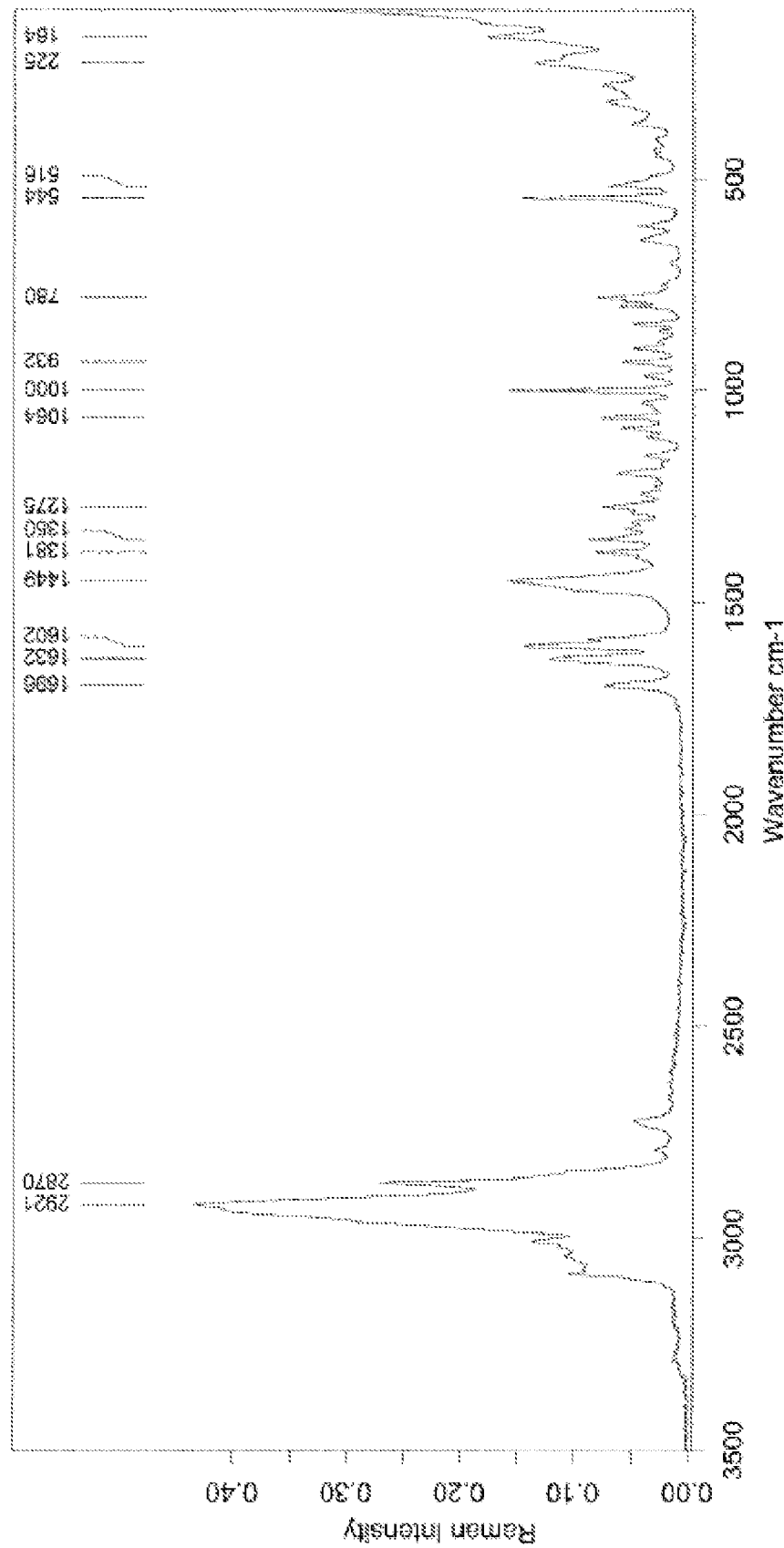
FIG. 30 is a FT-Raman spectrum of pure Form IX of Compound 1.

198 mg of Compound 1 Form I-A was dissolved in 0.2 mL acetone and 2.0 mL of cyclohexane. The solution was stirred at 5° C. for 4 hours than evaporated at 5° C. for 2 hours to obtain a precipitate. The precipitate was collected by filtration and dried under vacuum for 1 hour to give Form IX (FIGS. 29 and 30). Table 8 lists the PXRD peak positions, peak intensities, and d values of Compound I Form IX. TG-FTIR investigation showed a loss of 51.2 wt.-% of cyclohexane from 25° C.-150° C. The sample was likely incompletely dried but might also correspond to a cyclohexane solvate. Reinvestigation of the sample by PXRD and FT-Raman spectroscopy shows that the sample had spontaneously transformed into Form II.

TABLE 8

| Angle (2-Theta °) | d value (Angstrom) | Intensity (Cps) | Intensity (%) |
|---|---|---|---|
| 7.06 | 12.5 | 1799 | 100 |
| 9.93 | 8.9 | 160 | 9 |
| 12.22 | 7.2 | 230 | 13 |
| 14.13 | 6.3 | 53 | 3 |
| 15.74 | 5.63 | 326 | 18 |
| 17.28 | 5.13 | 98 | 6 |

TABLE 8-continued

| Angle (2-Theta °) | d value (Angstrom) | Intensity (Cps) | Intensity (%) |
|---|---|---|---|
| 18.71 | 4.74 | 741 | 41 |
| 19.96 | 4.44 | 53 | 3 |
| 21.18 | 4.19 | 290 | 16 |
| 22.39 | 3.97 | 260 | 15 |
| 23.51 | 3.78 | 90 | 5 |
| 24.54 | 3.63 | 105 | 6 |
| 25.58 | 3.48 | 188 | 11 |
| 27.52 | 3.24 | 57 | 3 |
| 28.48 | 3.13 | 26 | 1 |
| 29.33 | 3.04 | 36 | 2 |
| 30.18 | 2.96 | 42 | 2 |
| 31.01 | 2.88 | 51 | 3 |
| 31.82 | 2.81 | 15 | 1 |
| 32.73 | 2.73 | 95 | 5 |

Example 11

Preparation of Compound 1 Form X

Method 40

Figure 32:
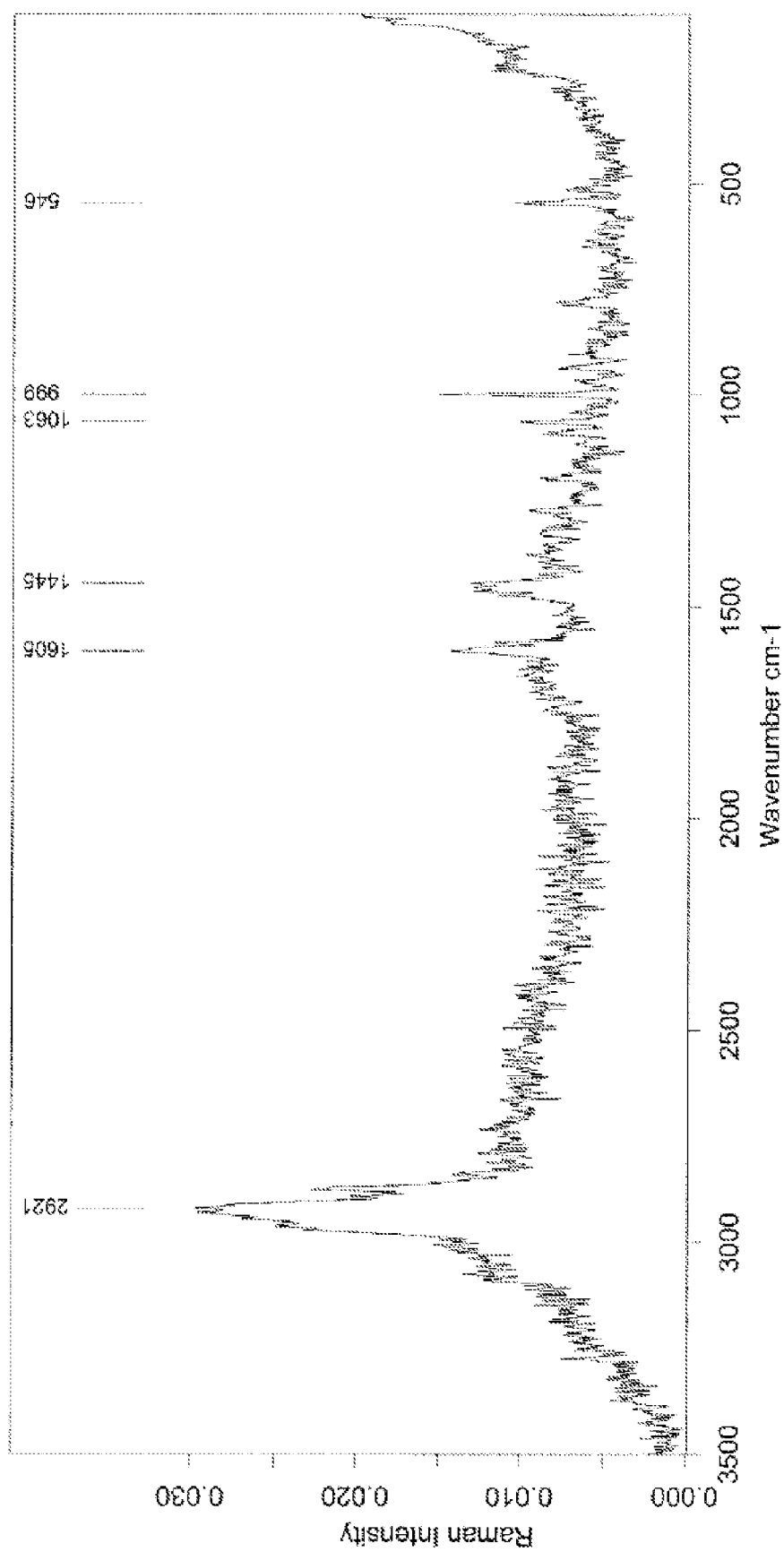
FIG. 32 is a FT-Raman spectrum of Form X of Compound 1.

128 mg of Compound 1 Form I-A was dissolved in 0.2 mL of formic acid. The solvent was evaporated under a stream of nitrogen for 1 day. The solid was dried under vacuum for 35 minutes to give Compound 1 as an amorphous solid (Form X) based on PXRD characterization (FIG. 31) and FT-Raman spectroscopy (FIG. 32).

Example 12

Solvent-Based Stability Tests in n-Heptane/Toluene

The thermodynamic stability of Form II and Form III as a function of temperature was investigated by suspension equilibration experiments.

Method 41

54.6 mg of Compound 1 Form III and 61.2 mg of Compound 1 Form II were suspended in 0.8 mL of 3:2 (v/v) n-heptane:toluene and sonicated. After stirring at 45° C. for 6 days the solid was collected by filtration and dried under vacuum for 1 hour to give a mixture of Form III and Form IV. In this experiment the starting material likely took up ambient humidity to give Form IV.

Method 42

18.5 mg of Compound 1 Form III and 28.0 mg of Compound 1 Form II were suspended in 0.4 mL of 3:2 (v/v) n-heptane:toluene and sonicated. After stirring at 60° C. for 6 days the solid was collected by filtration to give Form II.

Method 43

35.4 mg of Compound 1 Form III and 46.1 mg of Compound 1 Form II were suspended in 0.4 mL of 3:2 (v/v) n-heptane:toluene and sonicated. After stirring at 50° C. for 6 days the solid was collected by filtration to give a mixture of Form II and Form III.

Method 44

40.5 mg of Compound 1 Form III and 45.7 mg of Compound 1 Form II were suspended in 0.4 mL of 3:2 (v/v) n-heptane:toluene and sonicated. After stirring at 55° C. for 6 days the solid was collected by filtration to give Form II.

The solvent-based experiments are in principle thermodynamic stability tests between Compound 1 Forms II and III because mixtures of both forms were suspended. Below 45° C. Form III is the more stable form in 3:2 (v/v) n-heptane:toluene. Above 55° C. Form II is the more stable form in 3:2 (v/v) n-heptane:toluene. At 50° C. a mixture of both Form II and Form III was obtained in 3:2 (v/v) n-heptane:toluene. This is not unexpected. Close to the transition temperature, the thermodynamic driving force would be expected to be very small leading to slow transition rates. Possibly the kinetics of transformation were too slow for the transformation to occur on the timescale of the experiment. According to these suspension equilibration experiments, Form II and Form III are enantiotropic polymorphs. The thermodynamic transition temperature between Form II and Form III is between 45° C. and 55° C.

Example 13

Solvent-Based Stability Tests in n-Heptane/Ethanol

Compound 1 Form II, Compound 1 Form III, or a mixture of Compound 1 Forms II and III were slurried in 95:5 heptane:ethanol (anhydrous). After one day at various temperatures, a portion of the slurry was filtered and analyzed by XRPD. The results are presented in Table 9. A solution mediated transition occurs at 45-47° C. in 95:5 heptane:ethanol. Below 45° C. Compound 1 Form III is more stable; above 47° C. Compound 1 Form II is more stable.

TABLE 9

| Initial Form | Temperature (° C.) | Final Form |
|---|---|---|
| II | 25 | III |
| II and III | 40 | III |
| II and III | 45 | III |
| II and III | 47 | II |
| II and III | 48 | II |
| II and III | 49 | II |
| II and III | 50 | II |
| II and III | 55 | II |
| III | 60 | II |

Example 14

Solvent-Based Stability Tests in Water/Methanol

A mixture of Compound 1 Forms II, III, IV, and V was slurried in various compositions of methanol/water, or in water, for at least three days at different temperatures. The results are presented in Table 10. At a methanol content of more than 60% volume, Form V is the most stable polymorphic form of Compound 1 at all three temperatures. At a methanol content of less than 60% volume, Form IV is the most stable polymorphic form of Compound 1 at all three temperatures.

TABLE 10

| Solvent | 25° C. Form | 45° C. Form | 55° C. Form |
|---|---|---|---|
| 8:2 MeOH:water | V | V | V |
| 7:3 MeOH:water | V | V | V |
| 6:4 MeOH:water | V | IV and V | IV and V |
| 5:5 MeOH:water | IV | IV | IV |
| 4:6 MeOH:water | IV | IV | IV |
| 2:8 MeOH:water | IV | IV | IV |
| water | IV | IV | IV |

Example 15

Solid State Stability of Compound 1 Forms II, III, and IV at 60-65° C.

Compound 1 Form II, Compound 1 Form III, and Compound 1 Form IV were stored at 60-65° C. in a closed cap vial for various lengths of time. The results are presented in Table 11. Compound 1 Forms II and III remained unchanged under these conditions. Compound 1 Form IV is converted to a mixture of Forms II and III after 10 days at 60-65° C.

TABLE 11

| Initial Form | 3 days | 10 days | 18 days |
|---|---|---|---|
| II | II | II | II |
| III | III | III | III |
| IV | II, III, and IV | II and III | II and III |

Example 16

Gene Switch Efficacy of Compound 1

Cellular gene-switch assays were performed by transfecting the following constructs in mouse embryonic fibroblast cells (NIH3T3). The wild-type D-, E-, and F-domains from a) *C. fumiferana* EcR (CfEcR-DEF), and b) *C. fumiferana* EcR with a E274V/V390I/Y410E mutation (VY-CfEcR-DEF), were fused to a GAL4-DBD and placed under the control of the CMV promoter in a pBIND vector (Promega Corporation, Madison, Wis., USA). A chimeric RXR from *Homo sapiens* RXRb and *Locusta migratoria* RXR fused to VP16-AD and under the control of an SV40e promoter has previously described. (See, Kothapalli et al., *Dev. Genet.* 17:319-330 (1995); Palli, et al., *FEBS J.* 272:5979-5990 (2005); and U.S. Pat. No. 7,935,510 B2). The inducible luciferase reporter plasmid, pFRLuc, (Stratagene Cloning Systems, La Jolla, Calif., USA) contains five copies of the GAL4 response element and a synthetic minimal promoter.

Under standard assay conditions, Compound 1 was tested at 8 doses from 0.01-33 μM and the final DMSO concentration was 0.33% in both control and treatment wells. When necessary, Compound 1 was tested at lower concentrations. After a 48-hour post-treatment and transfection incubation, the cells were assayed for luciferase activity using the Bright-Glo™ Luciferase Assay System (Promega Corporation, Madison, Wis., USA) following the manufacturer's instructions. Assays were performed minimally in duplicate and definitive assays as many as six times. Data was fitted to a sigmoidal dose-response curve. Rel Max FI=maximum fold induction relative to a positive control. Results are presented in Table 12.

TABLE 12

| Assay | Result Type | Value |
|---|---|---|
| WT-Cf EcR | $EC_{50}$ | 1.8 nM |
|  | Rel Max FI | 0.99 |
| VY-Cf EcR | $EC_{50}$ | 0.133 nM |
|  | Rel Max FI | 0.88 |

Example 17

Clinical Study

The safety, tolerance, transgene function, and immunological effects of intratumoral injection(s) of adenoviral transduced autologous dendritic cells engineered to express hIL-12 and one or more other immunodulators under control of the RTS®, in human subjects with stage III and IV melanoma is evaluated through procedures such as those described below.

A study involving study human subjects with stage III and IV melanoma is conducted in 4 cohorts (groups) of subjects each subject receiving a single intratumoral injection (into a melanoma tumor) of adenoviral transduced autologous (re-inserted into the same subject that they came from) dendritic cells (DCs) engineered to express human interleukin-12 (hIL-12), and one or more other immunodulators, at a dose of $5 \times 10^7$ in combination with daily oral doses of one or more crystalline polymorphic forms of Compound 1, or a composition thereof (referred to collectively in this example as the "activator drug"). The study will use injections of dendritic cells transduced ex vivo (after the cells are removed from the subjects) with adenoviral vector for inducible expression of human IL-12 and one or more other immunodulators. The production of IL-12 and the one or more or other immunomodulators is "turned on" (induced) from the injected DCs through the activation of the RTS® by the oral administration of the activator drug. Safety and tolerance is assessed through physical examinations (including ECOG performance status), vital signs measurements, serum chemistry, urinalysis, hematology, adverse events "side-effects", and antibodies and cellular immune response to the adenovirus, components of RTS®, and the activator drug. To evaluate progress, single dose and steady-state pharmacokinetics/ADME of the activator drug, analysis of hIL-12 levels, other immunomodulator levels, and cellular immune response (T cells) in biopsies of the target tumors, draining lymph nodes, and peripheral circulation, as well as a serum cytokine profile is measured.

For instance, 16 subjects with stage III and IV melanoma are divided into four cohorts with cohorts 1 and 2 containing three subjects and cohorts 3 and 4 containing 5 subjects. All subjects will receive a single intratumoral injection of $5 \times 10^7$ autologous DC transduced with adenoviral vector encoding human IL-12 and one or more other immunodulators under the RTS® control. For example, the subjects are administered an intratumoral injection of autologous DC transduced with adenoviral vector encoding human IL-12 under the RTS® control and an immunomodulator such as IL-15 or IL-21.

The subjects will receive a single daily oral dose of the activator drug (cohort 1: 0.01 mg/kg, cohort 2: 0.1 mg/kg, cohort 3: 1.0 mg/kg or cohort 4: 3 mg/kg) the first dose starting approximately 3 hours prior to the DC injection on day 1 and continuing for 13 more consecutive days. Additional injection(s) of adenovirally transduced autologous dendritic cells in combination with 14 single (once) daily oral doses of activator drug may be administered to eligible subjects who meet the criteria for retreatment. Safety, tolerance, and dendritic cell function are assessed for all subjects in each group of cohort 1 for up to one month after injection of the in vitro engineered dendritic cells before enrolling subjects to receive the next highest dose of the activator drug. The safety assessment will continue in all subjects for 3 months after the initial injection of the engineered dendritic cells with the possibility of extending the follow-up period to a total of six months to monitor subject safety if toxicity is observed or the subject receives additional injection(s) of the dendritic cells.

Such a study demonstrates the safety and tolerance of a single or multiple intratumoral injection(s) of adenoviral transduced autologous dendritic cells in combination with the oral activator drug in subjects with melanoma. The study provides steady-state pharmacokinetics/ADME of the oral activator drug. The study demonstrates functionality of the RTS® in subjects by measuring hIL-12 expression and the expression of the one or more other immunomodulators of adenovirus transduced autologous dendritic cells in target tumor and/or draining lymph nodes in response to the activation of the RTS® by the oral administration of the activator drug. Furthermore, the study demonstrates the immunological effects of the adenoviral transduced autologous dendritic cells in terms of the cellular immune response in the target tumor, draining lymph nodes, and peripheral circulation following oral administration of the activator drug.

Melanoma is selected as an exemplary cancer. Melanoma in particular among solid tumors has been shown to respond to immunotherapy approaches, and melanoma tumors are readily accessible for intratumoral injection and biopsy. The subjects included in the study have unresectable stage III or IV melanoma, which has at least 0.5 cm in diameter, any tumor thickness, any number of lymph node involvement, in-transit metastases, or distant metastases.

It is to be understood that the foregoing described embodiments and exemplifications are not intended to be limiting in any respect to the scope of the disclosure, and that the claims presented herein are intended to encompass all embodiments and exemplifications whether or not explicitly presented herein All patents and publications cited herein are fully incorporated by reference in their entirety.

What is claimed is:

1. Crystalline (R)-3,5-dimethyl-benzoic acid N-(1-tert-butyl-butyl)-N'-(2-ethyl-3-methoxy-benzoyl)-hydrazide Form V, Form VI, Form VII, Form VIII, or Form IX wherein:
Form V is characterized as having a powder x-ray diffraction pattern with peaks at 9.38, 12.22, 13.18, 14.98, 17.32, 18.40, 22.41, 23.40, 23.55, 24.63, 24.79, 25.61, 28.02, and 31.77 degrees 2Θ;
Form VI is characterized as having a powder x-ray diffraction pattern with peaks at 9.38, 12.23, 13.25, 17.48, 18.41, and 22.41 degrees 2Θ;
Form VII is characterized as having a powder x-ray diffraction pattern with peaks at 8.18, 9.71, 13.30, 16.22, 17.73, 20.98, 21.20, 22.76, 24.68, 26.72, and 29.39 degrees 2Θ;
Form VIII is characterized as having a powder x-ray diffraction pattern with peaks at 10.05, 10.77, 14.06, 16.76, 18.11, 18.32, 18.43, 20.89, 21.71, 21.87, 24.07, 24.90, and 28.71 degrees 2Θ; and
Form IX is characterized as having a powder x-ray diffraction pattern with peaks at 7.06, 15.74, and 18.71 degrees 2Θ.

2. The crystalline (R)-3,5-dimethyl-benzoic acid N-(1-tert-butyl-butyl)-N'-(2-ethyl-3-methoxy-benzoyl)-hydrazide form of claim 1 having an average particle size distribution of about 10 μm or less.

3. The crystalline (R)-3,5-dimethyl-benzoic acid N-(1-tert-butyl-butyl)-N'-(2-ethyl-3-methoxy-benzoyl)-hydrazide form of claim 2 having an average particle size distribution of about 1 μm or less.

4. A composition comprising the crystalline (R)-3,5-dimethyl-benzoic acid N-(1-tert-butyl-butyl)-N'-(2-ethyl-3-methoxy-benzoyl)-hydrazide form of claim 1 and one or more excipients.

5. The composition of claim 4, wherein said one or more excipients comprise one or more pharmaceutically acceptable excipients.

6. The composition of claim 5, wherein said one or more pharmaceutically acceptable excipients comprise Miglyol 812, phospholipon 90G, or tocopheryl polyethylene glycol 1000 succinate, or a mixture thereof.

7. The composition of claim 6, wherein said one or more pharmaceutically acceptable excipients consist essentially of Miglyol 812, phospholipon 90G, and tocopheryl polyethylene glycol 1000 succinate.

8. A kit comprising the crystalline (R)-3,5-dimethyl-benzoic acid N-(1-tert-butyl-butyl)-N'-(2-ethyl-3-methoxy-benzoyl)-hydrazide form of claim 1.

9. A kit comprising the composition of claim 4.

* * * * *

SEQUENCE LISTING

```
<160> NUMBER OF SEQ ID NOS: 2

<210> SEQ ID NO 1
<211> LENGTH: 240
<212> TYPE: PRT
<213> ORGANISM: Choristoneura fumiferana

<400> SEQUENCE: 1

Leu Thr Ala Asn Gln Gln Phe Leu Ile Ala Arg Leu Ile Trp Tyr Gln
1               5                   10                  15

Asp Gly Tyr Glu Gln Pro Ser Asp Glu Asp Leu Lys Arg Ile Thr Gln
            20                  25                  30

Thr Trp Gln Gln Ala Asp Asp Glu Asn Glu Glu Ser Asp Thr Pro Phe
        35                  40                  45

Arg Gln Ile Thr Glu Met Thr Ile Leu Thr Val Gln Leu Ile Val Glu
    50                  55                  60

Phe Ala Lys Gly Leu Pro Gly Phe Ala Lys Ile Ser Gln Pro Asp Gln
65                  70                  75                  80

Ile Thr Leu Leu Lys Ala Cys Ser Ser Glu Val Met Met Leu Arg Val
                85                  90                  95

Ala Arg Arg Tyr Asp Ala Ala Ser Asp Ser Val Leu Phe Ala Asn Asn
            100                 105                 110

Gln Ala Tyr Thr Arg Asp Asn Tyr Arg Lys Ala Gly Met Ala Tyr Val
        115                 120                 125

Ile Glu Asp Leu Leu His Phe Cys Arg Cys Met Tyr Ser Met Ala Leu
    130                 135                 140

Asp Asn Ile His Tyr Ala Leu Leu Thr Ala Val Val Ile Phe Ser Asp
145                 150                 155                 160

Arg Pro Gly Leu Glu Gln Pro Gln Leu Val Glu Glu Ile Gln Arg Tyr
                165                 170                 175

Tyr Leu Asn Thr Leu Arg Ile Tyr Ile Leu Asn Gln Leu Ser Gly Ser
            180                 185                 190

Ala Arg Ser Ser Val Ile Tyr Gly Lys Ile Leu Ser Ile Leu Ser Glu
        195                 200                 205

Leu Arg Thr Leu Gly Met Gln Asn Ser Asn Met Cys Ile Ser Leu Lys
    210                 215                 220

Leu Lys Asn Arg Lys Leu Pro Pro Phe Leu Glu Glu Ile Trp Asp Val
225                 230                 235                 240

<210> SEQ ID NO 2
<211> LENGTH: 10
```

```
<212> TYPE: PRT
<213> ORGANISM: Artificial Sequence
<220> FEATURE:
<223> OTHER INFORMATION: Helokinestatin

<400> SEQUENCE: 2

Gly Pro Pro Tyr Gln Pro Leu Val Pro Arg
1               5                   10
```